United States Patent
Taylor et al.

(10) Patent No.: US 6,576,476 B1
(45) Date of Patent: *Jun. 10, 2003

(54) CHEMILUMINESCENCE DETECTION METHOD AND DEVICE

(75) Inventors: Michael T. Taylor, Newark, CA (US); Amer El-Hage, Menlo Park, CA (US); Glenn R. Edwards, Palo Alto, CA (US); Douglas N. Modlin, Palo Alto, CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/302,158

(22) Filed: Apr. 29, 1999

Related U.S. Application Data

(62) Division of application No. 09/146,081, filed on Sep. 2, 1998, now Pat. No. 6,187,267.

(51) Int. Cl.⁷ .............................................. G01N 21/17
(52) U.S. Cl. ......................... 436/172; 436/48; 422/52; 422/65
(58) Field of Search ............................. 422/62, 63, 65, 422/67, 52, 82.05; 436/43, 45, 46, 48, 50, 164, 172

(56) References Cited

U.S. PATENT DOCUMENTS

| | | |
|---|---|---|
| 2,719,214 A | 9/1955 | Potter |
| 3,013,467 A | 12/1961 | Minsky |
| 3,423,581 A | 1/1969 | Baer |
| 3,516,736 A | 6/1970 | Weaver |
| 3,849,654 A | 11/1974 | Malvin |
| 3,885,162 A | 5/1975 | Geertz |
| 3,932,023 A | 1/1976 | Humer |

(List continued on next page.)

FOREIGN PATENT DOCUMENTS

| | | |
|---|---|---|
| EP | 0 266 881 A2 | 5/1988 |
| EP | 0 259 386 B1 | 4/1991 |
| EP | 0 977 037 A1 | 2/2000 |
| EP | 0 993 916 A2 | 4/2000 |
| EP | 0 995 555 A1 | 4/2000 |
| EP | 1 003 020 A1 | 5/2000 |
| GB | 2 215 838 A | 9/1989 |
| GB | 2 228 081 A | 8/1990 |
| WO | WO 99/08233 | 2/1999 |
| WO | WO 00/50877 | 8/2000 |
| WO | WO 00/55372 | 9/2000 |
| WO | WO 00/66269 | 11/2000 |
| WO | WO 01/04608 | 1/2001 |

(List continued on next page.)

OTHER PUBLICATIONS

*Sorting Single Molecules: Application to Diagnostics and Evolutionary Biotechnology*, Eigen et al., *PNAS*, Vol. 91, pp. 5740–5747, 1994.
*A Microfabricated Fluorescence–activated Cell Sorter*, Fu et al., *Nature Biotechnology*, Vol. 17, pp. 1109–1111, 1999.
*Electrochemiluminescence: A New Diagnostic and Research Tool*, Yang et al., *Bio/Technology*, Vol. 12, pp. 193–194, Feb. 1994.

(List continued on next page.)

*Primary Examiner*—Lyle A. Alexander
(74) *Attorney, Agent, or Firm*—Kolisch Hartwell, PC

(57) ABSTRACT

A device for detecting chemiluminescence from a sample. The device may include a stage for supporting a sample and one or more of the following elements: (1) an optics head, (2) an optical relay structure for transmitting chemiluminescence from the sample to a detector, (3) a drive mechanism, (4) a sensor for detecting proximity of the optical relay structure to the sample, (5) a mask structure for selecting an effective diameter of the optical relay structure, and (6) a baffle for blocking extraneous light from entering the optical relay structure.

29 Claims, 32 Drawing Sheets

U.S. PATENT DOCUMENTS

| | | |
|---|---|---|
| 4,011,451 A | 3/1977 | Nelson |
| 4,067,653 A | 1/1978 | Fletcher et al. |
| 4,074,939 A | 2/1978 | Rabl |
| 4,076,420 A | 2/1978 | De Maeyer et al. |
| 4,100,416 A | 7/1978 | Hirschfeld |
| 4,144,452 A | 3/1979 | Harte |
| 4,150,870 A | 4/1979 | d'Auria |
| 4,203,670 A | 5/1980 | Bromberg |
| 4,240,751 A | 12/1980 | Linnecke et al. |
| 4,296,326 A | 10/1981 | Haslop et al. |
| 4,341,957 A | 7/1982 | Wieder |
| 4,397,560 A | 8/1983 | Andresen |
| 4,451,149 A | 5/1984 | Noeller |
| 4,485,430 A | 11/1984 | Achiaga Fustel |
| 4,501,970 A | 2/1985 | Nelson |
| 4,567,847 A | 2/1986 | Linner |
| 4,626,684 A | 12/1986 | Landa |
| 4,646,214 A | 2/1987 | Mendleski |
| 4,647,544 A * | 3/1987 | Nicoli et al. ............. 250/461.1 |
| 4,685,801 A | 8/1987 | Minekane |
| 4,699,512 A | 10/1987 | Koshi |
| 4,704,255 A | 11/1987 | Jolley |
| 4,704,353 A | 11/1987 | Humphries et al. |
| 4,707,067 A | 11/1987 | Haberland et al. |
| 4,724,217 A | 2/1988 | Miller |
| 4,730,921 A | 3/1988 | Klein et al. |
| 4,737,464 A | 4/1988 | McConnell et al. |
| 4,738,825 A | 4/1988 | Kelln et al. |
| 4,741,619 A | 5/1988 | Humphries |
| 4,753,501 A | 6/1988 | Battle |
| 4,758,786 A | 7/1988 | Hafeman |
| 4,762,420 A | 8/1988 | Bowley |
| 4,772,453 A | 9/1988 | Lisenbee |
| 4,784,275 A | 11/1988 | Fridge |
| 4,801,804 A | 1/1989 | Rosenthal |
| 4,802,768 A | 2/1989 | Gifford et al. |
| 4,808,828 A | 2/1989 | Kitamori et al. |
| 4,810,096 A | 3/1989 | Russell et al. |
| 4,826,660 A | 5/1989 | Smith et al. |
| 4,849,330 A | 7/1989 | Humphries et al. |
| 4,855,930 A | 8/1989 | Chao et al. |
| 4,868,103 A | 9/1989 | Stavrianopoulos et al. |
| 4,873,633 A | 10/1989 | Mezei et al. |
| 4,877,965 A | 10/1989 | Dandliker et al. |
| 4,883,579 A | 11/1989 | Humphries et al. |
| 4,885,087 A | 12/1989 | Kopf |
| 4,892,409 A | 1/1990 | Smith |
| 4,897,548 A | 1/1990 | Döme et al. |
| 4,911,794 A | 3/1990 | Parce et al. |
| 4,915,812 A | 4/1990 | Parce et al. |
| 4,923,819 A | 5/1990 | Fernandez et al. |
| 4,931,402 A | 6/1990 | Abplanalp |
| 4,936,682 A | 6/1990 | Hoyt |
| 4,948,442 A | 8/1990 | Manns |
| 4,963,815 A | 10/1990 | Hafeman |
| 4,968,148 A | 11/1990 | Chow et al. |
| 4,979,821 A | 12/1990 | Schutt et al. |
| 5,009,488 A | 4/1991 | Fay et al. |
| 5,018,866 A | 5/1991 | Osten |
| 5,020,995 A | 6/1991 | Levy |
| 5,034,613 A | 7/1991 | Denk et al. |
| 5,039,219 A | 8/1991 | James et al. |
| 5,047,215 A | 9/1991 | Manns |
| 5,058,045 A | 10/1991 | Ma |
| 5,082,628 A | 1/1992 | Andreotti et al. |
| 5,084,246 A | 1/1992 | Lyman et al. |
| 5,091,652 A | 2/1992 | Mathies et al. |
| 5,095,517 A | 3/1992 | Monguzzi et al. |
| 5,096,807 A | 3/1992 | Leaback |
| 5,104,804 A | 4/1992 | Humphries et al. |
| 5,112,134 A | 5/1992 | Chow et al. |
| 5,160,702 A | 11/1992 | Kopf-Sill et al. |
| 5,164,319 A | 11/1992 | Hafeman et al. |
| 5,169,601 A | 12/1992 | Ohta et al. |
| 5,192,510 A | 3/1993 | Zoha et al. |
| 5,198,670 A | 3/1993 | VanCauter et al. |
| 5,206,568 A * | 4/1993 | Bjornson et al. ........ 318/568.1 |
| 5,208,161 A | 5/1993 | Saunders et al. |
| 5,208,651 A | 5/1993 | Buican |
| 5,216,488 A | 6/1993 | Tuunanen et al. |
| 5,225,164 A | 7/1993 | Astle |
| 5,257,202 A | 10/1993 | Feddersen et al. |
| 5,270,788 A | 12/1993 | Cercek et al. |
| 5,273,718 A | 12/1993 | Sköld et al. |
| 5,275,951 A | 1/1994 | Chow et al. |
| 5,278,048 A | 1/1994 | Parce et al. |
| 5,289,407 A | 2/1994 | Strickler et al. |
| 5,307,144 A | 4/1994 | Hiroshi et al. |
| 5,315,015 A | 5/1994 | Hui et al. |
| 5,317,485 A | 5/1994 | Merjanian |
| 5,319,436 A | 6/1994 | Manns et al. |
| 5,323,008 A | 6/1994 | Studholme et al. |
| 5,323,010 A | 6/1994 | Gratton et al. |
| 5,340,716 A | 8/1994 | Ullman et al. |
| 5,340,747 A | 8/1994 | Eden |
| 5,341,215 A | 8/1994 | Seher |
| 5,353,112 A | 10/1994 | Smith |
| 5,355,215 A | 10/1994 | Schroeder et al. |
| 5,361,626 A | 11/1994 | Colligan et al. |
| 5,384,093 A | 1/1995 | Ootani et al. |
| 5,395,503 A | 3/1995 | Parce et al. |
| 5,401,465 A | 3/1995 | Smethers et al. |
| 5,418,371 A | 5/1995 | Aslund et al. |
| 5,420,408 A | 5/1995 | Weyrauch et al. |
| 5,436,718 A | 7/1995 | Fernandes et al. |
| 5,445,935 A | 8/1995 | Royer |
| 5,449,921 A | 9/1995 | Baba |
| 5,457,527 A | 10/1995 | Manns et al. |
| 5,459,300 A | 10/1995 | Kasman |
| 5,480,804 A | 1/1996 | Niwa et al. |
| 5,485,530 A | 1/1996 | Lakowicz et al. |
| 5,487,872 A | 1/1996 | Hafeman et al. |
| 5,491,343 A | 2/1996 | Brooker |
| 5,496,697 A | 3/1996 | Parce et al. |
| 5,500,188 A | 3/1996 | Hafeman et al. |
| 5,512,492 A | 4/1996 | Herron et al. |
| 5,523,573 A | 6/1996 | Hänninen et al. |
| 5,527,684 A | 6/1996 | Mabile et al. |
| 5,528,046 A | 6/1996 | Ishikawa |
| 5,529,752 A | 6/1996 | Pontis et al. |
| 5,537,343 A | 7/1996 | Kikinis et al. |
| 5,541,113 A | 7/1996 | Siddigi et al. |
| 5,542,012 A | 7/1996 | Fernandes et al. |
| 5,557,398 A | 9/1996 | Wechsler et al. |
| 5,561,068 A | 10/1996 | Rounbehler et al. |
| 5,567,302 A | 10/1996 | Song et al. |
| 5,589,136 A | 12/1996 | Northrup et al. |
| 5,589,350 A | 12/1996 | Bochner |
| 5,589,351 A | 12/1996 | Harootunian |
| 5,592,289 A | 1/1997 | Norris |
| 5,593,867 A | 1/1997 | Walker et al. |
| 5,595,710 A | 1/1997 | Van Dusen et al. |
| 5,599,500 A | 2/1997 | Jones |
| 5,604,130 A | 2/1997 | Warner et al. |
| 5,620,894 A | 4/1997 | Barger et al. |
| 5,626,134 A | 5/1997 | Zuckerman |
| 5,631,734 A | 5/1997 | Stern et al. |
| 5,633,724 A | 5/1997 | King et al. |
| 5,635,402 A | 6/1997 | Alfano et al. |
| 5,641,633 A | 6/1997 | Linn et al. |
| 5,645,800 A | 7/1997 | Masterson et al. |
| 5,663,545 A | 9/1997 | Marquiss |
| 5,670,113 A | 9/1997 | Akong et al. |
| 5,672,880 A | 9/1997 | Kain |
| 5,676,943 A | 10/1997 | Baetge et al. |
| 5,677,196 A | 10/1997 | Herron et al. |
| 5,679,310 A | 10/1997 | Manns |
| 5,736,410 A | 4/1998 | Zarling et al. |
| 5,738,825 A | 4/1998 | Rudigier et al. |
| 5,746,974 A | 5/1998 | Massey et al. |

| | | |
|---|---|---|
| 5,750,410 A | 5/1998 | Dou et al. |
| 5,756,292 A | 5/1998 | Royer |
| 5,766,875 A | 6/1998 | Hafeman et al. |
| 5,780,857 A | 7/1998 | Harju et al. |
| 5,798,083 A | 8/1998 | Massey et al. |
| 5,798,085 A | 8/1998 | Seaton et al. |
| 5,825,617 A | 10/1998 | Kochis et al. |
| 5,842,582 A | 12/1998 | DeStefano, Jr. |
| 5,888,454 A | 3/1999 | Leistner et al. |
| 5,905,571 A | 5/1999 | Butler et al. |
| 5,933,232 A | 8/1999 | Atzler et al. |
| 5,959,738 A | 9/1999 | Hafeman et al. |
| 5,989,835 A | 11/1999 | Dunlay et al. |
| 5,993,746 A | 11/1999 | Priha et al. |
| 6,020,591 A | 2/2000 | Harter et al. |
| 6,025,985 A | 2/2000 | Leytes et al. |
| 6,033,100 A | 3/2000 | Marquiss et al. |
| 6,071,748 A * | 6/2000 | Modlin et al. ............... 436/174 |
| 6,137,584 A | 10/2000 | Seidel et al. |
| 6,187,267 B1 | 2/2001 | Taylor et al. |

OTHER PUBLICATIONS

*High Throughput Screening Using Dynamic Fluorescence*, Swift et al., *SPIE*, Vol. 2388, pp. 182–189, Feb. 6–8, 1995.
Genesis Series Robotic Sample Processors brochure, Tecan AG, Oct. 1997.
Genesis Robotic Microplate Processor brochure, Tecan AG, Nov. 1997.
A Measure of Brilliance, TR717 Microplate Luminometer brochure, Tropix, Inc., 1997.
Advanced Microplate Detection Systems brochure, Tecan AG, Feb. 1998.
The Spectra Family brochure, Tecan AG, Feb. 1998.
Assist Plate Handling Device brochure, Labsystems, May 1998.
Genesis Assay Workstation brochure, Tecan AG, Jul. 1998.
Genesis Logistics Workstation brochure, Tecan AG, Jul. 1998.
*Fixed Polarizer Ellipsometry for Simple and Sensitive Detection of Thin Films Generated by Specific Molecular Interactions: Applications in Immunoassays and DNA Sequence Detection*, Ostroff et a., *Clinical Chemistry*, Vol. 44, No. 9, pp. 2031–2035, 1998.
Microplate Instrumentation Catalogue 1998, Labsystems, 1998., only page 1 considered.
Twister™, Tecan's Automated Microplate Handler brochure, Tecan AG, Nov. 1999.
Magellan, Instrument Control and Data Analysis Software brochure, Tecan AG, Nov. 1999.
Absorbance Readers brochure, Tecan AG, Dec. 1999.
ULTRA—The Solution for HTS and Assay Development brochure, Tecan Austria GmbH, Dec. 1999.
CyBi™–PlateSafe brochure, CYBio AG, May 2000.
CyBi™–Lumax 1,536 brochure, CyBio AG, May 2000.
Packard BioScience Company Introduces the Fusion™ Universal Microplate Analyzer press release, Packard BioScience Company, June 29, 2000.
SPECTRAmax® GEMINI XS brochure, Molecular Devices Corp., June 2000.
SPECTRAmax® PLUS[384] brochure, Molecular Devices Corp., June 2000.
Labcyte: Research and Clinical Instruments for Life Sciences brochure, Arlena Research LLC, Aug. 1, 2000.
Fusion™, Universal Microplate Analyzer, Packard BioScience Company, August 2000.
CyBi™–Science–Machine: One System–Many Solutions brochure, CyBio AG, 2000.
FLIPR 384: Essential Technology for Drug Discovery brochure, Molecular Devices Corp., undated.
Acumen Explorer brochure, Acumen, undated.
FLUOstar Galaxy brochure, BMG Labtechnologies GmbH, undated.
LUMIstar Galaxy brochure, BMG Labtechnologies GmbH, undated.
NEPHELOstar brochure, BMG Labtechnologies GmbH, undated.
POLARstar Galaxy brochure, BMG Labtechnologies GmbH, undated.
POLARstar Galaxy flyer, BMG Labtechnologies, GmbH, undated.
*Fundamentals of Light Microscopy,* Spencer, Cambridge University Press, 1982. Only table of contents and preface considered.
*Basic Fluorescence Microscopy;* Taylor et al., *Methods in Cell Biology,* vol. 29, pp. 207–237, 1989.
*Quantitative Fluorescence Microscopy Using Photomultiplier Tubes and Imaging Detectors,* Wampler et al., *Methods in Cell Biology,* vol. 29, pp. 239–267, 1989.
*Three–Dimensional Confocal Fluorescence Microscopy,* Brakenhoff et al., *Methods in Cell Biology,* vol. 30, pp. 379–389, 1989.
*Laser–Scanning Confocal Microscopy of Living Cells,* Lemasters et al., *Optical Microscopy; Emerging Methods and Applications,* pp. 339–345, 1993.
*Time–Resolved Fluorescence Lifetime Imaging,* vande Ven et al., *Optical Microscopy; Emerging Methods and Applications,* pp. 373–389, 1993.
Tecan SPECTRAfluor—A Step Forward in Microplate Fluorometry, internet description pages, printed from internet on Jun. 17, 1998.
Wallac Time–Resolved Fluorometry—The Key to Improved Assay Sensitivity, internet description pages, printed from internet on Jul. 7, 1998.
Wallac 1234 DELFIA Fluorometer, internet description page, printed from internet on Jul. 7, 1998.
Wallac 1420 VICTOR Multilabel Counter, internet description pages, printed from internet on Jul. 7, 1998.
Wallac 1420 VICTOR[2] Multilabel Counter, internet description pages, printed from internet on Jul. 7, 1998.
Wallac 1442 ARTHUR Multi–Wavelength Fluoroimager, internet description page, printed from internet on Jul. 7, 1998.
Wallac Labelling Reagents for Time–Resolved Fluorometry, internet description page, printed from internet on Jul. 7, 1998.
Donald G. Fink and H. Wayne Beaty, Standard Handbook for Electrical Engineers, pp. 22–2 through 22–5 (11th ed. 1978).
Jeffrey Sipior et al, "A Lifetime–Based Optical $CO_2$ Gas Sensor with Blue or Red Excitation and Stokes or Anti–Stokes Detection," *Analytical Biochemistry,* 227, 309–318 (1995).

* cited by examiner

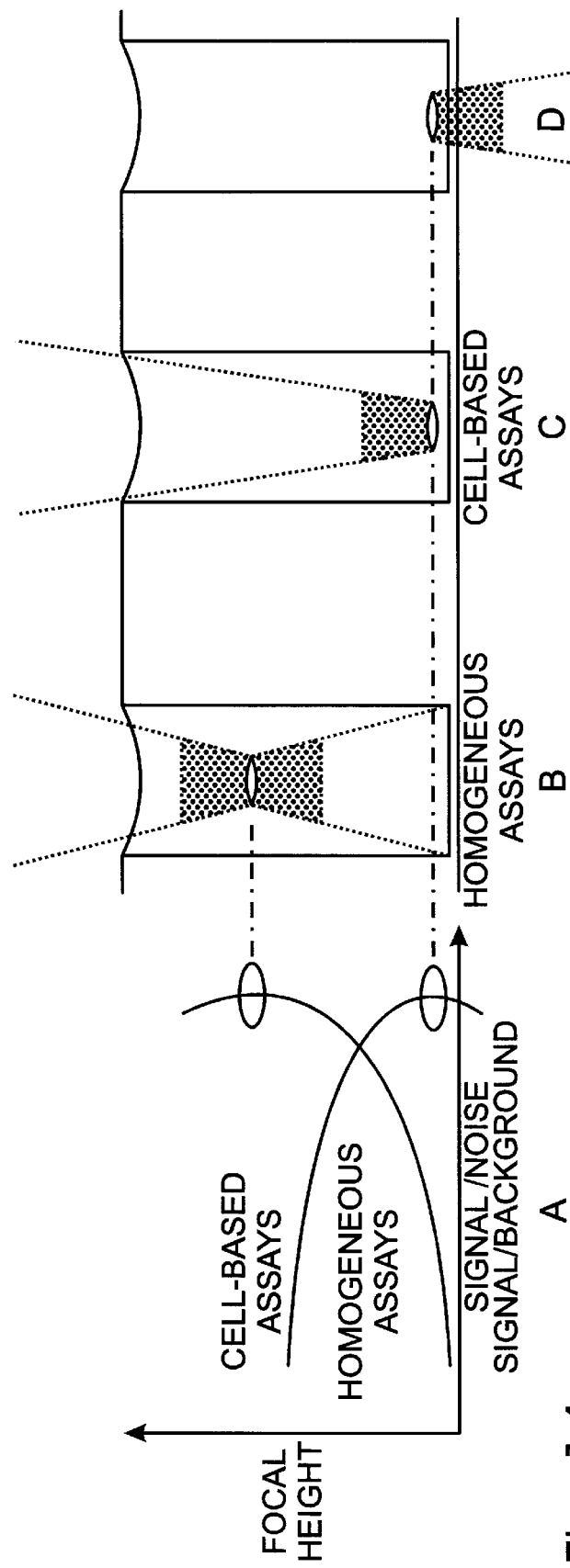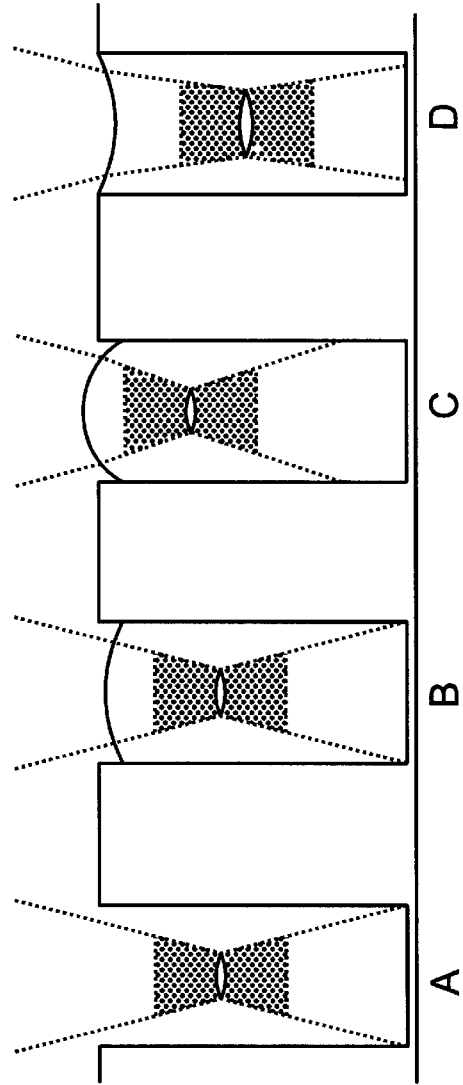
Fig. 14
Fig. 15

CHEMILUMINESCENCE DETECTION METHOD AND DEVICE

CROSS-REFERENCES TO RELATED APPLICATIONS

This application is a divisional continuation application of U.S. patent application Ser. No. 09/146,081, filed Sep. 2, 1998 now U.S. Pat. No. 6,187,267.

This application is a continuation of the following patent applications, each of which is incorporated herein by reference: U.S. patent application Ser. No. 09/062,472, filed Apr. 17, 1998; PCT Patent Application Ser. No. PCT/US98/14575, filed Jul. 15, 1998; U.S. patent application Ser. No. 09/118,141, filed Jul. 16, 1998; U.S. patent application Ser. No. 09/118,310, filed Jul. 16, 1998; U.S. patent application Ser. No. 09/118,341, filed Jul. 16, 1998; U.S. patent application Ser. No. 09/144,575, filed Aug. 31, 1998; and U.S. patent application Ser. No. 09/144,578, filed Aug. 31, 1998.

This application is based upon and claims benefit under 35 U.S.C. §119 of the following U.S. Provisional Patent Applications, each of which is incorporated herein by reference: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

FIELD OF THE INVENTION

The invention relates to a device for detecting light from a sample. More particularly, the invention relates to a device for detecting chemiluminescence light from a sample in a high-throughput screening procedure.

BACKGROUND OF THE INVENTION

High-throughput screening instruments (or analyzers) are critical tools in the pharmaceutical research industry and in the process of discovering and developing new drugs. High-throughput analyzers are used to assess the efficacy of candidate drug compounds. Dramatic increases in the number of these compounds and in the number of targets against which they may be directed have created a bottleneck in the development of new drugs and a need for analyzers that can operate with a high degree of analytical flexibility and speed. Analytical flexibility and speed are necessary because high-throughput applications may involve repeating the same operations hundreds of thousands of times, greatly magnifying even the smallest shortcomings.

Recently, improved sample containers and luminescence assays have been developed to facilitate high-throughput screening. The improved sample containers include microplates, which are generally rectangular containers that include a plurality of sample wells for holding a plurality of samples. Microplates enhance speed by reducing transit time between samples and reduce cost by employing small amounts of reagents. Unfortunately, microplates also have a number of shortcomings. For example, microplates do not conform to any exact standard, so that their size, shape, and construction materials may vary, depending on vendor or batch. In addition, microplates may vary from opaque to transparent, so that analytical approaches developed for some microplates will not work for other microplates. Moreover, preferred microplates may differ, depending on application. Furthermore, microplates may allot only a small volume for each sample, reducing signal and making it easier to spill sample during transit.

The improved luminescence assays include chemiluminescence and various photoluminescence assays. These assays must be conducted on sensitive analyzers, especially if performed using the small samples held in microplates. Increased sensitivity is particularly important for chemiluminescence assays, in which the amount of light generated by a sample may be quite small. These assays also differ in many respects, so that each may favor a different optical configuration. Consequently, in the high-throughput screening field, photoluminescence and chemiluminescence assays often are performed separately, using dedicated instruments.

SUMMARY OF THE INVENTION

The present invention provides a device for detecting chemiluminescence from a sample. The device may include a stage for supporting a sample and one or more of the following elements: (1) an optics head, (2) an optical relay structure for transmitting chemiluminescence from the sample to a detector, (3) a drive mechanism, (4) a sensor for detecting proximity of the optical relay structure to the sample, (5) a mask structure for selecting an effective diameter of the optical relay structure, and (6) a baffle for blocking extraneous light from entering the optical relay structure.

The invention will be understood more readily after consideration of the drawings and the detailed description of the invention that follow.

BRIEF DESCRIPTION OF THE FIGURES

FIGS. 13, 14(A–D), 15(A–D) and 16 are schematic views of sensed volumes in microplate wells.

DETAILED DESCRIPTION OF THE INVENTION

Figure 1:
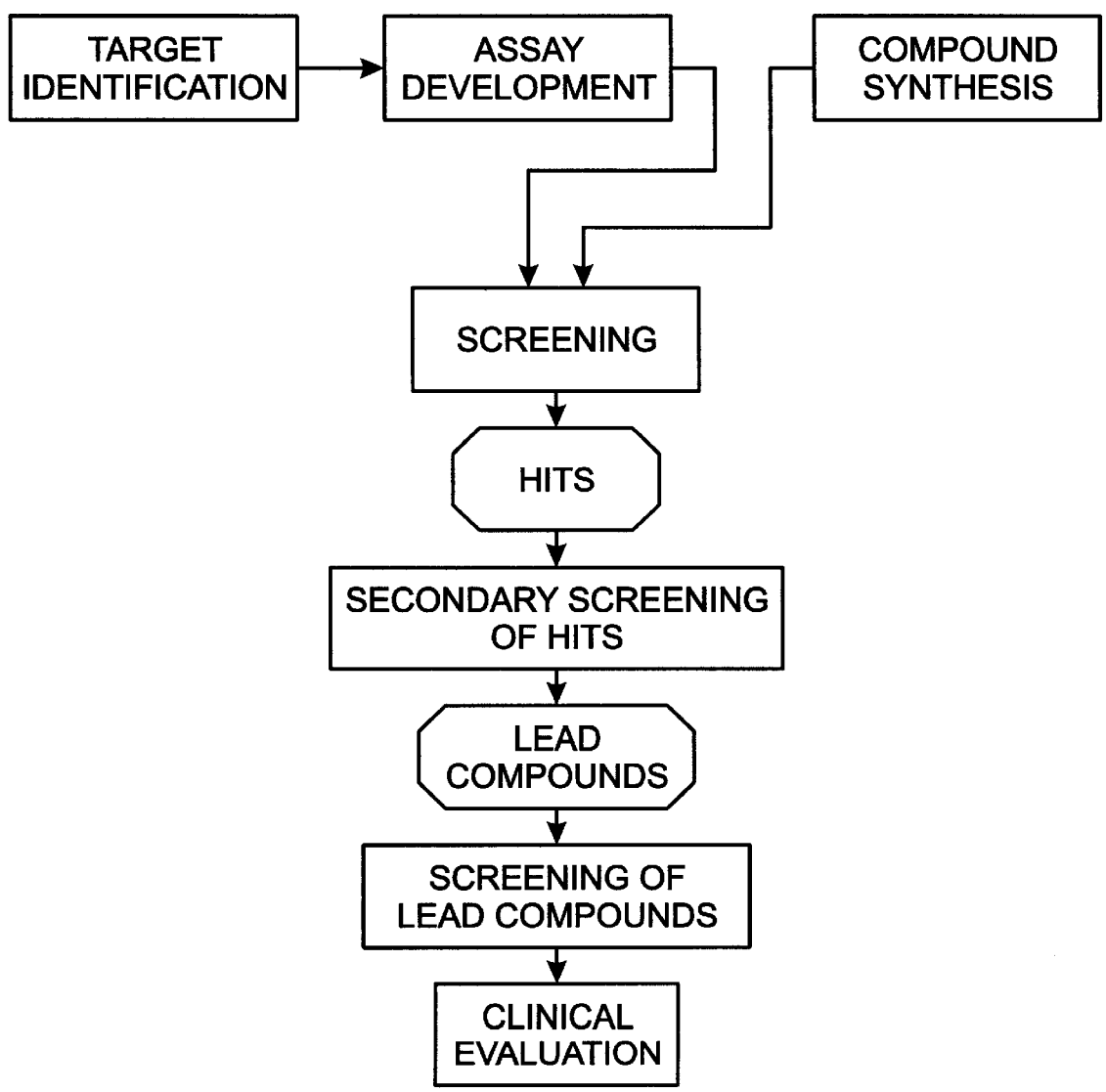
FIG. 1 is a flow chart showing elements of the drug discovery process.
Figure 2:
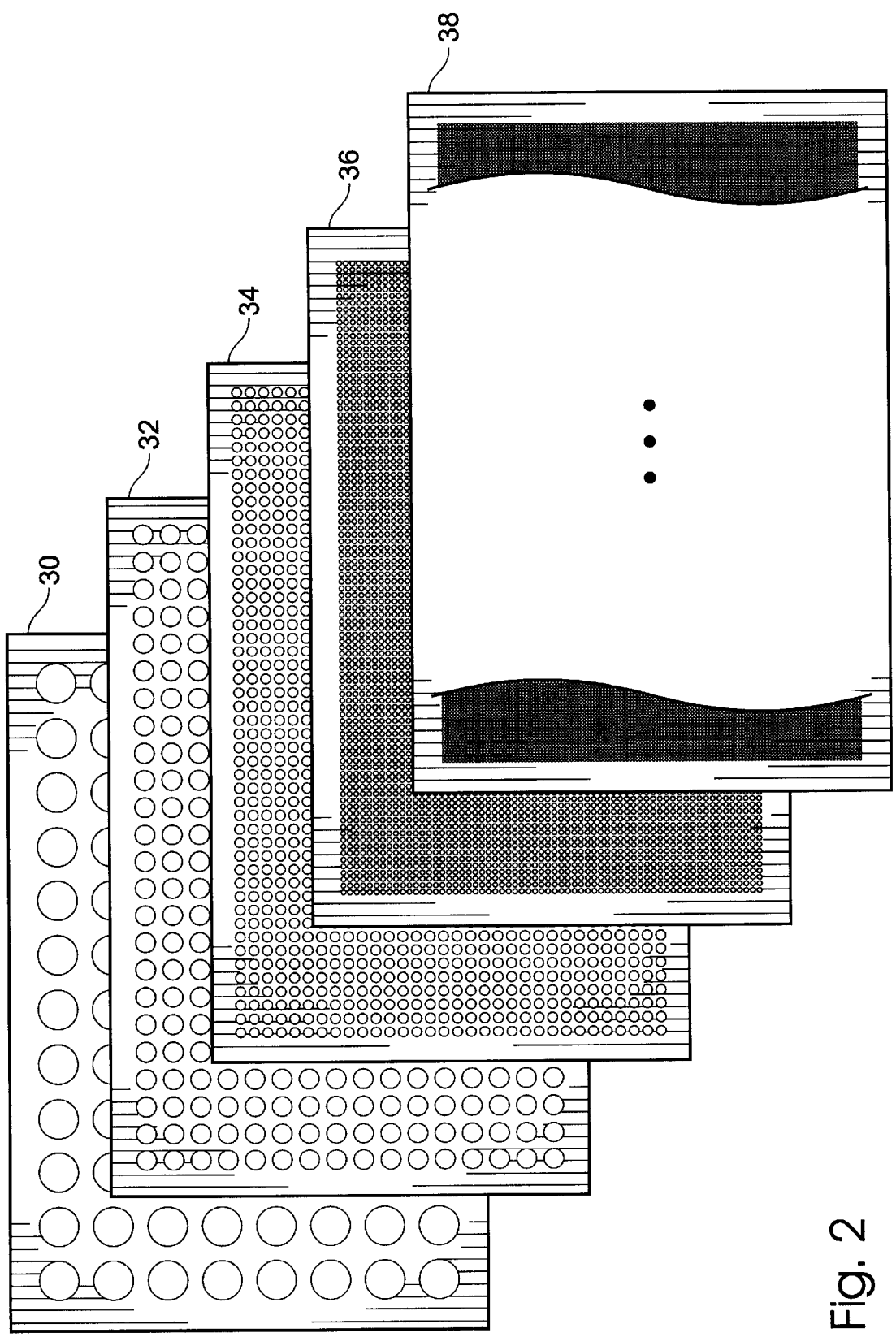
FIG. 2 is a top view of overlapping microplates showing variations in well density.

The invention provides an analyzer capable of supporting a wide range of assay formats that can be carefully selected and fine-tuned for screening desired targets with flexibility, durability, and convenience. Flexibility means that the analyzer can be used with a variety of samples and sample assays. Durability means that the analyzer can be used repeatedly, at high throughput, in laboratory and industrial settings. Convenience means that the analyzer can be used with only minimal user intervention, while also allowing assays to be run in smaller containers with reduced volumes.

The analyzer achieves these and other objectives, in part, by employing an optical system that minimizes sample interfacial boundary interference, thereby permitting reduction in assay volume in existing formats such as 96 or 384 well plates, and utilization of denser formats such as 768, 1536, 3456, or 9600 well plates. The analyzer also achieves these objective, in part, by providing the ability automatically to switch between different modes, including absorbance, photoluminescence, photoluminescence polarization, time-resolved photoluminescence, photoluminescence lifetime, and chemiluminescence modalities, among others.

The apparatus of the present invention generally includes a stage for supporting a composition in an examination site, an automated registration device for bringing successive compositions and the examination site into register for analysis of the compositions, a light source for delivering light into the compositions, a detector for receiving light transmitted from the compositions, and an optical relay structure for transmitting light substantially exclusively from a sensed volume that may comprise only a portion of the composition.

Description of the Optical System

FIGS. 3–6 show a preferred embodiment of the optical system of an analyzer 50 constructed in accordance with the present invention. The optical system generally includes at least one light source for delivering light to a composition, at least one detector for receiving light transmitted from the composition, and an optical relay structure for relaying light between the light source, composition, and detector. The optical system may limit detection to a sensed volume that may comprise only a portion of the composition.

Components of the optical system are chosen to optimize sensitivity and dynamic range for each assay mode supported by the analyzer. Toward this end, optical components with low intrinsic luminescence are chosen. In addition, some components are shared by different modes, whereas other components are unique to a particular mode. For example, photoluminescence intensity and steady-state photoluminescence polarization modes share a light source; time-resolved luminescence modes use their own light source; and chemiluminescence modes do not use a light source. Similarly, photoluminescence and chemiluminescence modes use different detectors.

These assay modes all involve detection of luminescence, which is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Separate descriptions of the photoluminescence and chemiluminescence optical systems are presented below. Selected components of both systems are described in greater detail in subsequent sections. The optical system presented here is a preferred embodiment. The present invention also includes other arrangements and components capable of detecting light from a sensed volume in high-throughput applications.

Figure 3:
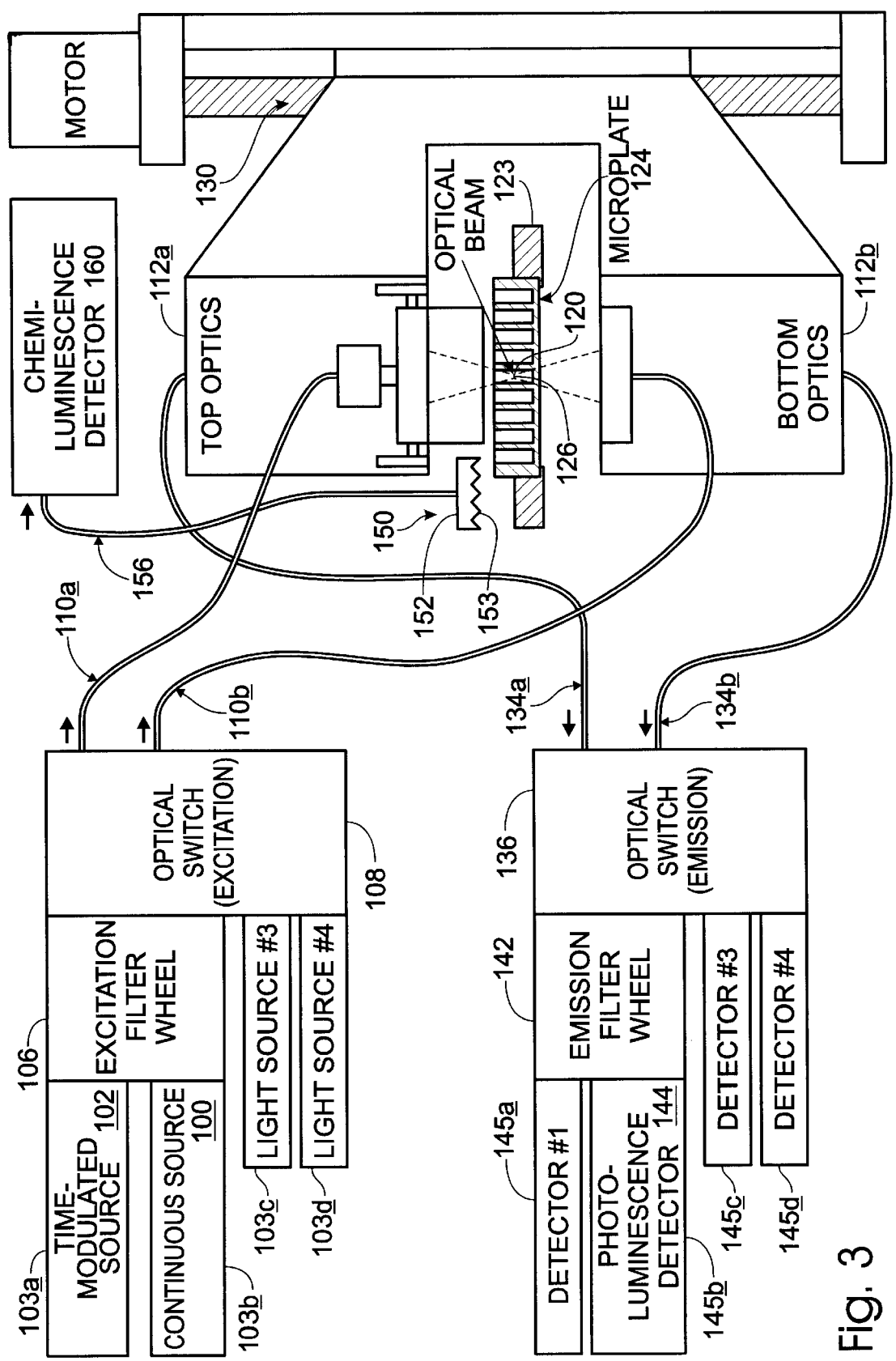
FIG. 3 is a schematic view of analyzer components employed in an embodiment of the invention.
Figure 4:
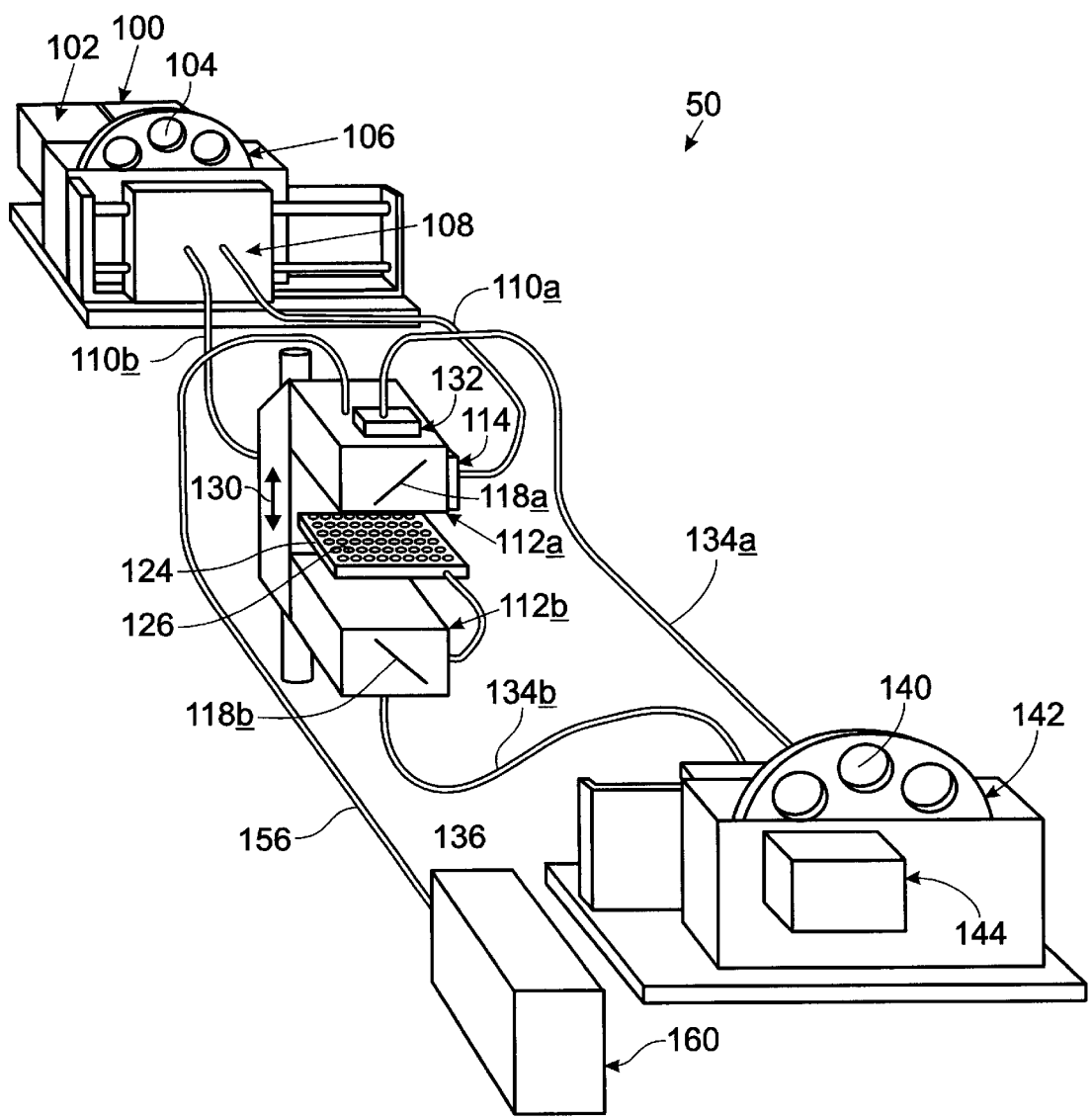
FIG. 4 is a schematic partial perspective view of analyzer components employed in an embodiment of the invention.
Figure 5:
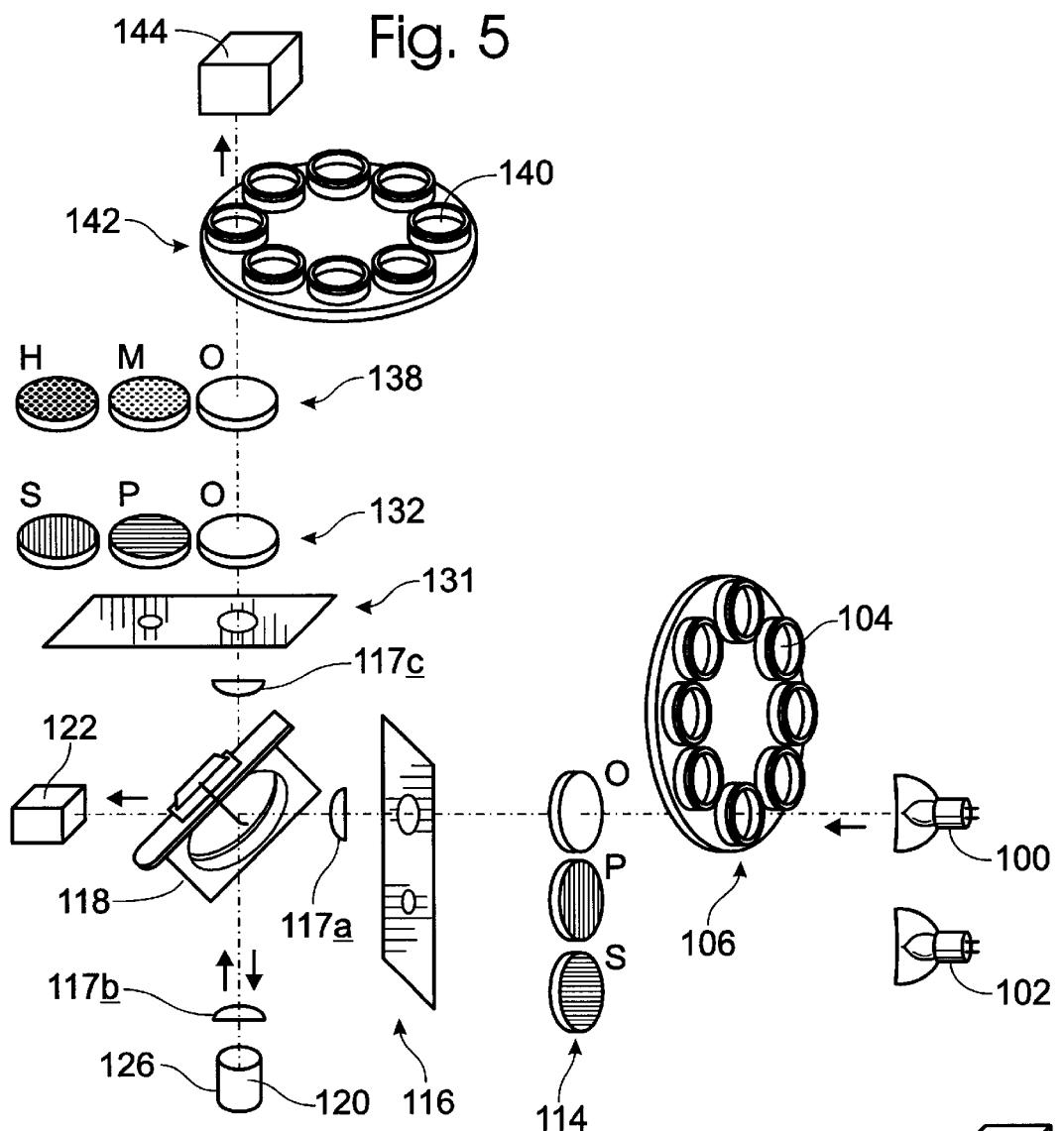
FIG. 5 is a schematic view of optical components of a luminescence optical system employed in an embodiment of the invention.

Photoluminescence optical system. FIGS. 3–5 show the photoluminescence optical system of analyzer 50. Because photoluminescence follows the absorption of light, the photoluminescence optical system must include one or more light sources. In analyzer 50, there are two light sources. A continuous source 100 provides light for photoluminescence intensity and steady-state photoluminescence polarization assays. A preferred continuous source is a high-intensity, high-color temperature xenon arc lamp. The preferred source provides more light per unit time than flash sources, increasing sensitivity and reducing read times. A time-modulated source 102 provides light for time-resolved photoluminescence assays, such as photoluminescence lifetime and time-resolved photoluminescence polarization assays. A preferred time-modulated source is a xenon flash lamp. The preferred source produces a "flash" of light for a brief interval before signal detection and is especially well suited for time-domain measurements. Other time-modulated sources include pulsed lasers, as well as continuous lamps whose intensity can be modulated extrinsically using a Pockels cell, Kerr cell, or other mechanism. The latter sources are especially well suited for frequency-domain measurements. Analyzer 50 includes light source slots 103*a–d* for four light sources, although other numbers of light source slots and light sources also could be provided. The direction of light transmission through the photoluminescence optical system is indicated by arrows.

More generally, light sources include any sources of electromagnetic radiation of any wavelength capable of inducing photoluminescence or absorption in a composition. For example, light includes but is not limited to ultraviolet, visible, and infrared radiation. Suitable light sources include lamps, electroluminescence devices, lasers, light-emitting diodes (LEDs), and particle accelerators. Depending on the source and assay mode, light produced by such light sources may be 1) mono- or multichromatic, 2) polarized or unpolarized, 3) coherent or incoherent, and/or 4) continuous or time-modulated.

In analyzer 50, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In analyzer 50, spectrum is altered by an excitation interference filter 104, which selectively transmits light of preselected wavelengths and selectively absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103*a,b*, but not other light source slots 103*c,d*.

Light next passes through an excitation optical shuttle (or switch) 108, which positions an excitation fiber optic cable 110*a,b* in front of the appropriate light source to deliver light to top or bottom optics heads 112*a,b*, respectively. The optics heads include various optics for delivering light into the sensed volume and for receiving light transmitted from the sensed volume. Light is transmitted through a fiber optic cable much like water is transmitted through a garden hose. Fiber optic cables can be used easily to turn light around corners and to route light around opaque components of the analyzer. Moreover, fiber optic cables give the light a more uniform intensity profile. A preferred fiber optic cable is a fused silicon bundle, which has low autofluorescence. Despite these advantages, light also can be delivered to the optics heads using other mechanisms, such as mirrors.

Light arriving at the optics head may pass through one or more excitation "polarization filters," which generally comprise any mechanism for altering the polarization of light. Polarization refers to the direction of the electric field associated with light. Excitation polarization filters may be included with the top and/or bottom optics head. In analyzer 50, polarization is altered by excitation polarizers 114, which are included only with top optics head 112a. Excitation polarization filters 114 may include an s-polarizer S that passes only s-polarized light, a p-polarizer P that passes only p-polarized light, and a blank O that passes substantially all light. Excitation polarizers 114 also may include a standard or ferro-electric liquid crystal display (LCD) polarization switching system. Such a system is faster and more economical than a mechanical switcher. Excitation polarizers 114 also may include a continuous mode LCD polarization rotator with synchronous detection to increase the signal-to-noise ratio in polarization assays.

Light at one or both optics heads also may pass through an excitation "confocal optics element," which generally comprises any mechanism for focusing light into a "sensed volume." In analyzer 50, the confocal optics element includes a set of lenses 117a–c and an excitation aperture 116 placed in an image plane conjugate to the sensed volume, as shown in FIG. 5. Lenses 117a,b project an image of this aperture onto the sample, so that only a preselected or sensed volume of the sample is illuminated.

Light traveling through the optics heads is reflected and transmitted through a beamsplitter 118, which delivers reflected light to a composition 120 and transmitted light to a light monitor 122. Reflected and transmitted light both pass through lens 117b, which is operatively positioned between beamsplitter 118 and composition 120. The beamsplitter is changeable, so that it may be optimized for different assay modes or compositions. The light monitor is used to correct for fluctuations in the intensity of light provided by the light sources; such corrections are performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autofluorescence.

The composition (or sample) is held in a sample container supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the compositions may involve measuring the presence, concentration, or physical properties of a photoluminescent analyte in such a composition. The sample container can include microplates, gene chips, or any array of samples in a known format. In analyzer 50, the preferred sample container is a microplate 124, which includes a plurality of microplate wells 126 for holding compositions. Composition may refer to the contents of a single microplate well, or several microplate wells, depending on the assay.

The position of the sensed volume within the composition created by the confocal optics element can be moved precisely to optimize the signal-to-noise and signal-to-background ratios. In analyzer 50, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 3 and 4. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection (1) and (4) is referred to as "epi" and is preferred for photoluminescence assays. Opposite-side illumination and detection (2) and (3) is referred to as "trans" and is preferred for absorbance assays. In analyzer 50, epi modes are supported, so the excitation and emission light travel the same path in the optics head. However, trans modes also could be supported and would be essential for absorbance assays. Generally, top optics can be used with any sample container having an open top, whereas bottom optics can be used only with sample containers having optically transparent bottoms, such as glass or thin plastic bottoms.

Light is transmitted by the composition in multiple directions. A portion of the transmitted light will follow an emission pathway to a detector. Transmitted light passes through lens 117c and may pass through an emission aperture 131 and/or an emission polarizer 132. In analyzer 50, the emission aperture is placed in an image plane conjugate to the sensed volume and transmits light substantially exclusively from this sensed volume. In analyzer 50, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts.

Excitation polarizers 114 and emission polarizers 132 may be used together in nonpolarization assays to reject certain background signals. Luminescence from the sample container and from luminescent molecules adhered to the sample container is expected to be polarized, because the rotational mobility of these molecules should be hindered. Such polarized background signals can be eliminated by "crossing" the excitation and emission polarizers, that is, setting the angle between their transmission axes at 90°. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In analyzer 50, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In analyzer 50, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters are changed by hand, although other methods also could be employed, such as a filter wheel. Intensity filters also may divert a portion of the light away from the sample without absorption. Examples include beam splitters, which transmit some light along one path and reflect other light along another path, and Pockels cells, which deflect light along different paths through diffraction.

Light next may pass through an emission interference filter 140, which may be housed in an emission filter wheel 142. In analyzer 50, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance and photoluminescence assays. In analyzer 50, there is one photoluminescence detector 144, which detects light from all photoluminescence modes. A preferred detector is a photomultiplier tube (PMT). Analyzer 50 includes detector slots 145*a–d* for four detectors, although other numbers of detector slots and detectors also could be provided.

More generally, detectors comprise any mechanism capable of converting energy from detected light into signals that may be processed by the analyzer. Suitable detectors include photomultiplier tubes, photodiodes, avalanche photodiodes, charge-coupled devices (CCDs), and intensified CCDs, among others. Depending on the detector and assay mode, such detectors may be used in (1) photon-counting or continuous modes, and (2) imaging or integrating modes.

Figure 6:
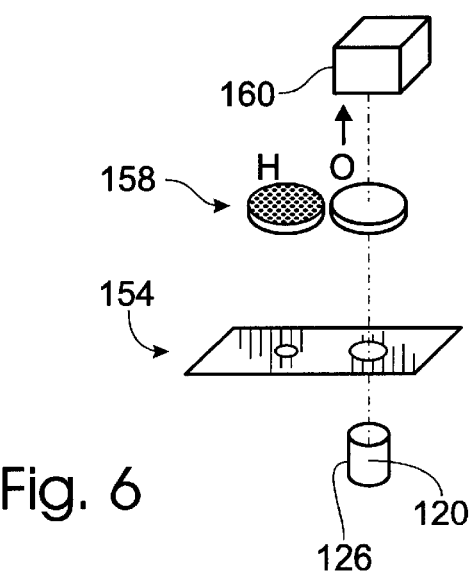
FIG. 6 is a schematic view of optical components of a chemiluminescence optical system employed in an embodiment of the invention.

Chemiluminescence optical system. FIGS. 3, 4, and 6 show the chemiluminescence optical system of analyzer 50. Because chemiluminescence follows a chemical event rather than the absorption of light, the chemiluminescence optical system does not require a light source or other excitation optical components. Instead, the chemiluminescence optical system requires only selected emission optical components. In analyzer 50, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the photoluminescence optical system. The chemiluminescence optical system also can be used for other assay modes that do not require illumination, such as electrochemiluminescence.

The chemiluminescence optical path begins with a chemiluminescent composition 120 held in a sample container 126. The composition and sample container are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample container. A portion of the light transmitted through the top of the well is collected using a chemiluminescence head 150, as shown in FIG. 3, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156. This fiber optic cable is analogous to excitation and emission fiber optic cables 110*a,b* and 134*a,b* in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In analyzer 50, intensity is altered by chemiluminescence neutral density filters 158. Light also may pass through other filters, if desired.

Light last passes to a detector, which converts light into signals that may be processed by the analyzer. In analyzer 50, there is one chemiluminescence detector 160. This detector may be selected to optimize detection of blue/green light, which is the type most often produced in chemiluminescence. A preferred detector is a photomultiplier tube, selected for high quantum efficiency and low dark count at chemiluminescence wavelengths (400–500 nanometers).

Optics Heads and the Generation of Sensed Volumes

Figure 7:
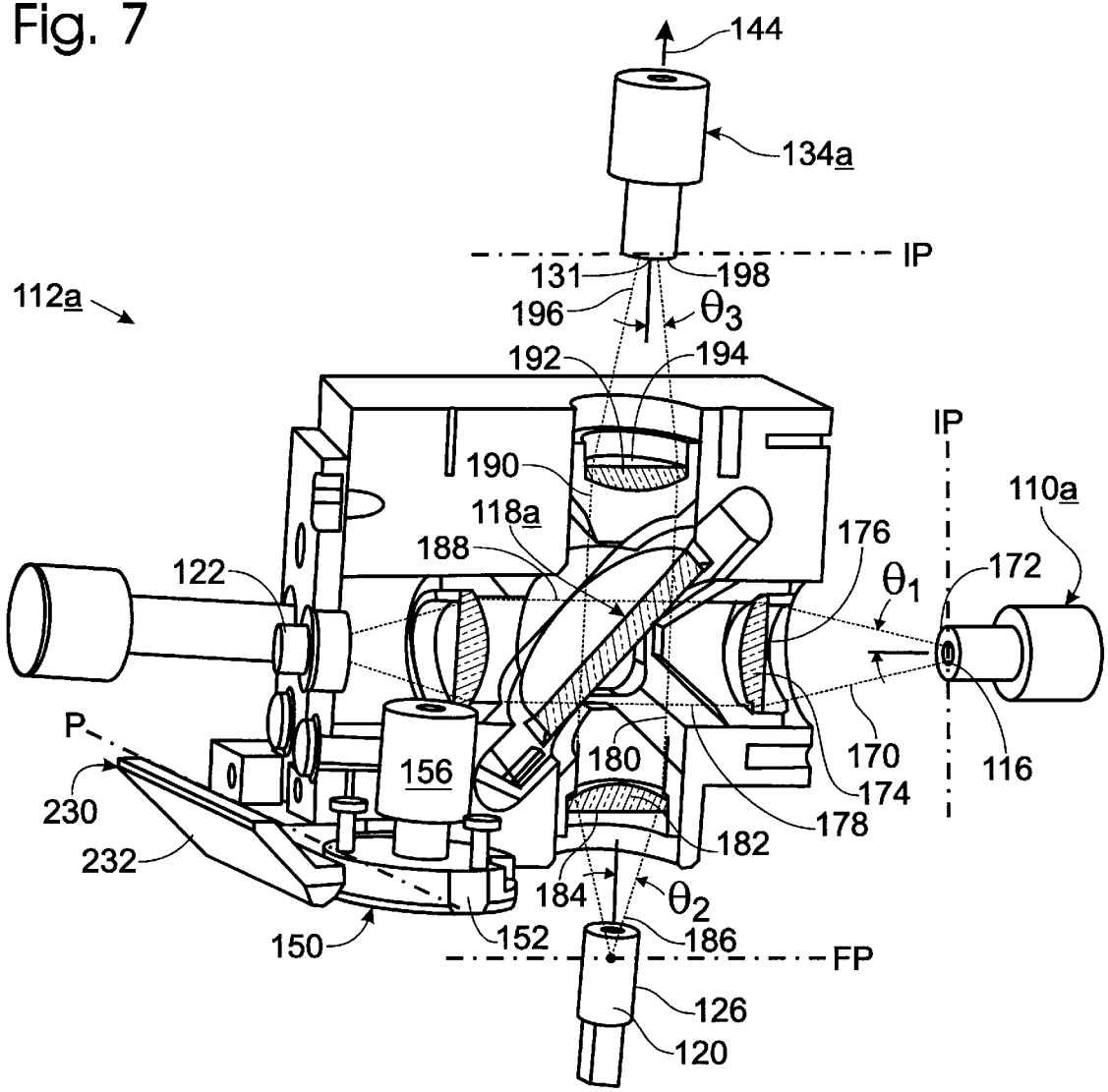
FIG. 7 is a cross-sectional perspective view of a top optics head employed in an embodiment of the invention.
Figure 11:
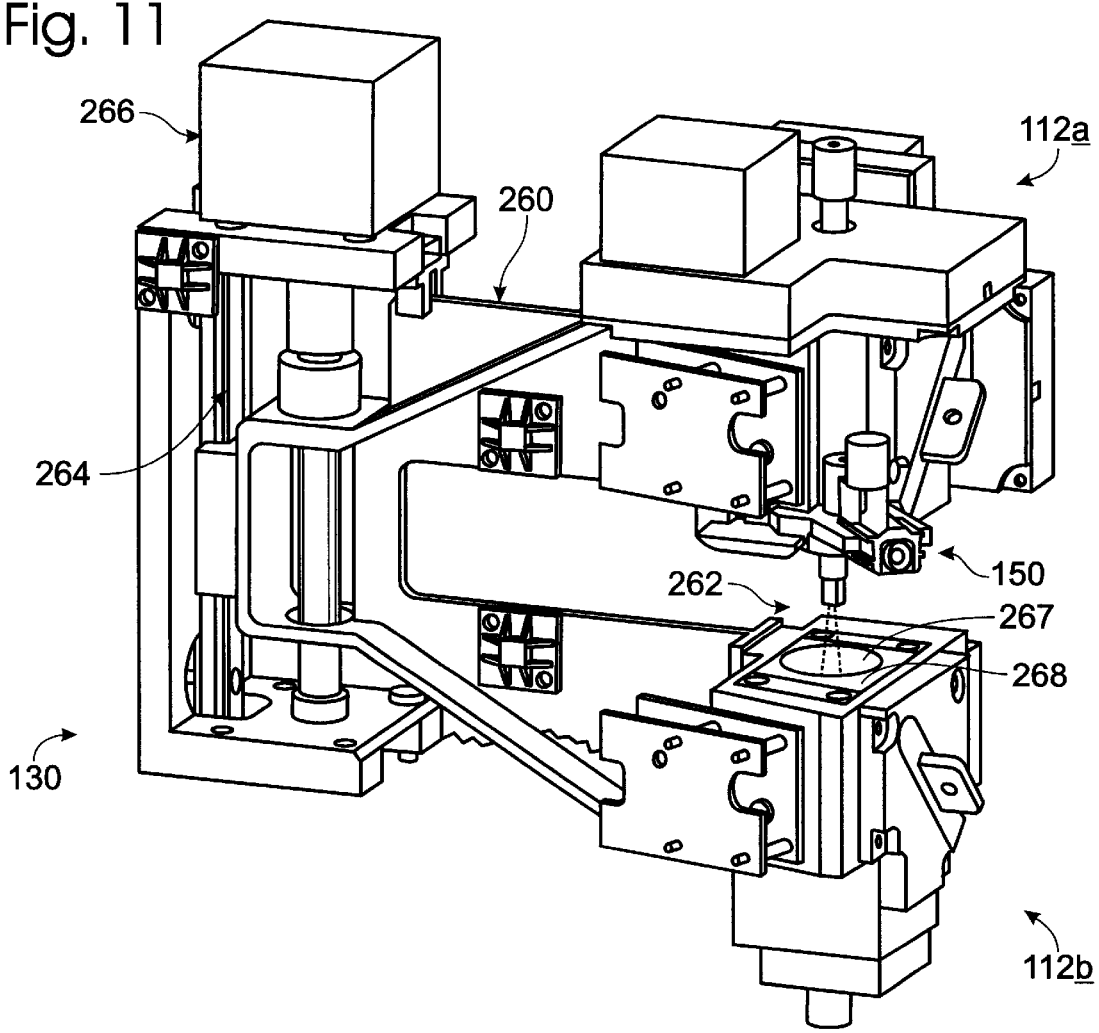
FIG. 11 is a partial perspective view of top and bottom optics heads employed in an embodiment of the invention.
Figure 12:
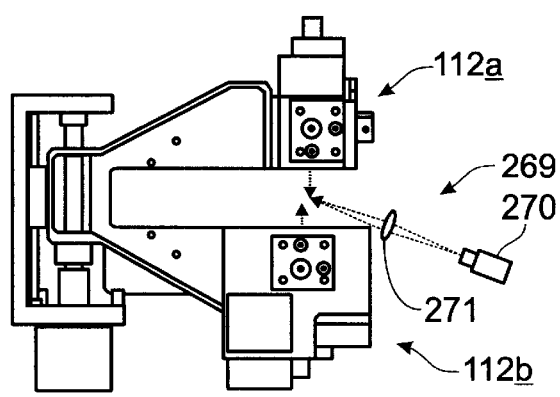
FIG. 12 is a partially schematic side elevation view of the optics assembly shown in FIG. 11, showing an offset between the top and bottom optics head and side illumination.

FIG. 7 shows a cross-sectional view of top optics head 112*a*, which is used together with fiber optic cables 110*a*, 134*a* and apertures 116, 131, as shown in FIG. 5, to create the sensed volume. Top optics head 112*a* is substantially similar to bottom optics head 112*b*, as shown in FIGS. 11 and 12, except that top optics head 112*a* includes chemiluminescence head 150 and excitation and emission polarizers 114, 132 (not shown), and that bottom optics head 112*b* includes a window and drip lip (described below).

Excitation light arrives at top optics head 112*a* through excitation fiber optic cable 110*a*. Fiber optic cables are cylindrical waveguides that transmit light through a process known as total internal reflection. Fiber optic cables are characterized by a numerical aperture, which describes the maximum angle through which the fiber optic cable can collect light for total internal reflection. The higher the numerical aperture, the greater the angle over which the fiber optic cable can collect and transmit light. The numerical aperture is defined as NA=n sin θ, where NA is the numerical aperture, n is the index of refraction of the medium adjacent the fiber optic cable, and θ is the half angle of the cone of transmitted or incident light. In top optics head 112a, the medium adjacent the fiber optic cable is air, so n≅1.

Excitation light exits fiber optic cable 110a through excitation aperture 116 at a cone angle $\theta_1$ determined in part by the numerical aperture of the fiber optic cable. In top optics head 112a, exiting excitation light forms a first cone 170 of excitation light, with its apex positioned just inside the tip 172 of fiber optic cable 110a. First cone 170 of excitation light passes through an excitation polarizer 114 (not shown), and then through a first plano-convex converging lens 174, whose plan side 176 is oriented toward fiber optic cable 110a. First lens 174 is positioned so that it substantially converts first cone 170 of excitation light into a first cylinder 178 of excitation light. This conversion is accomplished by positioning tip 172 substantially at the focal point of first lens 174.

First cylinder 178 of excitation light impinges on beamsplitter 118a. Beamsplitter 118a reflects a reflected cylinder portion 180 of excitation light toward composition 120 in sample well 126. Reflected cylinder portion 180 passes through a second plano-convex converging lens 182, whose plan side 184 is oriented away from beamsplitter 118a. Second lens 182 converts reflected cylinder portion 180 of excitation light into a second cone 186 of excitation light, which is focused onto and thus delivered to composition 120 in sample well 126. The cone angle $\theta_2$ of second cone 186 is determined in part by the numerical aperture of second lens 182, and may be different from the cone angle $\theta_1$ describing excitation light exiting fiber optic cable 110a.

Beamsplitter 118a also transmits a transmitted cylinder portion 188 of the excitation light to light monitor 122, which functions as described above. The optics used to focus the transmitted light into the light monitor may be substantially similar to the optics used to focus the reflected light into the sample well. Alternatively, the optics may include a lensless system, such as a black tapered cone to direct light.

The excitation light may induce photoluminescence within the composition. Photoluminescence (or emission) light has longer wavelengths than the associated excitation light. This is due to conservation of energy; in photoluminescence, the emission light has lower energy (and so longer wavelength) than the excitation light, because some of the energy of the excitation light is lost nonradiatively.

A conical portion of the emission light substantially coextensive with second cone 186 of excitation light passes back through second lens 182, which converts the conical portion into a cylindrical portion of emission light substantially coextensive with reflected cylinder 180 of excitation light.

Emission light next impinges on beamsplitter 118a, which transmits a cylinder portion 190 of emission light toward photoluminescence detector 144. Beamsplitter 118a typically is chosen to accommodate one of two different scenarios. If a large number or variety of luminescent molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable emission light to the detector. If one or a few related luminescent molecules are to be studied, the beamsplitter needs only to be able to accommodate light at a limited number of wavelengths; in this case, a "dichroic" or "multichroic" beamsplitter is optimal. Such a beamsplitter can be designed for the appropriate set of molecules and will reflect most or substantially all of the excitation light, while transmitting most or substantially all of the emission light. This is possible because the reflectivity and transmissivity of the beamsplitter can be varied with wavelength.

Cylinder portion 190 of emission light transmitted through beamsplitter 118a passes through a third plano-convex converging lens 192, whose plan side 194 is oriented away from the beamsplitter. In first optics head 112a, emission light first may pass through an emission polarizer 132, as shown in FIG. 5. Third lens 192 focuses the cylindrical portion 190 of emission light into a third cone of light 196 that impinges on emission fiber optic cable 134a for transmission to photoluminescence detector 144. To be transmitted by the fiber, the light should be focused onto emission aperture 131 at the tip 198 of the fiber as a spot comparable in size to the diameter of the fiber optic cable. Moreover, the incident cone angle $\theta_3$ should not exceed the inverse sine of the numerical aperture of the fiber.

A property of the optical arrangement in top optics head 112a is that the tips 172, 198 of fiber optic cables 110a, 134a and the sensed volume of the composition are "confocal." Confocal means that all three objects are in conjugate focal planes, so that whenever one is in focus, all are in focus. The sensed volume of the composition lies in a focal or sample plane FP of the system, and the tips of the fiber optic cables lie in image planes IP of the system. The detector also may be placed in an image plane, so that it detects the composition in focus. The tips of the fiber optic cables may be said to lie in intermediate image planes, because light passes through these planes, and the detector may be said to lie in a terminal image plane, because light terminates on the detector.

The sensed volume is created by placing confocal optics elements in or near one or more intermediate image planes. A preferred confocal optics element is an aperture. If such an aperture is placed in the excitation optical path, an image of the aperture will be focused onto the composition. As a result, only a portion of the composition within the focal plane corresponding to the shape and proportional to the size of the aperture will be illuminated, and only luminescent molecules in or near that portion of the focal plane will be induced to emit photoluminescence. If such an aperture is placed in the emission optical path, an image of the aperture will be focused onto the detector. Luminescence that ordinarily would focus onto a part of the detector outside the image of the aperture will be blocked or masked from reaching the detector.

The "shape" (or intensity profile) of the sensed volume depends on the confocal optics elements, such as excitation and emission apertures 116, 131, the light source, and the numerical apertures of the lenses and fiber optic cables. Generally, the intensity of the light incident on (or emitted from) the sensed volume will be greatest at the center of the sensed volume, and will decay monotonically in all directions away from the center. Most of the intensity will lie within a distance equal to about one aperture diameter from the center of the sensed volume in the Z direction, and within about one-half an aperture diameter from the center of the sensed volume in the X and Y directions.

FIG. 7 also shows a sample container sensor switch 230, which is used to prevent damage to optics head 112a by preventing the optics head from physically contacting a sample container. Sample container sensor switch 230 is mounted about a pivot axis P adjacent chemiluminescence head 150. Sample container sensor switch 230 includes a sensor surface 232 positioned so that a sample container must contact the sensor surface before contacting any component of top optics head 112a. Contact between a sample container and sensor surface 232 causes sample container sensor switch 230 to pivot about pivot axis P, activating an electrical circuit that turns off power to the mechanism(s) used to move the sample container.

A sample container sensor switch is especially important in an analyzer designed for use with a variety of sample containers, because it reduces the likelihood of damage both from exotic sample holders with unusual dimensions and from standard sample holders with aberrant or misidentified dimensions. The sample container sensor switch may detect impending contact between the sample container and optics head (1) mechanically, as in the preferred embodiment, (2) optically, as with an electric eye, (3) acoustically, as with an ultrasonic detector, or (4) by other mechanisms. For example, the sample container sensor switch may include a linear voltage displacement transducer (LVDT), which measures displacement by creating a voltage proportional to the displacement.

FIG. 7 also shows a chemiluminescence head 150, which includes a chemiluminescence baffle 152 and a chemiluminescence fiber optic cable 156. Chemiluminescence head 150 is mounted on top optics head 112a, but also could be mounted on bottom optics head 112b or on both top and bottom optics heads 112a,b.

Figure 8:
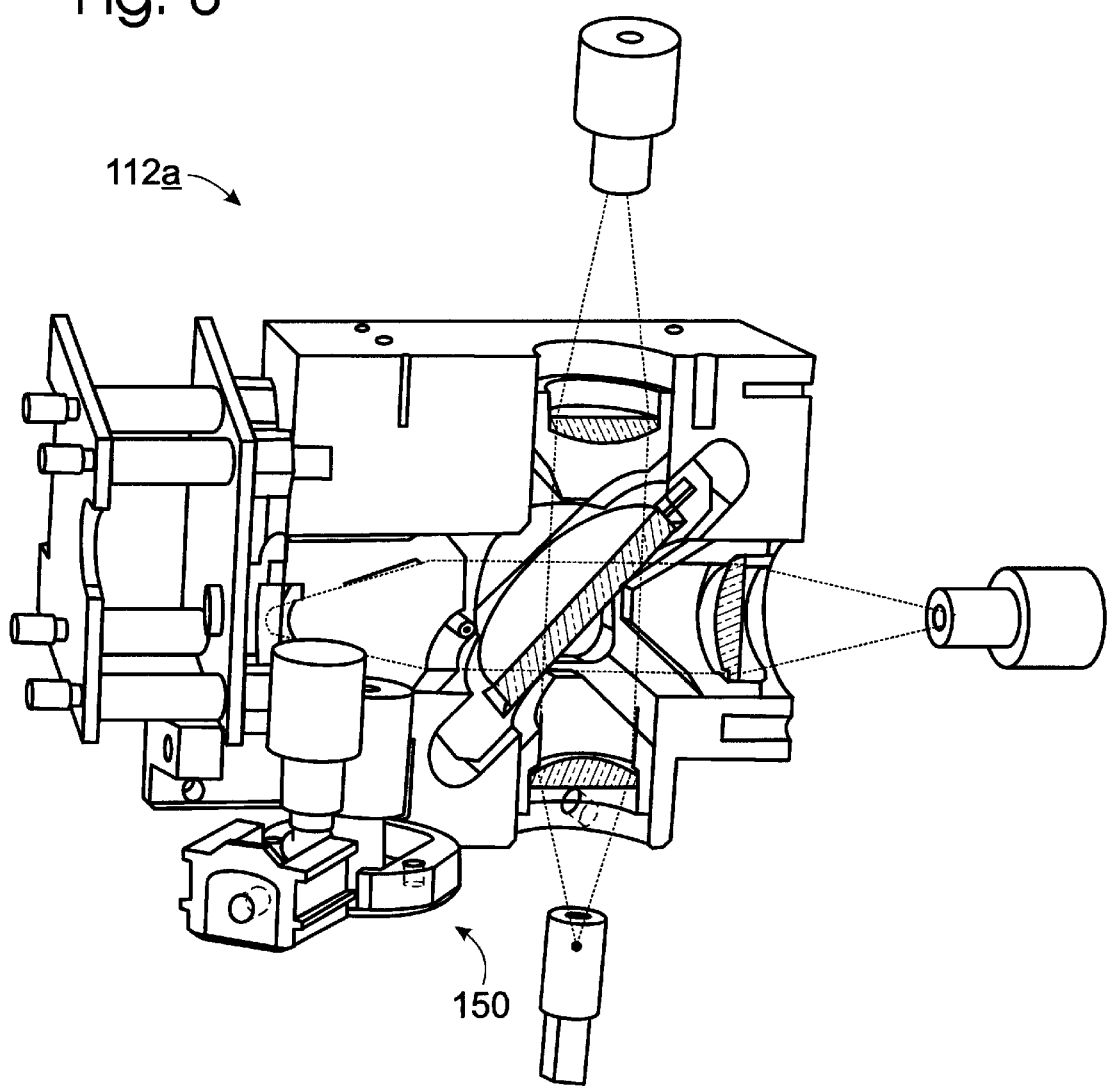
FIG. 8 is a cross-sectional perspective view of an alternative top optics head employed in an embodiment of the invention.

FIG. 8 shows an alternative embodiment of top optics head 112a, which includes an alternative embodiment of chemiluminescence head 150.

Figure 9:
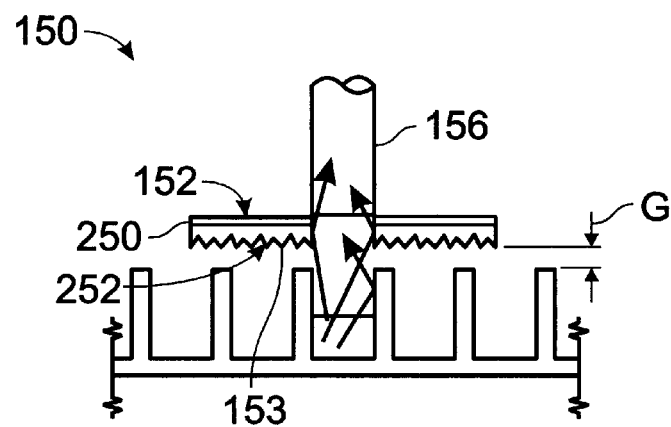
FIG. 9 is a partially schematic cross-sectional view of a chemiluminescence head employed in an embodiment of the invention.

FIG. 9 shows an alternative view of chemiluminescence head 150. In chemiluminescence, emission light sensitivity is maximized by detecting as much emission light as possible from the top of the sample container. In analyzer 50, this is accomplished by placing fiber optic cable 156 directly above and aligned with the center of the microplate well or other sample container. A high numerical aperture fiber optic cable may be used to collect most or substantially all of the light emitted from the composition. A preferred fiber optic cable has a numerical aperture of 0.22 and is formed of silica for low autoluminescence.

Detection of chemiluminescence light further is enhanced by positioning fiber optic cable 156 so that the gap G or flying height between the fiber optic cable and the top of the sample container is as small as possible. Generally, if the gap between the top of the microplate and the fiber optic cable is small compared to the diameter of the fiber optic cable, most of the emission light will be collected. In analyzer 50, preferred values of G lie in the range 0.25–1.5 mm, depending on the type of microplate. The preferred values allow for normal variations in microplate thickness and minimize the possibility of contacting liquid that may be on the surface of the microplate. This is accomplished by accurate calibration of the travel of the optical head along the Z-axis relative to a reference point on the Z-axis. The height of various microplates can be stored in software so that G can be set by the instrument to a preselected value.

Gap G also can be determined empirically using a precision top-of-plate sensor, which is mounted on the bottom of the upper optics head. The height of the plate is measured by slowly moving the optics head toward the plate until the top-of-plate sensor indicates that a known flying height has been achieved. With this approach, the height of the plate need not be known in advance. Moreover, if a microplate mistakenly is inserted into the machine with a greater than expected height, the top-of-plate sensor can be used to prevent the optics head from colliding with the microplate.

Chemiluminescence head 150 also includes a chemiluminescence baffle 152, which supports fiber optic cable 156 and an aperture support slide 250 and which also minimizes detection of ambient light and chemiluminescence from neighboring wells. Detection from neighboring wells may be referred to as "cross talk." In analyzer 50, chemiluminescence baffle 152 is generally circular and includes a black surface 252 with rugosities 153 designed to absorb light. Chemiluminescence baffle 152 may have a diameter at least about twice the diameter of the fiber optic cable, and may be configured to allow low cross talk to be achieved at comfortable flying heights.

Figure 10:
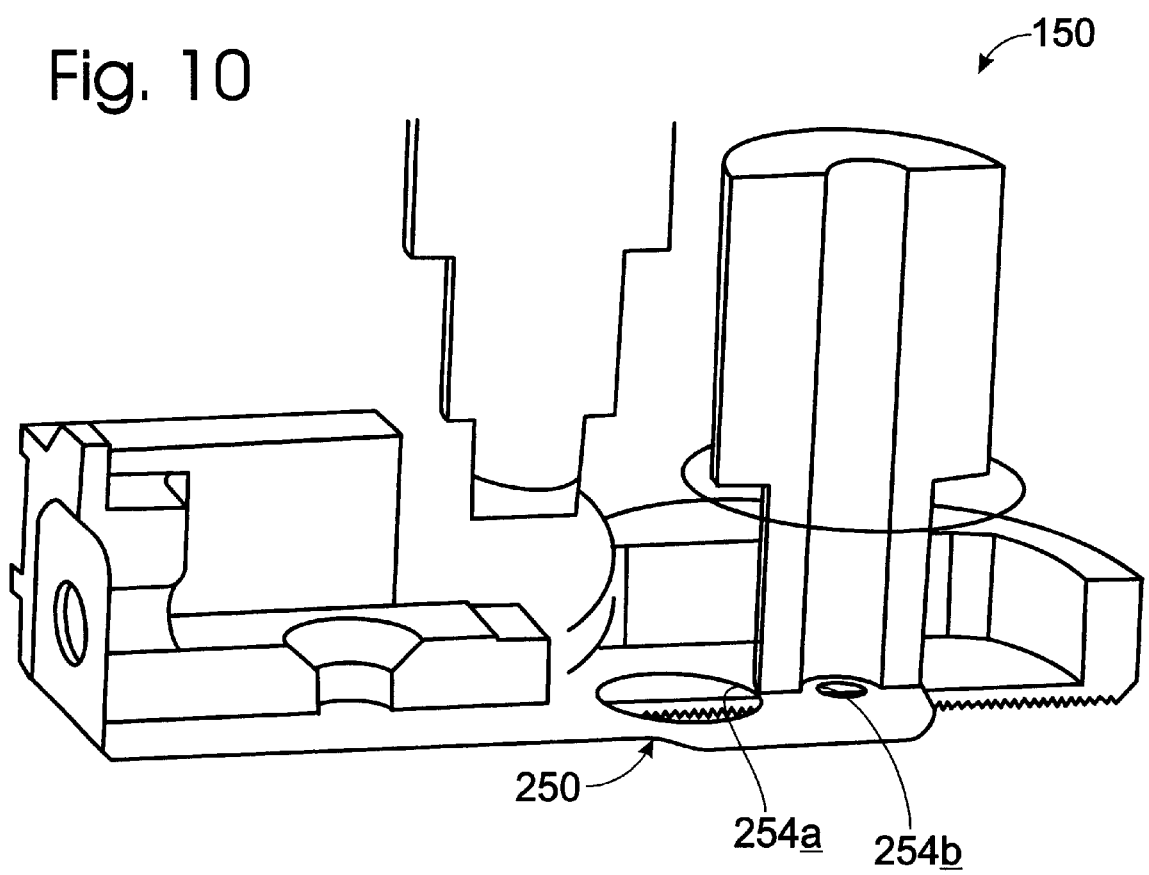
FIG. 10 is a cross-sectional perspective view of a portion of the chemiluminescence head shown in FIG. 8.

FIG. 10 shows a partially cross-sectional perspective view of chemiluminescence head 150. Chemiluminescence head 150 includes a fiber optic cable 156 and an aperture support plate 250 containing apertures 254a,b that determine an "effective" entrance diameter for the fiber optic cable. In turn, the effective entrance diameter for the fiber optic cable determines the size of the sensed volume within the sample. To maximize signal, apertures 254a,b generally are chosen substantially to equal the diameter of the microplate well. Large apertures 254a having diameters larger than fiber optic cable 156, and small apertures 254b having diameters smaller than fiber optic cable 156 may be placed in front of the fiber optic cable. A moveable aperture support slide 250 may include separate apertures for 96, 384, 768, 1536, 3456, and 9600 well plates, among others, where each aperture is optimized for the well size associated with a particular microplate. Alternatively, a fixed aperture support slide 250 may include a continuous iris diaphragm aperture, where the size of the continuous diaphragm may be optimized for a range of well sizes.

Alternative embodiments of the chemiluminescence optical system could include a plurality of chemiluminescence heads optically connected to a plurality of chemiluminescence detectors. The chemiluminescence heads could be mounted as a linear array or as a matrix. For example, a linear array of 8 or 12 chemiluminescence heads optically connected to 8 or 12 detectors could be used to detect simultaneously from entire rows or columns of a 96-well microplate. Moreover, the same arrays also could be used with the appropriate apertures to detect from higher-density plates in which the well-to-well spacing is evenly divisible into the well-to-well spacing in the 96-well plate, as for 384 and 1536-well plates. The chemiluminescence heads also could be mounted as a matrix that could detect from one or more plate formats.

Other alternative embodiments of the chemiluminescence optical system could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

These alternative embodiments may be used with alternative embodiments of chemiluminescence baffle 152. For example, with a fiber optic bundle, cross-talk between wells within the matrix can be minimized by keeping G as small as possible and/or by applying an anti-reflective coating to the face of the fiber bundle. An anti-reflective coating can reduce reflected light from about 4% to less than 1%. In addition, a baffle having a rough black surface as described above could be placed around the outside of the fiber bundle, like a collar, to minimize pick-up from areas of the plate that are not under the bundle.

FIG. 11 shows the relationship between top and bottom optics heads 112a,b and chemiluminescence head 150. Top and bottom optics heads 112a,b are coupled to an optics head support structure 260, which includes a gap 262 through which a stage and sample container can pass. Optics head support structure 260 is configured so that the relative positions of top and bottom optics heads 112a,b are fixed.

FIG. 11 also shows a Z-axis adjustment mechanism 130, which is used to adjust the position of a sensed volume within a composition. Z-axis adjustment mechanism 130 includes a support track 264 that is substantially parallel to a Z-axis on which optics head support structure 260 is mounted. Z-axis adjustment mechanism 130 also includes a motor 266 for moving optics head support structure 260 along support track 264. The position of a sensed volume within a composition positioned in gap 262 is adjusted by moving top and bottom optics heads 112a,b relative to the composition. Movement relative to the composition may be effected by moving the optics heads while keeping the composition stationary, as here, or by moving the composition while keeping the optics heads stationary, among other mechanisms.

FIG. 11 also shows aspects of bottom optics head 112b. Generally, bottom optics head 112b resembles top optics head 112a. However, bottom optics head 112b includes a window 267 and an elevated drip lip 268 that are not included on top optics head 112a. Window 267 and drip lip 268 prevent fluid dripped from a microplate from entering bottom optics head 112b. Fluid dripped from a microplate is a concern with bottom optics head 112b because the bottom optics head is positioned below the microplate during analysis.

FIGS. 11 and 12 show further aspects of bottom optics head 112b. Generally, light is directed through bottom optics head 112b much like light is directed through top optics head 112a. However, light also may be directed by an alternative optical relay structure 269 to the bottom (or top) optics head. Alternative optical relay structure 269 may include a fiber optic cable 270 and focusing lens structure 271. Off-axis illumination eliminates loss of light due to absorption and reflection from the beam splitter and substantially eliminates reflection of incident light into the detection optics, reducing background. Off-axis illumination also may be used for total internal reflection illumination.

FIGS. 11 and 12 also show the relative positions of top and bottom optics heads 112a,b. Top and bottom optics heads 112a,b may be aligned, so that excitation light transmitted by one optics head can be detected by the other optics head, facilitating absorbance assays. A shutter may be positioned between the two optics heads to prevent light from one optics head from entering and exciting fluorescence from the other optics head during luminescence assays. Alternatively, top and bottom optics head 112a,b may be offset, so that light from one optics head cannot enter the other optics head. A small optical relay structure, such as a fiber optic cable, may be positioned adjacent or as part of bottom optics head 112b to detect light in a top illumination and bottom detection mode.

Application of Sensed Volumes

The optical system described above, and the confocal optics elements in particular, allow detection of luminescence substantially exclusively from a sensed volume of a composition.

Figure 13:
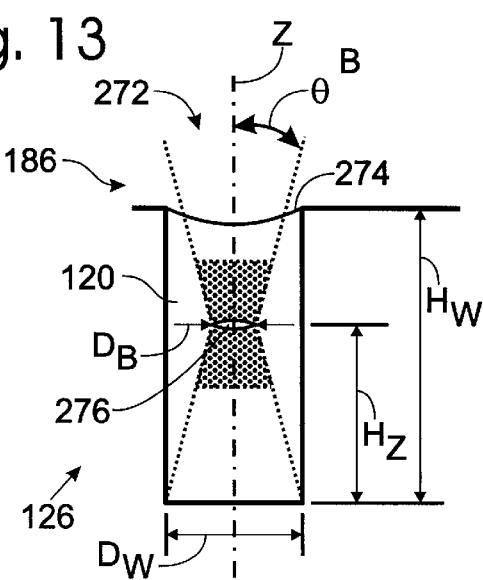

FIG. 13 shows a standard microplate well 126 and an excitation light beam 186 as it illuminates the well. The standard well is cylindrical and may be characterized by a diameter $D_W$ and a height $H_W$. Other wells may have other geometries and be characterized by other quantities; for example, a well could be square and characterized by a width and a height, or a well could be conical and characterized by a cone angle and a height. The interface between composition 120 and the air 272 is termed the meniscus 274 and may be convex, plan, or concave.

Excitation light beam 186 is focused by the optical system so that it is shaped much like an hourglass along the optical (Z) axis. This hourglass shape arises as the cone of excitation light formed by the optics passes through focus. The diameter $D_B$ of the beam is smallest at the beam's waist 276, which corresponds to the focal plane, above and below which the beam diverges monotonically, making an angle $\theta_B$ with respect to the vertical or Z-axis. Values of $D_B$ and $\theta_B$ depend on optical components of the analyzer and may be varied by changing these components. Generally, $D_B$ and $\theta_B$ are inversely related. The distance between the bottom of the well and the beam waist is termed the focal (Z) height, $H_2$.

The shape of the sensed volume, indicated by stippling, may differ in directions parallel and perpendicular to the optical or Z-axis. Parallel to the Z-axis, the shape may be Lorentzian, among others. Perpendicular to the Z-axis, the shape may be Gaussian, or it may be a rounded pulse function, among others. A laser beam might give rise to a Gaussian, whereas a fiber optic bundle might give rise to a rounded pulse function. Generally, lower numerical apertures will create sensed volumes shaped more like cylinders, whereas higher numerical apertures will create sensed volumes shaped more like hourglasses.

The shape and volume of the sensed volume may be adapted like a probe to match the shape and volume of the sample container. Thus, the sensed volume may be expanded for maximum signal in a large sample container, and contracted to avoid nearby walls in a small sample container. The shape and volume of the sample container also may be chosen or designed to conform to the shape and volume of the sensed volume.

Alternatively, the sensed volume may be held constant. In this way, the sensed volume will report on equal volumes of each composition analyzed, so that the analyzer effectively reports "intensive" quantities. Intensive quantities do not depend on the amount of composition in a sample container; in contrast, extensive quantities do depend on the amount of composition in the sample container. This approach can be used to facilitate comparison of results obtained from different-sized sample wells, such as in 96 and 384 well microplates. Alternatively, this approach can be used to facilitate comparison of results obtained from like-sized sample wells containing different volumes of solution, as by design or by error.

FIG. 14 shows how the signal-to-noise and signal-to-background ratios are affected by focal height for two assay modes. In homogeneous assays (Panel B), photoluminescent molecules are distributed uniformly throughout the composition, and the optimum signal-to-noise and signal-to-background ratios are obtained regardless of well geometry when the sensed volume is positioned in the middle of the composition (Panel A), so that the sensed volume does not overlap with the meniscus or the bottom or sides of the well. If the meniscus is in the sensed volume, light reflected from the meniscus will be detected. This will decrease sensitivity by increasing background and decreasing signal.

If the bottom of the well is in the sensed volume, light reflected from the well bottom will be detected. Moreover, noncomposition photoluminescence arising from fluorescent and other photoluminescent materials that are commonly included in the microplate or adsorbed to the walls of the microplate also will be detected. These two effects will decrease sensitivity by increasing background and decreasing signal. Luminescence measured from the microplate walls will lead to spuriously high luminescence intensities and luminescence polarizations.

In cell-based assays (Panels C and D), photoluminescent molecules are concentrated in or near cells growing at the bottom of the well, and the optimum signal-to-noise and signal-to-background ratios are obtained when the sensed-volume is centered about the bottom of the well (Panel A). Such centering may be accomplished either using top optics (Panel C) or bottom optics (Panel D).

The shape and position of the sensed volume within the well are affected by (1) the meniscus, (2) the geometry of the microplate well, and (3) the geometry of the whole microplate.

FIG. 15 shows how the meniscus affects the shape and position of the sensed volume. When there is no fluid and hence no meniscus, the beam has a nominal undistorted shape; see Panel A. The meniscus affects the sensed volume because light is refracted as it crosses the meniscus boundary between the air and the composition. Specifically, light passing from air (with its lower index of refraction) to the composition (with its higher index of refraction) bends toward the normal, as described by Snell's law. Here, the normal is the direction perpendicular to the surface of the meniscus at a given point. If the meniscus is everywhere perpendicular to the light beam, then light passing through the meniscus will not bend, and the beam will retain its nominal undistorted shape. For a converging beam, this will occur when the meniscus is appropriately convex; see Panel B. If the meniscus is more than appropriately convex, light will bend toward the middle of the well as it passes through the meniscus, and the sensed volume will be compressed and raised; see Panel C. If the meniscus is less than appropriately convex, flat, or concave, light will bend away from the middle of the well as it passes through the meniscus, and the sensed volume will be stretched and lowered; see Panel D. Meniscus effects could be minimized by appropriately configuring microplate wells.

Figure 16:
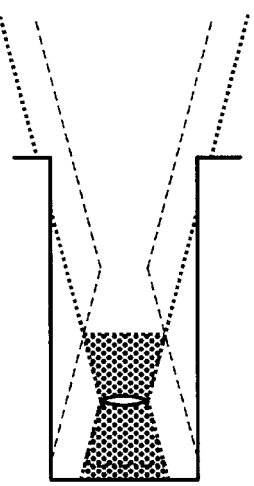
Figure 17:
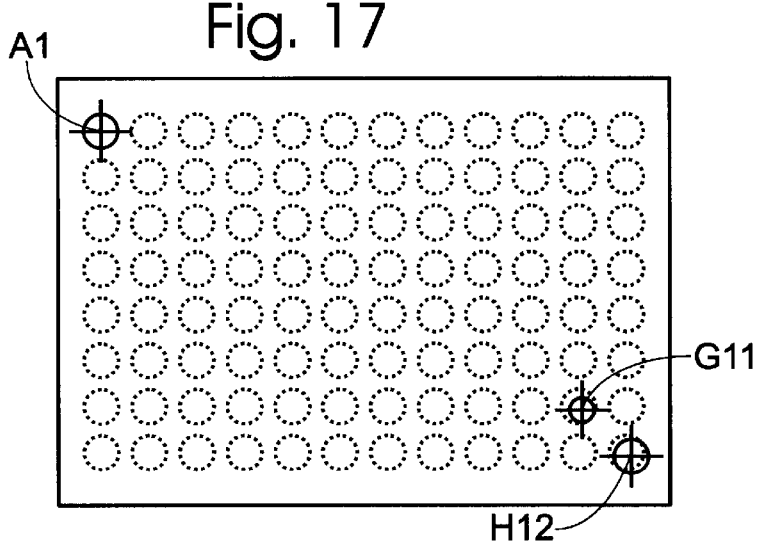
FIG. 17 is a schematic top view of a microplate.

FIGS. 16 and 17 show how the geometry of the microplate well affects the position of the sensed volume. In particular, if the well is sufficiently narrow relative to the diameter of the beam or if the well is sufficiently deep relative to the angle made by the beam, then the light beam may impinge upon the top walls of the well. In these cases, setting the Z-height too low can reduce sensitivity (1) by decreasing the desired signal because less light enters the well, and (2) by increasing the background because the light beam illuminates the tops of wells. Many microplates are made from materials that are fluorescent or otherwise photoluminescent, and the instrument will detect this photoluminescence from materials at the tops of wells.

FIG. 17 shows how the geometry of the microplate affects the position of the sensed volume. The analyzer is configured automatically to find the location of each well in a given microplate, beginning with well A1. The analyzer does this using stored parameters describing the dimensions (plate heights, interwell distances, etc.) of the particular microplate style. However, these microplate parameters are nominal values and do not account for unit-to-unit or lot-to-lot variations in microplate geometry. If there is a slight variation in interwell distance, the light beam can be off-center on some wells even though it is perfectly centered on well A1. This effect is termed cross-plate drift.

Cross-plate drift of fluorescence readings may increase as the instrument scans across the microplate as variations are compounded. Typically, drift will be worst at well H12, which is farthest from well A1. Such drift can be reduced by making the stage more accurate, by making the sample containers of a more consistent size, or by increasing $H_Z$, which will reduce the diameter of the beam and put it back into the well. The lattermost approach is shown for well G11.

Figure 18:
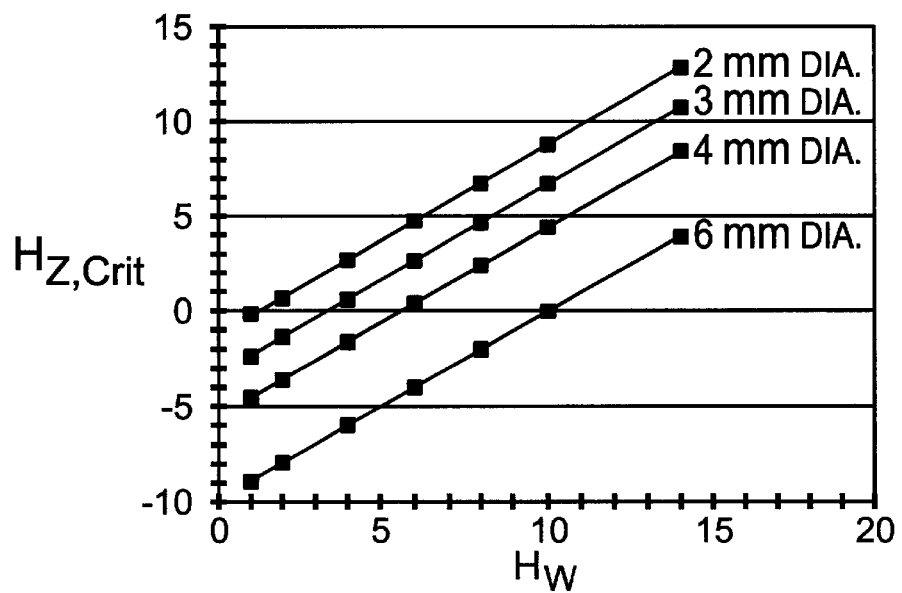
FIG. 18 is a graph showing the relationships between critical Z-height and microplate well height.

Because beam position is a critical determinant of signal to noise, Z height must be appropriately maintained; Z height should be kept above a critical focal height, $H_{Z,Crit}$. The height at which the beam first impinges on the walls of the well is the critical focal height, $H_{Z,Crit}$. FIG. 18 shows how $H_{Z,Crit}$ depends on the well height $H_W$ and well diameter $D_W$, for a beam of diameter 1.5 millimeters (mm) and a beam angle $\theta_B$ of 12.7 degrees. Similarly, Table 1 shows how $H_{Z,Crit}$ depends on well height and well diameter for four commercially available microplates.

| Plate Type | Well Height (mm) | Well Diameter (mm) | $H_{Z,Crit}$ (mm) |
| --- | --- | --- | --- |
| Costar Black Flat Bottom 96-Well 3915 | 10.71 | 6.71 | −0.85 |
| Dynatech MicroFluor Round Bottom | 9.99 | 6.78 | −1.72 |
| Costar Black 384-Well 3710 | 11.55 | 3.66 | 6.76 |
| Packard White 384-Well #6005214 | 11.57 | 3.71 | 6.67 |

Z-height can be optimized for a particular microplate and chemistry by (1) preparing a test microplate with representative chemistry (e.g., blanks, positive and negative controls, dilution series), (2) and reading the microplate multiple times at different Z-heights to determine the Z-height that gives the best signal-to-background data. Some combinations of chemistry and microplate are relatively insensitive to Z-height, while others demonstrate a distinct optimum.

As described above, a sample container sensor switch is mounted on the top optics head to prevent the plate from contacting the optics head in case the plate is misaligned, not properly specified, or the Z-height is set incorrectly. If this sensor detects a fault, the sample container will be ejected prior to reading.

Although this discussion was presented for microplates, the same principles apply with other sample containers.

Light Source and Detector Modules

Figure 19:
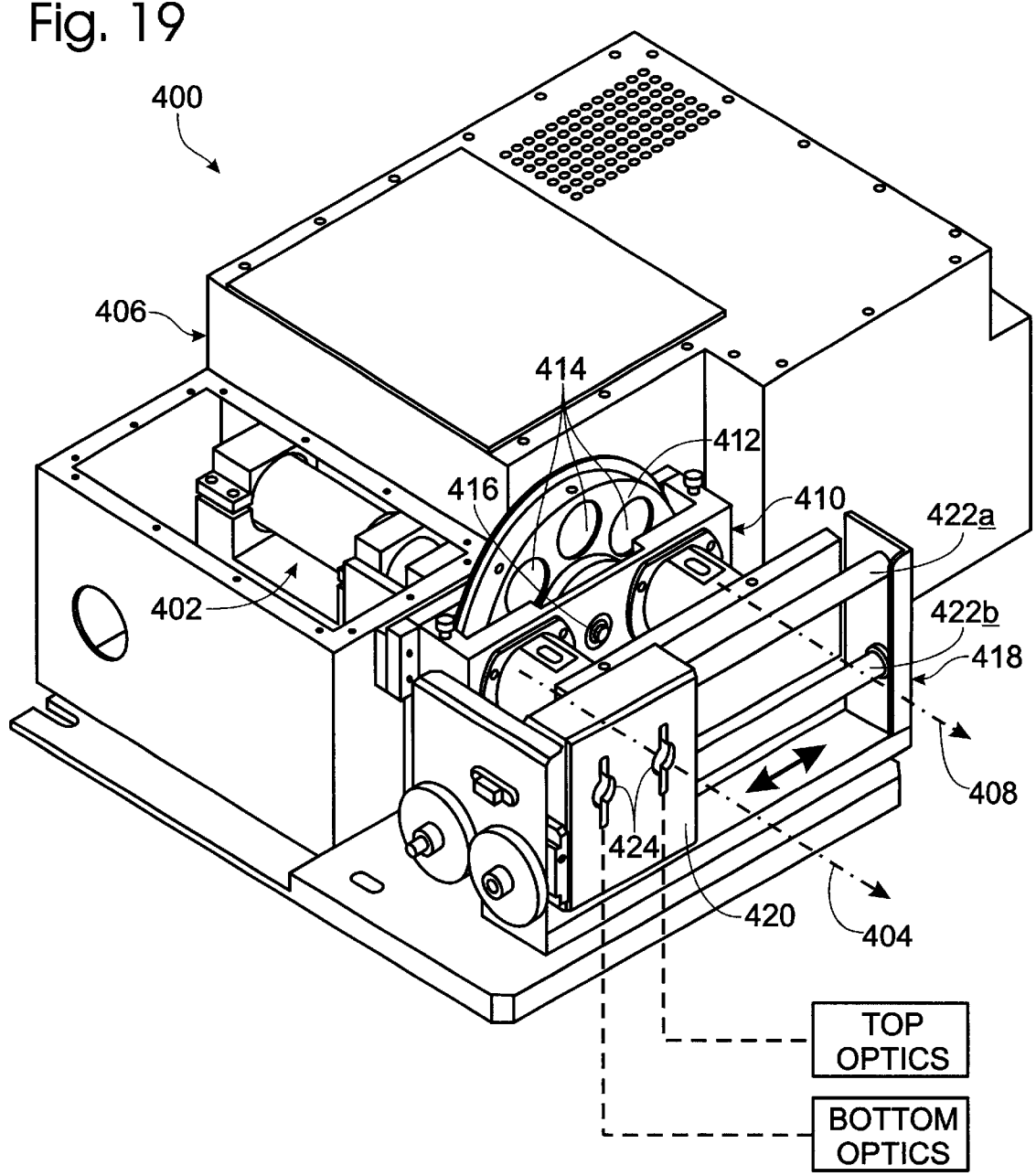
FIG. 19 is a partial perspective, partial schematic view of a light source module employed in an embodiment of the invention.

FIG. 19 is a perspective view of a light source module 400 employed in an embodiment of the invention. Portions of the module case have been removed to reveal internal componentry. Light source module 400 includes at least two light sources. A flash lamp 402 transmits light along a first light path 404. A second light source, namely, a continuous arc lamp (not shown) housed in compartment 406, transmits light along a second light path 408. A filter wheel assembly 410 is positioned adjacent the light sources. Filter wheel assembly 410 includes a filter wheel 412, which holds a plurality of filters 414. Filter wheel 412 is rotatable around an axis 416, so that a given filter can be positioned interchangeably along light path 404, or along light path 408, by rotating filter wheel 412. A fiber optic shuttle assembly 418 is mounted next to filter wheel assembly 410. Moveable shuttle 420 translates along support tracks 422a and 422b, so that moveable shuttle 420 can be positioned in front of a selected light source for a selected assay application. Two fiber optic ports 424 are provided on an external face of shuttle 420. Fiber optic ports 424 direct light, via fiber optic cables, from a selected source either to a top optics head or to a bottom optics head, above and below a stage holding a sample, respectively.

Figure 20:
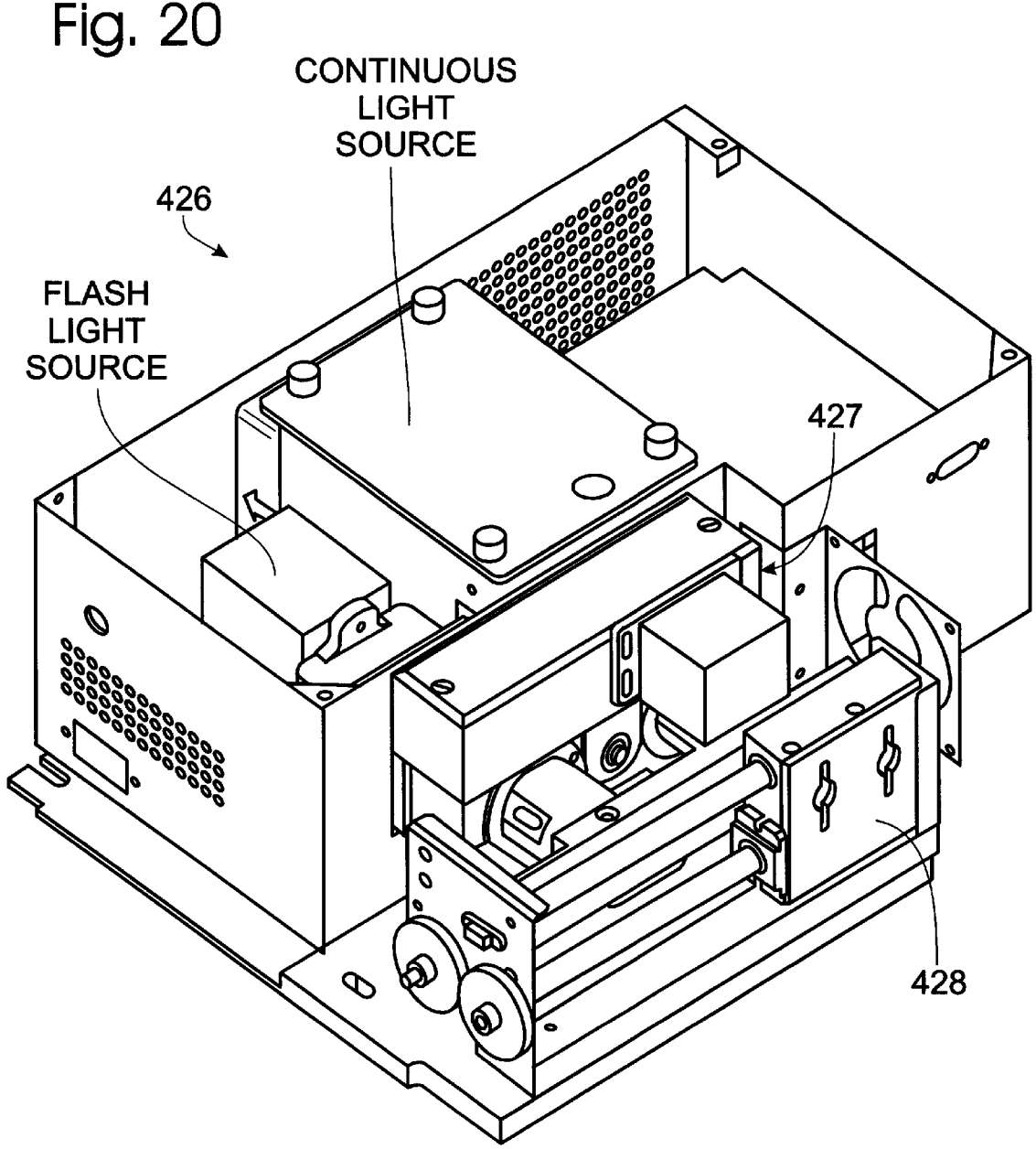
FIG. 20 is a partial perspective view of an alternative light source module.

FIG. 20 is a perspective view of an alternative light source module 426. In this embodiment, filter wheel assembly 410 of light source module 400 has been replaced by an alternative filter wheel assembly 427. A moveable shuttle 428 is shown in an alternative position relative to moveable shuttle 420 in light source module 400.

Figure 21:
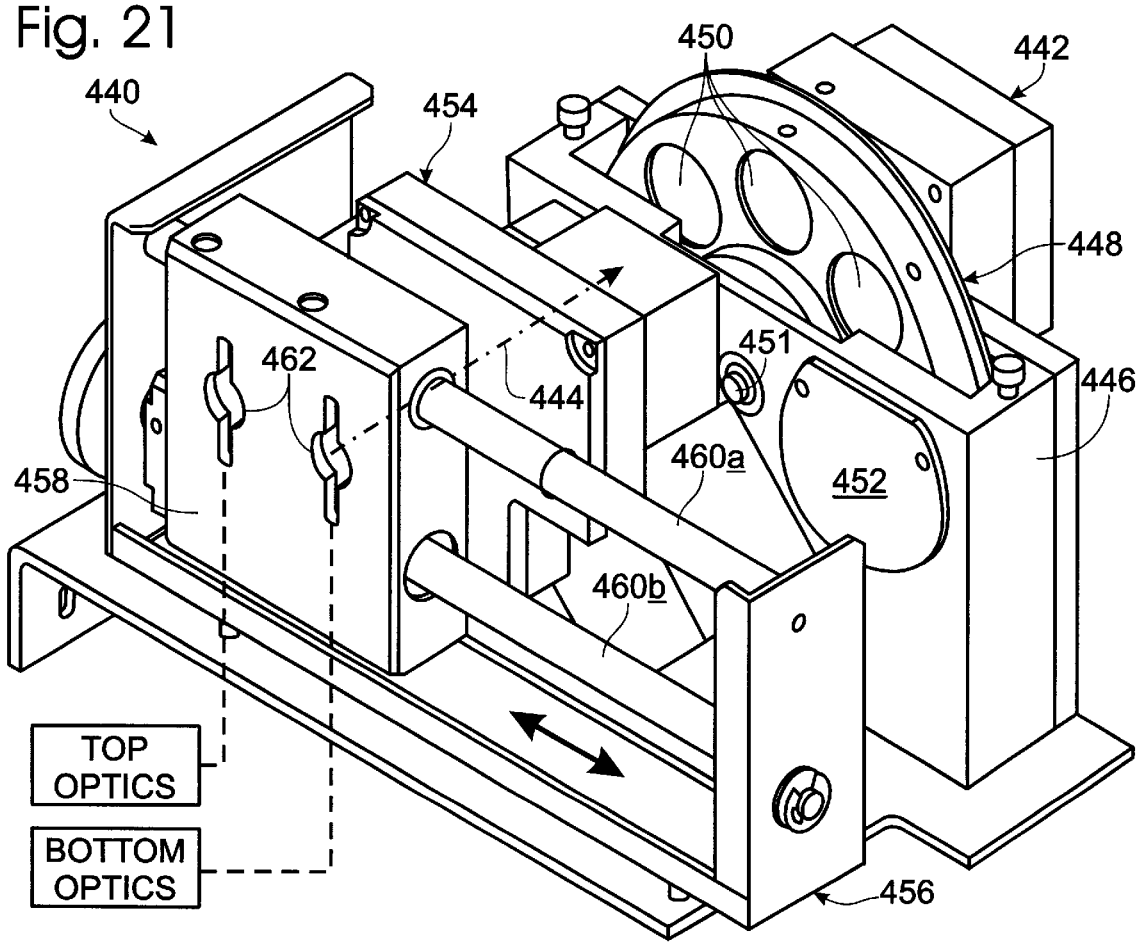
FIG. 21 is a partial perspective, partial schematic view of a detector module employed in an embodiment of the invention.

FIG. 21 is a perspective view of a detector module 440 employed in an embodiment of the invention. Portions of the module case have been removed to reveal internal componentry. Detector module 440 is similar to light source module 400. A detector 442 receives light directed along a light path 444, originating from a sample. A filter wheel assembly 446 is positioned in front of detector 442. Filter wheel assembly 446 includes a plurality of filters 450 and is rotatable around an axis 451 by a stepper, DC servo, or other motor. The filter wheel can be rotated at a preselected angular speed to allow synchronization with a flash lamp light source and a detector. A port 452 for a second detector is provided in filter wheel assembly 446, so that a second detector can be mounted in detector module 440. A given filter in filter wheel 448 can be positioned along a first light path 444 leading to detector 442, or alternatively can be positioned along a second light path leading to a second detector (not shown). An attenuator mechanism 454 is mounted adjacent filter wheel assembly 446. A fiber optic shuttle assembly 456 is mounted in front of attenuator mechanism 454. Shuttle assembly 456 includes a moveable shuttle 458, which is moveable along upper and lower support tracks 460a and 460b, respectively. An exterior face of shuttle 458 has two fiber optic ports 462, one of which is connected, via a fiber optic cable, to a top optics head above the examination site, the other of which is connected, via a fiber optic cable, to a bottom optics head below the examination site. In operation, moveable shuttle 458 can be moved along support tracks 460 a and 460 b to connect optically either one of the optics heads to any one of the detectors (if more than one is included in the module), and through any one of filters 450 in filter wheel 448.

Figure 22:
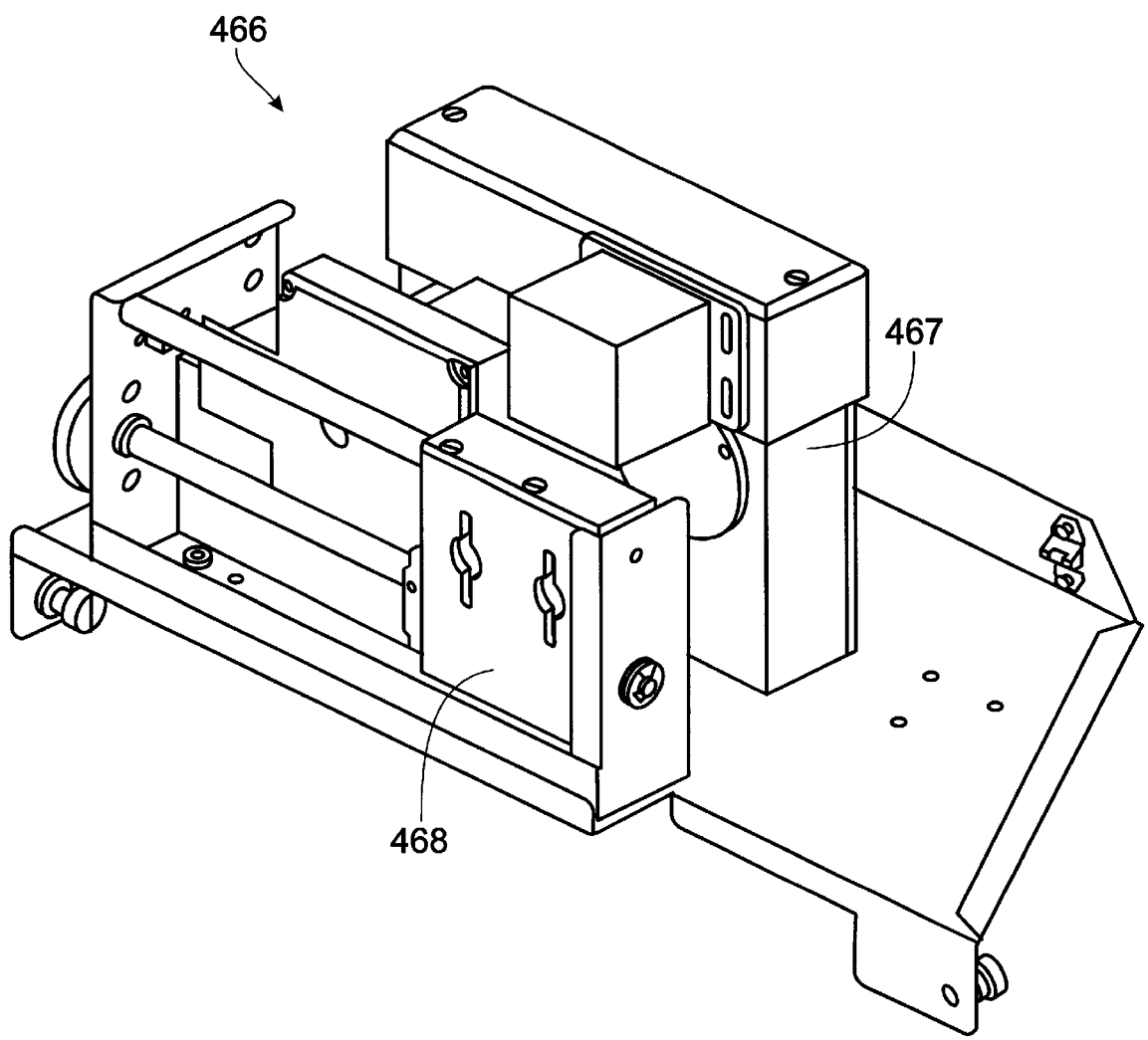
FIG. 22 is a partial perspective view of an alternative light source module.

FIG. 22 is a perspective view of an alternative detector module 466. In this embodiment, filter wheel assembly 446 of detector module 440 has been replaced by an alternative filter wheel assembly 467. A moveable shuttle 468 is shown in an alternative position relative to moveable shuttle 458 in detector module 440.

Light source and detector modules are designed for flexibility. Additional ports for fiber optics or other optical relay structures may be provided, if desired. The number and configuration of such other ports may be tied to the number and configuration of light-transmission routes through the filter wheel. Optical components also may be connected directly to the moveable shuttle. Such a connection would be especially useful for small, dedicated components, such as a beamsplitter and photodiode-type detector that could sample a portion of the light transmitted through the port to correct for output fluctuations from a light source.

A comparison of FIGS. 19 and 21, and FIGS. 20 and 22, shows that many aspects of light source modules 400 and 426 and detector modules 440 and 466 are the same, particularly the mechanics of filter wheel assemblies 410 and 446, filter wheel assemblies 427 and 467, and fiber optic shuttle assemblies 418 and 456. The light source and detector modules both function as registration mechanisms that align the end of an optical relay structure with an aperture in a surface. This surface may enclose a light source, detector, or other optical component. The light source and detector modules both permit alignment with two such apertures, and with portions of a surface not including an aperture to prevent the optical relay structure from transmitting light. Light source and detector modules also may be configured to transmit light directly from module to module, using air, a tube, or other mechanism to transmit light. If used together in a light detection device, the light source and detector modules provide a great deal of analytical flexibility to select different combinations of light sources, detectors, and filters for different applications, while also being able to select different combinations of top versus bottom illumination and detection orientations.

Figure 23:
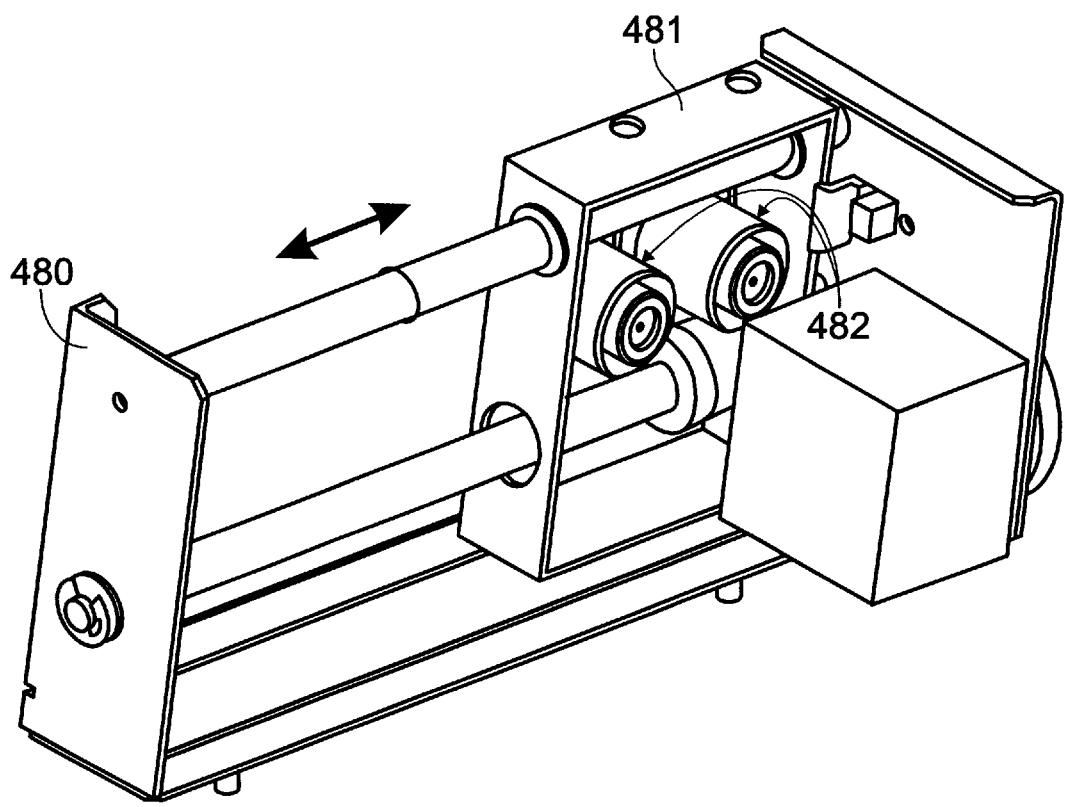
FIG. 23 is a partial perspective view of a fiber optic shuttle assembly employed in an embodiment of the invention.

FIG. 23 is a partial perspective view of a fiber optic shuttle assembly 480 like those used in light source module 400 and detector module 440. Fiber optic shuttle assembly 480 includes a moveable shuttle 481 and two floating head assemblies 482. Among other applications, each floating head assembly 482 may be used to create and maintain a light-tight connection between selected light sources or detectors and fiber optic cables, such as those that lead to an examination site, or to a top optics head or a bottom optics head, above and below a stage, respectively.

Figure 24:
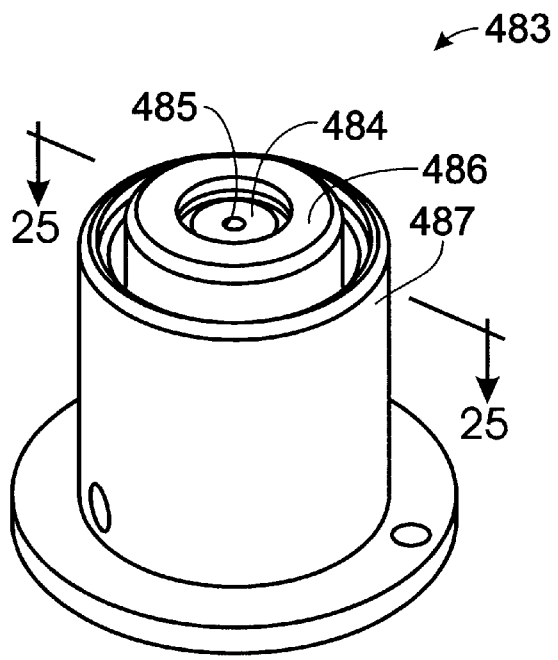
FIG. 24 is a perspective view of a floating head assembly employed in the fiber optic shuttle assembly shown in FIG. 23.

FIG. 24 shows a perspective view of a floating head assembly 483 employed in an embodiment of the invention. Generally, floating head assembly 483 includes a fiber optic ferule 484 having an end 485 configured to transmit light, and an opaque collar 486 positioned around the end. Fiber optic ferule 484 is used to transmit light. Fiber optic ferule 484 may be replaced by a portion of a light source, detector, or other optical component. Opaque collar 486 is used to block light and preferably comprises a hard plastic material. Opaque collar 486 encompasses and extends beyond end 485. An opaque base structure 487 contains additional elements. Together, opaque collar 486 and base structure 487 form a pair of concentric, partially overlapping walls positioned around fiber optic ferule 484.

Figure 25:
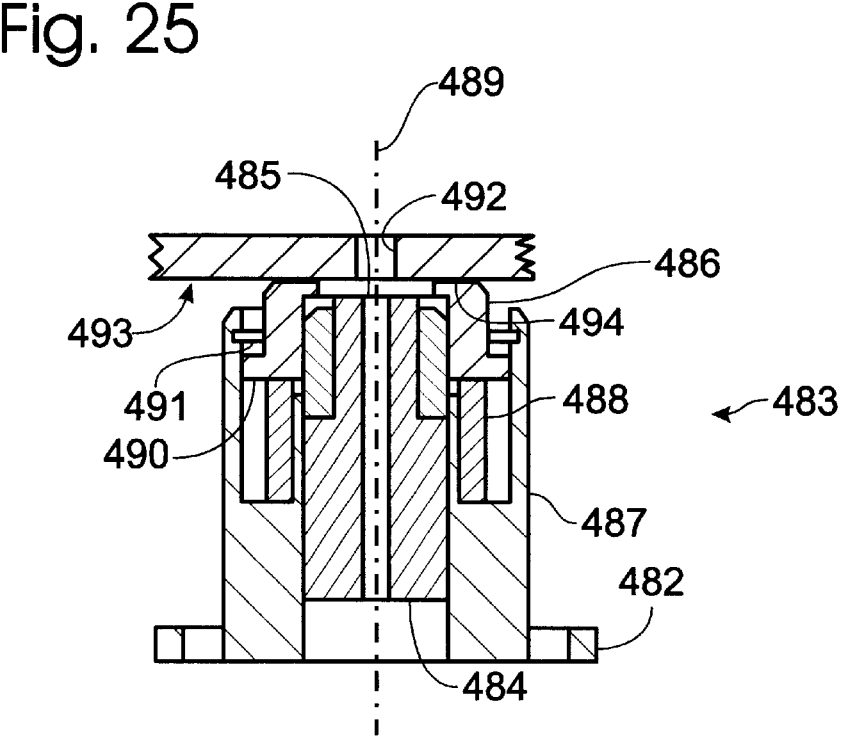
FIG. 25 is a cross-sectional view of the floating head assembly, taken generally along the line 25—25 in FIG. 24.

FIG. 25 is a cross-sectional view of floating head assembly 483. A spring 488 is positioned between portions of opaque collar 486 and base structure 487. Spring 488 generally comprises any elastic body or other device that recovers its original shape when released after being distorted. Spring 488 is configured to spring-bias opaque collar 486 relative to end 485 when spring 488 is compressed between opaque collar 486 and base structure 487. Spring 488 bias pushes opaque collar 486 and base structure 487 in opposite directions parallel to a central axis 489 running through fiber optic ferule 484. A flange 490 on opaque collar 486 contacts a retaining ring 491 on base structure 487 when opaque collar 486 is maximally extended, limiting relative movement of opaque collar 486 and base structure 487. Additional or alternative stop mechanisms also may be employed, such as a set screw.

In use, floating head assembly 483 is positioned such that fiber optic ferule 484 is aligned with an aperture 492 in a surface 493, so that light may be transmitted between fiber optic ferule 484 and aperture 492. When end 485 and aperture 492 are aligned, a leading rim edge 494 of opaque collar 486 is spring-biased or forced against surface 493 by compression of spring 488. Leading rim edge 494 defines an end plane that is moveable relative to central axis 489. Opaque collar 486 and thus leading rim edge 494 automatically float or reorient relative to surface 493, forming a substantially light-tight junction by changing angle relative to central axis 489. This substantially light-tight junction substantially prevents stray light from entering the system, and it substantially prevents signal light from exiting the system. Spring 488 is relatively more compressed where surface 493 is closer to floating head assembly 483 and relatively less compressed where surface 493 is farther from floating head assembly 483, so that contact between opaque collar 486 and surface 493 is maintained for different positions and/or orientations of surface 493. Portions of opaque collar 486 may be formed of a material that deforms under pressure from spring 488 to conform substantially to asperities or other irregularities in surface 493.

Figure 26:
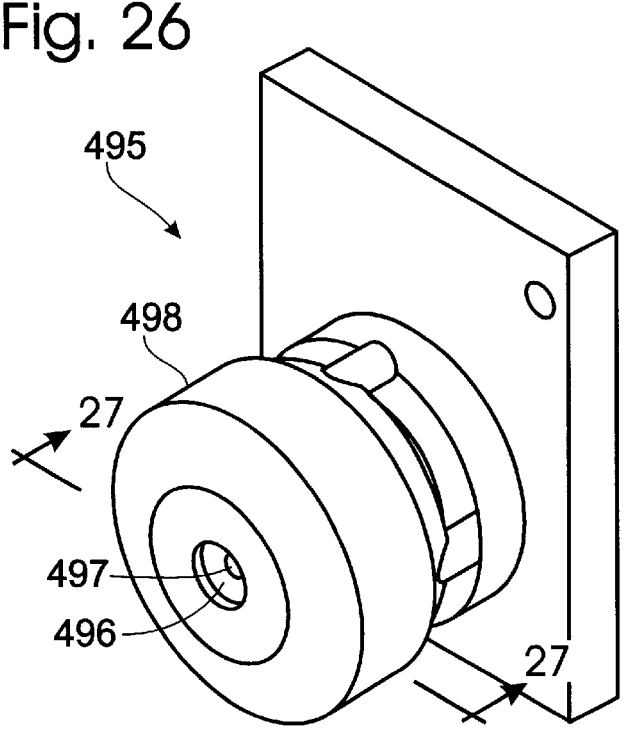
FIG. 26 is a perspective view of an alternative floating head assembly.

FIG. 26 shows a perspective view of an alternative floating head assembly 495. Generally, alternative floating head assembly 495 includes a fiber optic cable 496 having an end 497 configured to transmit light, and an opaque collar 498 positioned around the end.

Figure 27:
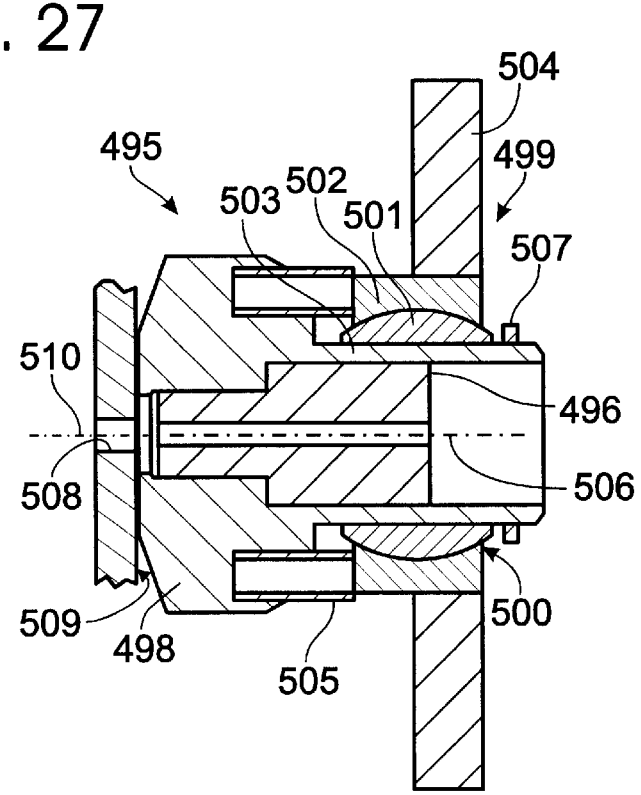
FIG. 27 is a cross-sectional view of the alternative floating head assembly, taken generally along the line 27—27 in FIG. 26.

FIG. 27 shows a cross-sectional view of alternative floating head assembly 495. Fiber optic ferule 496 and opaque collar 498 are supported by a base structure 499 that includes a spherical bearing 500 having an inner race 501 and an outer race 502. Inner race 501 is slidingly connected to a sleeve portion 503 of opaque collar 498 that extends along fiber optic ferule 496. Outer race 502 is connected to a platform structure 504 used for mounting alternative floating head assembly 495. A spring 505 is positioned between portions of opaque collar 498 and outer race 502. Spring 505 bias pushes opaque collar 498 and base structure 499 in opposite directions parallel to a central axis 490 running through fiber optic ferule 496. A retaining ring 507 prevents over-extension of opaque collar 498.

In use, alternative floating head assembly 495 is positioned, like floating head assembly 483, such that fiber optic ferule 496 is aligned with an aperture 508 in a surface 509, so that light may be transmitted between fiber optic ferule 496 and aperture 508. When so aligned, opaque collar 498 and fiber optic ferule 496 are free to compress and extend due to the action of spring 505, and to swivel and reorient due to the action of spherical bearing 500, relative to surface 509. The combined actions of spring 505 and spherical bearing 500 ensure that central axis 506 of fiber optic ferule 496 always is substantially parallel to an aperture axis 510 running through aperture 508, unlike with floating head assembly 483.

Filter Wheel Assemblies

Figure 28:
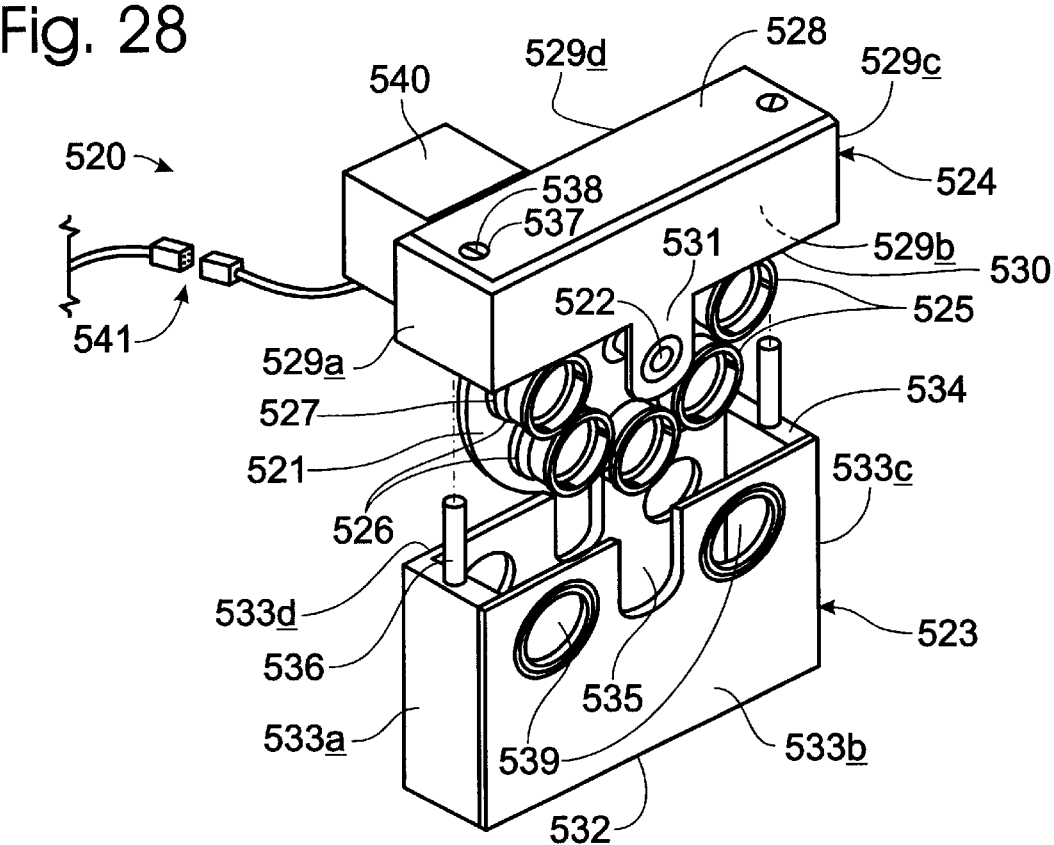
FIG. 28 is a partially exploded perspective view of an optical filter wheel assembly employed in an embodiment of the invention.

FIG. 28 shows a partially exploded perspective view of an optical filter wheel assembly 520 employed in an embodiment of the invention. Optical filter wheel assembly 520 includes a filter wheel 521 that is rotatable about a hub structure 522, and a wheel case having a static base portion 523 and a removable lid portion 524. Hub structure 522 is built into removable lid portion 524.

Filter wheel 521 holds filter cartridges 525. Filter wheel 521 is substantially circular and includes a plurality of apertures 526 disposed symmetrically about its outer perimeter 527. Apertures 526 are used for mounting filter cartridges 525 and may hold the filter cartridges via friction, threads, or other means. Filter wheel 521 may have a variety of shapes, and apertures 526 may be disposed in a variety of configurations, although a symmetric embodiment is preferred for balance and ease of rotation about hub structure 522.

Removable lid portion 524 holds filter wheel 521. Removable lid portion 524 is substantially rectangular, with an enclosed top 528 and sides 529*a–d* and an open bottom 530 for receiving filter wheel 521. Opposed flanges 531 extend downward from one pair of opposed sides 529*b,d* of removable lid portion 524 to support hub structure 522. Filter wheel 521 is rotatably mounted through its center on hub structure 522.

Static base portion 523 holds removable lid portion 524 and filter wheel 521. Static base portion 523 is substantially rectangular, with an enclosed bottom 532 and sides 533*a–d* and an open top 534 for receiving filter wheel 521. Opposed slots 535 extend downward into one pair of opposed sides 533*b,d* of static base portion 523 to receive opposed flanges 531. Opposed posts 536 extend upward from the other pair of opposed sides 533*a,c* of static base portion 523 to be received by opposed holes 537 in opposed sides 529*a,c* of removable lid portion 524. Flanges 531 and slots 535, and posts 536 and holes 537, individually and collectively form a post-to-hole mating structure that aligns static base portion 523 and removable lid portion 524 when the two portions are mated together to form the wheel case. Captive screws 538 situated in holes 537 and accessible from top 528 may be threaded into posts 536 to hold together removable lid portion 524 and static base portion 523. Static base portion 523 further may be fixed to an instrument platform to form a portion of a light source module, detector module, or other optical assembly, among other applications.

The assembled wheel case is substantially light-tight, except for light that is transmitted through two sets of opposed windows 539 included in static base portion 523. Windows 539 are used for transmitting light through the wheel case and through a selected optical filter contained in a filter cartridge 525 in filter wheel 521. Windows 539 are located on opposite sides of hub structure 522, so that any given optical filter in filter wheel 521 can be rotated into alignment with either set of windows. In turn, light sources, detectors, and other optical components can be aligned with either or both sets of filters. Generally, the wheel case includes at least one set of windows, which may be located on the static portion, removable portion, or other portion of the wheel case.

Filter wheel 521 may be rotated by a drive motor 540, which is attached to removable lid portion 524 in optical filter wheel assembly 520. Drive motor 540 or other driver mechanisms also may be operatively connected to optical filter wheel assembly 520 at other points and in other manners.

FIG. 28 also shows a mechanism by which optical filter wheel assembly 520 may be disassembled and reassembled. Optical filter wheel assembly 520 is disassembled as follows. First, any associated instrument is powered down and unplugged. Second, any secondary housing enclosing optical filter wheel assembly 520 is removed. Third, drive motor 540 is unplugged at its inline connector 541. Fourth, captive screws 538 are loosened. Finally, removable lid portion 524 and filter wheel 521 are pulled out of static base portion 523.

Optical filter wheel assembly 520 may be reassembled as follows. First, filter cartridges 525 are checked to verify that they are properly seated in filter wheel 521, and filter wheel 521 is checked to verify that it rotates smoothly about hub structure 522 when moved by hand. Second, removable lid portion 524 and filter wheel 521 are inserted into static base portion 523, aligning flanges 531 with slots 535, and posts 536 with holes 537. Third, captive screws 538 are tightened. Fourth, drive motor 540 is plugged back in at inline connector 541. Fifth, any secondary housing is replaced. Finally, any associated instrument is plugged back in and powered up, if desired.

Figure 29:
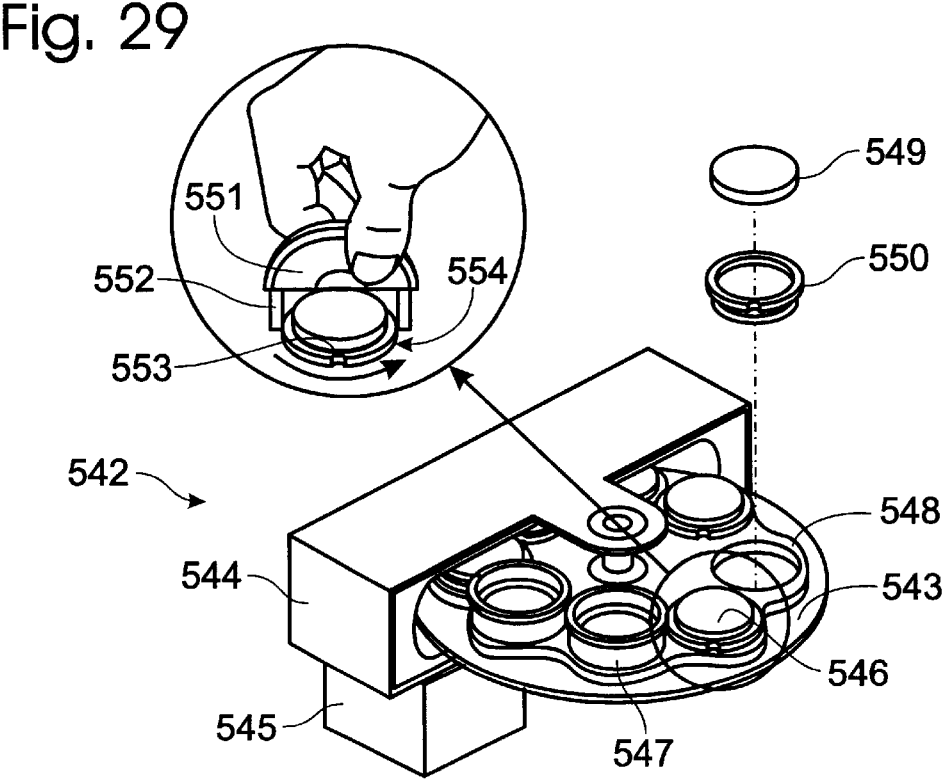
FIG. 29 is a partially exploded perspective view of a portion of an optical filter wheel assembly like that shown in FIG. 1, showing a mechanism by which short filter cartridges may be removed.

FIG. 29 shows a partially exploded perspective view of a removable portion 542 of an optical filter wheel assembly, including a filter wheel 543, removable lid portion 544, and drive motor 545. Filter wheel 543 includes a set of "short" filter cartridges 546 and a set of "tall" filter cartridges 547. Filter wheel 543 may hold a variety of filter cartridges, so long as the filter cartridges are configured to fit in apertures 548 in the filter wheel. Generally, opposed apertures in filter wheel 543 should contain matching filter cartridges or a suitable slug to balance the filter wheel and to prevent unfiltered radiation from reaching a detector.

FIG. 29 also shows a mechanism by which short filter cartridges 546 may be removed and replaced. Generally, short filter cartridges 546 include an optical filter 549 permanently affixed by suitable means, such as glue, to a short filter barrel 550 having a low profile. Optical filter 549 may include an intensity filter, a spectral filter, or a polarization filter, among others. Short filter cartridges 546 are removed from filter wheel 543 as follows. First, with the filter wheel removed as described above, the desired short filter cartridge is located by sight or by location. (Filter cartridge locations within the filter wheel may be marked on the filter wheel or elsewhere for reference.) Second, the short filter cartridge is removed by turning it counter-clockwise, which unscrews it. The short filter cartridge may be turned by hand or by a special tool, such as a spanner wrench 551 having prongs 552 that engage grooves 553 in the sides of the short filter cartridge 554. Finally, filter changes are noted on the filter wheel or elsewhere and in any associated instrument software. Short filter cartridges 546 may be replaced in filter wheel 543 by reversing the process, turning the short filter cartridge clockwise.

Figure 30:
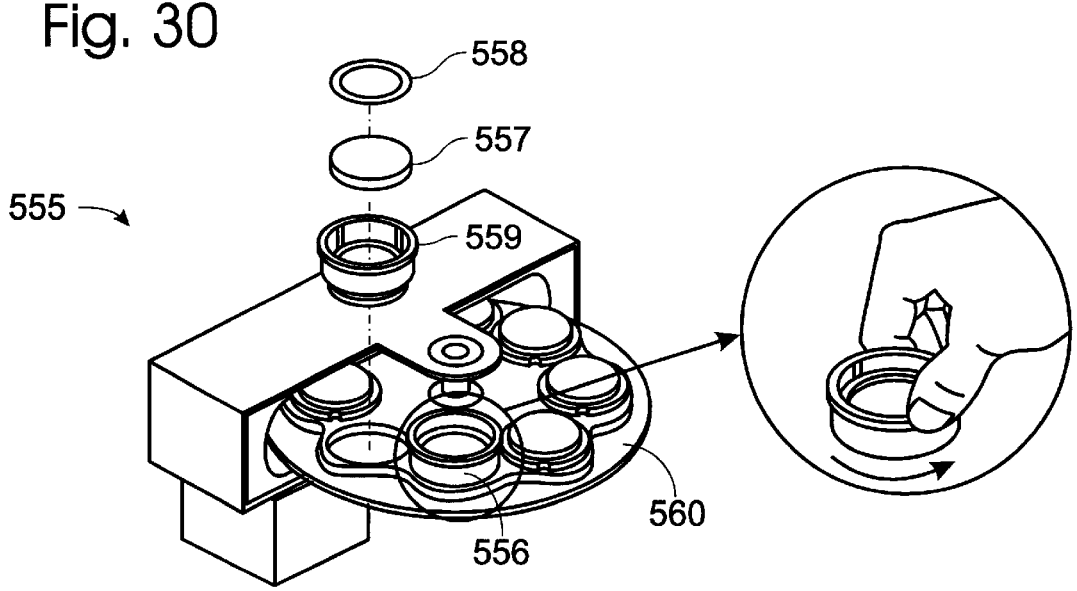
FIG. 30 is a partially exploded perspective view of the portion of the optical filter wheel assembly shown in FIG. 29, showing a mechanism by which tall filter cartridges may be removed.

FIG. 30 shows a partially exploded perspective view of a removable portion 555 of an optical filter wheel assembly, as shown in FIG. 29. FIG. 30 also shows a mechanism by which tall filter cartridges 556 may be removed and replaced. Generally, tall filter cartridges 556 include an optical filter 557 affixed by a removable friction member 558 to a tall filter barrel 559. Optical filter 557 may include an intensity filter, a spectral filter, or a polarization filter, among others. Friction member 558 and tall filter barrel 559 may be substantially annular. Tall filter cartridges 556 may be removed from and replaced in filter wheel 560 much like short filter cartridges 546; however, tall filter cartridges 556 generally are turned by hand rather than by a tool.

Figure 31:
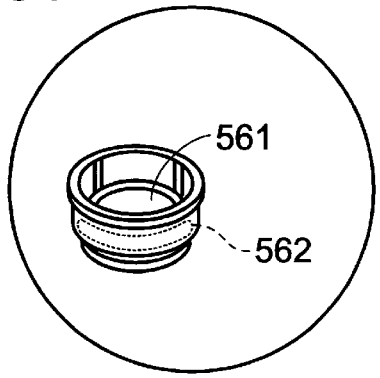
FIG. 31 is a perspective view showing a mechanism by which optical filters may be placed in a tall filter cartridge.
Figure 32:
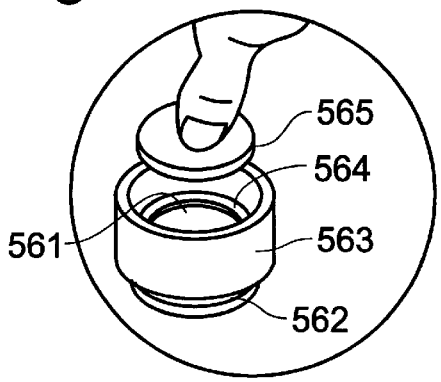
FIG. 32 is a perspective view showing a mechanism by which a friction member may be pressed into place using a funnel and slug.

FIGS. 31 and 32 show a perspective view of a mechanism by which optical filters may be replaced in the tall filter cartridges. First, as shown in FIG. 31, the optical filter 561 is placed in the tall filter barrel 562. Optical filter 561 should be oriented properly if one side is different than the other. Additional optical filters 561 can be placed in tall filter barrel 562, if desired. Second, as shown in FIG. 32, a funnel structure 563 is placed on top of tall filter barrel 562. Third, an annular friction member 564 is placed in funnel structure 563, followed by a slug 565. Slug 565 and optical filter 561 have approximately equivalent peripheral dimensions, including radii. Fourth, slug 565 is pushed down through funnel structure 563 to compress friction member 564, which should fit snugly against optical filter 561. Finally, slug 565 and funnel structure 563 are removed. The completed tall filter cartridge then can be installed in a filter wheel, as described above.

Optical filter 561 also may be replaced by other techniques. Generally, the tall filter cartridges incorporate a mechanism that permits easy replacement of different optical filters in the same cartridge, enhancing the flexibility of the tall cartridges.

Optical filter 561 may be removed from the tall filter cartridge as follows. First, a lint-free cloth is placed on a work surface. Second, the installed optical filter 561 (or slug 565) is pushed gently near its center with a gloved finger or thumb, which will cause the optical filter 561 and friction member 564 to drop out of tall filter barrel 562. Removed optical filter 561 should be stored so that it will not become dirty or scratched.

Figure 33:
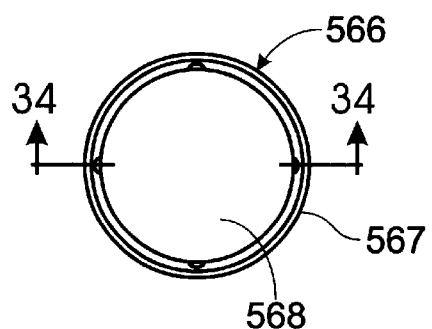
FIG. 33 is a top view of a short filter cartridge employed in an embodiment of the invention.
Figure 34:
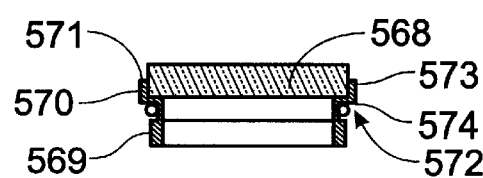
FIG. 34 is a cross-sectional view of the short filter cartridge, taken generally along the line 34—34 in FIG. 33.

FIGS. 33 and 34 show detailed views of a short filter cartridge 566, which includes a short filter barrel 567 and optical filter 568. Short filter barrel 567 is substantially annular, with a threaded lower portion 569 that screws into an aperture in a filter wheel, and a graspable upper portion 570 having a knurled rim 571 that may be turned by hand. Optical filter 568 is supported by upper portion 570, and mounts adjacent a stop structure 572 and inner wall 573 on short filter barrel 567, so that it is substantially centered relative to short filter barrel 567. Stop structure 572 includes an edge 574 oriented substantially perpendicular to a principal plane of optical filter 568 and to inner wall 573.

Figure 35:
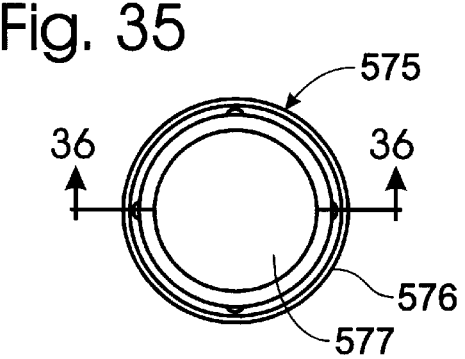
FIG. 35 is a top view of a tall filter cartridge employed in an embodiment of the invention.
Figure 36:
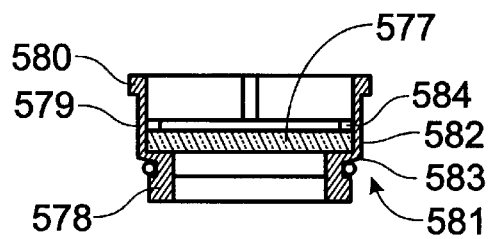
FIG. 36 is a cross-sectional view of the tall filter cartridge, taken generally along the line 36—36 in FIG. 35.

FIGS. 35 and 36 show detailed views of a tall filter cartridge 575, which includes a tall filter barrel 576 and optical filter 577. Tall filter cartridge 575 resembles short filter cartridge 566 in many respects. Tall filter barrel 576 is substantially annular, with a threaded lower portion 578 that screws into an aperture in a filter wheel, and a graspable upper portion 579 having a knurled rim 580 that may be turned by hand. Optical filter 577 is supported by upper portion 579, and mounts adjacent a stop structure 581 and inner wall 582. Stop structure 581 includes an edge 583 oriented substantially perpendicular to a principal plane of optical filter 577 and to inner wall 582. Inner wall 582 may be substantially perpendicular to the optical filter, as here, or it may have a funnel portion that graduates in diameter in a direction toward the stop structure, among other configurations. Lower portion 569 of short filter barrel 567 is substantially identical to lower portion 578 of tall filter barrel 576. However, upper portion 570 of short filter barrel 567 is shorter than upper portion 579 of tall filter barrel 576, giving it a lower profile. In addition, optical filter 568 of short filter barrel 567 is permanently affixed to upper portion 570, whereas optical filter 577 of tall filter barrel 576 is removably sandwiched in upper portion 579 between stop structure 581 and a friction member 584. Friction member 584 holds optical filter 577 in place relative to inner wall 582 in tall filter cartridge 575 by static friction, without any thread, groove, or adhesive. For this reason, among others, optical filters of various numbers and sizes may be secured.

Friction member 584 may take a variety of forms, including a compressible ring having an uncompressed outer diameter greater than the inner diameter of inner wall 582. The compressible ring may exert a force on the inner wall that provides sufficient static friction to hold an optical filter snugly in place during routine use, while also permitting easy removal when replacing optical filters.

Figure 37:
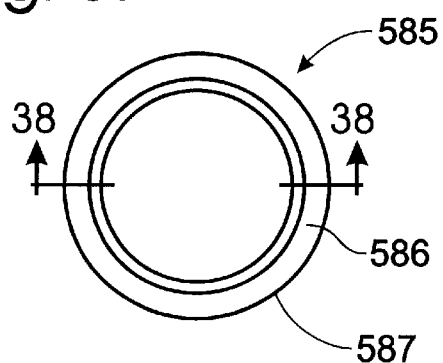
FIG. 37 is a top view of a funnel structure employed in conjunction with an embodiment of the invention.
Figure 38:
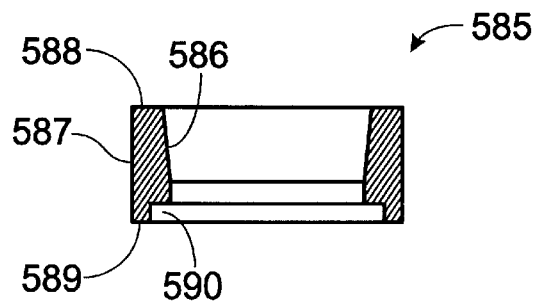
FIG. 38 is a cross-sectional view of the funnel structure, taken generally along the line 38—38 in FIG. 37.

FIGS. 37 and 38 show detailed views of a funnel structure 585, which is used for loading an optical filter into a tall filter cartridge or other holder as described above. Funnel structure 585 is substantially annular and includes inner and outer walls 586, 587 and a top end 588 and lower edge 589. Lower edge 589 includes a groove 590 adjacent inner wall 586 configured to rest on top of a filter cartridge or other holder. The inner diameter of funnel structure 585 measured between inner walls 586 enlarges gradually in a direction from lower edge 589 to top end 588.

Figure 39:
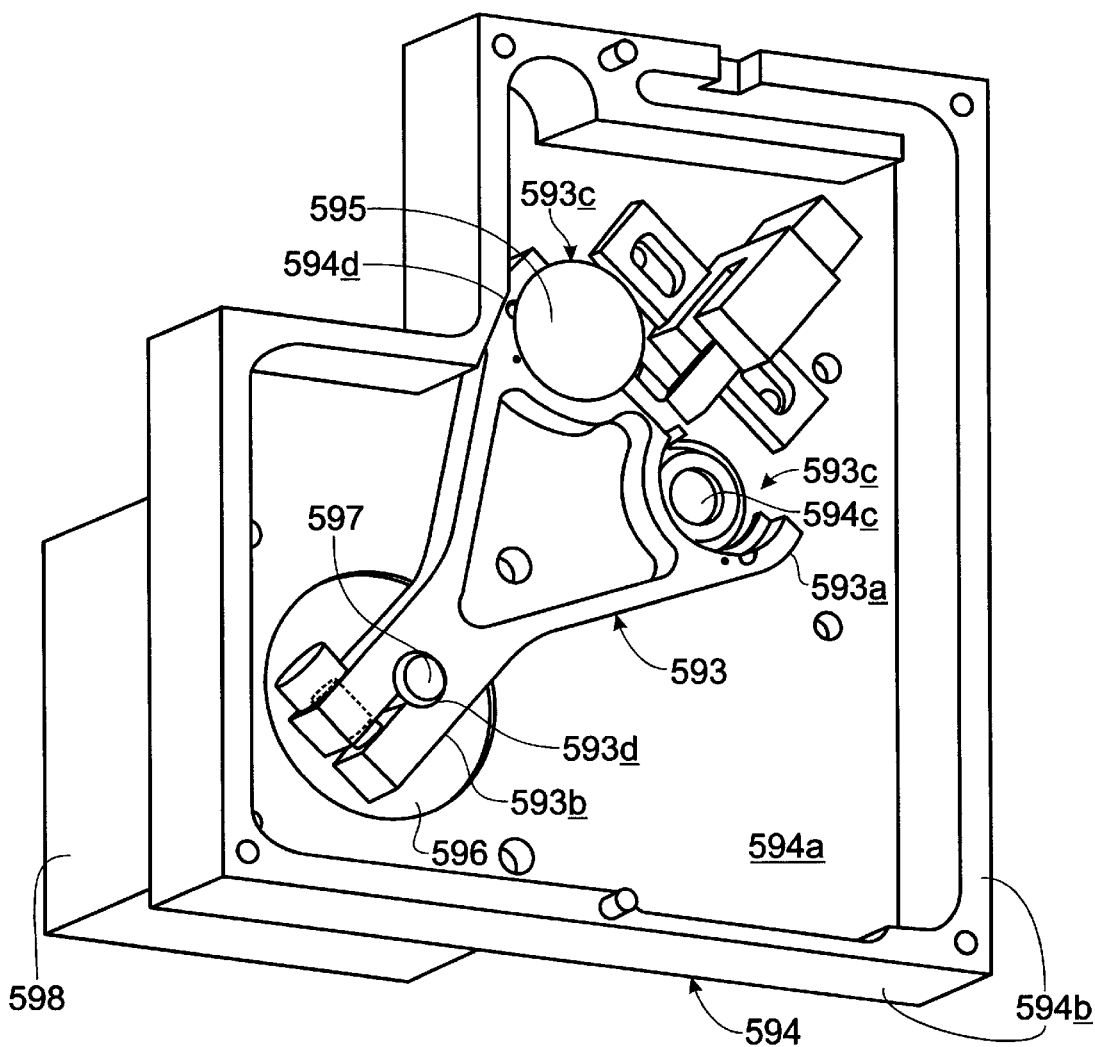
FIG. 39 is a perspective view of a pivotable filter cartridge employed in an embodiment of the invention.

FIG. 39 shows a partial perspective view of an alternative filter holder assembly 592. Filter holder assembly 592 includes an elongate filter cartridge 593 and a base 594. Elongate filter cartridge 593 includes a filter end 593a and a pivot end 593b. Filter end 593b is configured to hold optical filters, and includes two filter slots 593c in which optical filters 595 may be glued or otherwise attached. Generally, the filter end may hold one or more optical filters, using slots, apertures, short or tall filter cartridges, or other mechanisms. Filter slots may be left open so that light passes unfiltered, or filter slots may be filled with filters so that light is filtered, or filled with slugs or other opaque structures so that light is blocked. Pivot end 593b is configured turnably to attach to a hub structure, and includes an aperture 593d for receiving a drive axle or other pivot structure. Generally, the pivot end may attach through any means to any suitable drive mechanism. Elongate filter cartridge 593 is fan shaped, filter end 593a being wider than pivot end 593b, although other shapes also are possible.

Base 594 generally supports elongate filter cartridge 593. Base 594 includes a hub structure 596 and major and minor walls 594a,b that substantially surround elongate filter cartridge 593 on all but one side. Elongate filter cartridge 593 is turnably attached at its pivot end 593b to hub structure 596 through a drive axle 597, about which it may turn. Base 594 also includes a window 594c in major wall 594a.

Elongate filter cartridge 593 may be used for moving an optical filter in and out of an optical path, much like a filter wheel or filter slide, by turning elongate filter cartridge 593 about hub structure 596. Because elongate filter cartridge 593 may move one or a few filters in and out of an optical path by turning through a limited angle, it may be configured to require less space than a filter wheel of comparable radius. A drive mechanism 598 may be controlled or base 594 may be configured to limit the angle through which elongate filter cartridge 593 may turn. For example, in filter holder assembly 592, a position 594d on minor wall 594b forms a stop structure that physically limits movement if drive mechanism 594d attempts to turn elongate filter cartridge 593 past the wall.

Sample Transporter

FIGS. 40–43 show a stage, which generally comprises any mechanism for supporting a composition in a sample container for analysis by the analyzer. In analyzer 50, the stage includes a transporter 600 and base platform 700.

Figure 40:
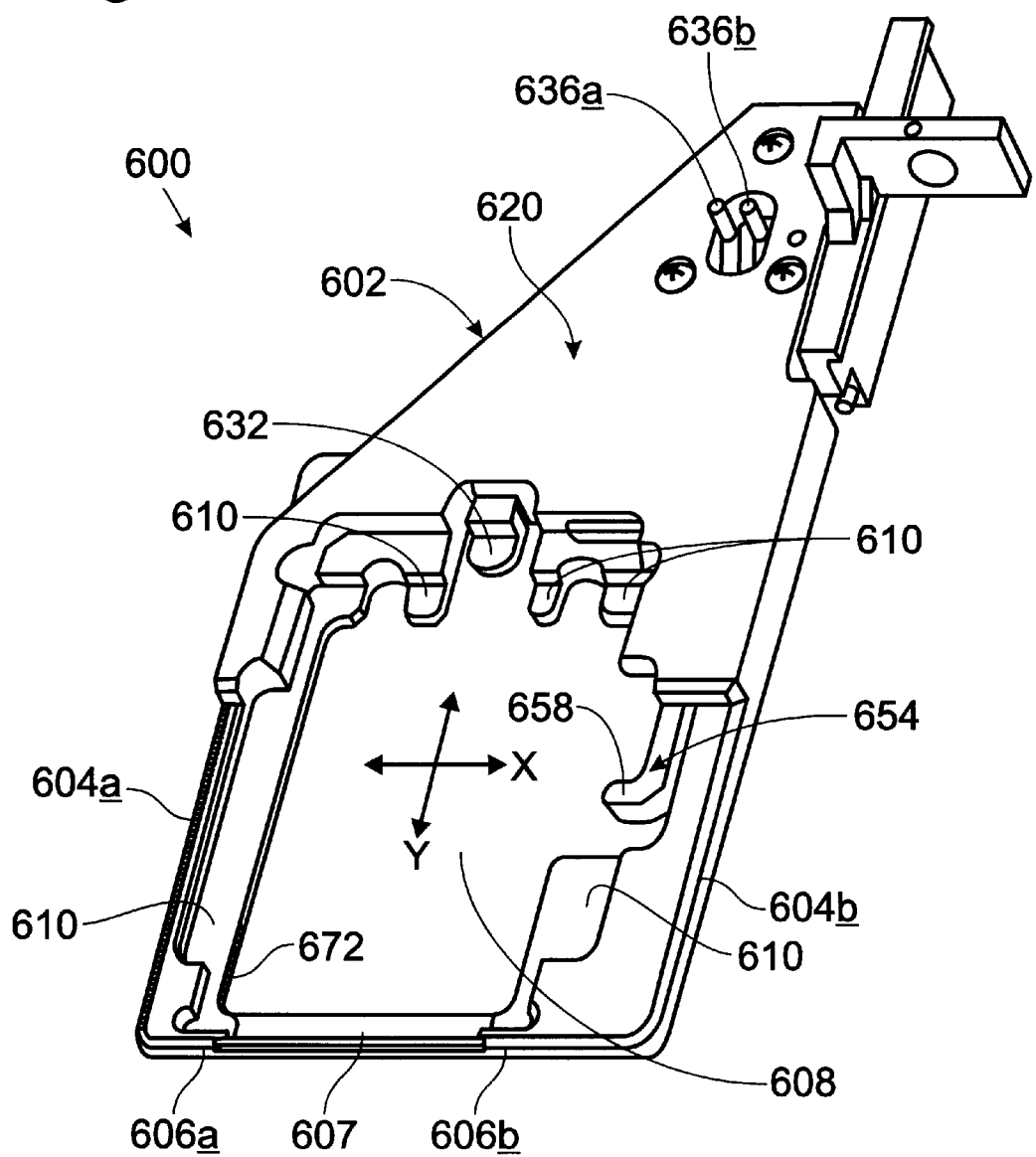
FIG. 40 is a perspective view of the top of a transporter assembly employed in an embodiment of the invention.
Figure 41:
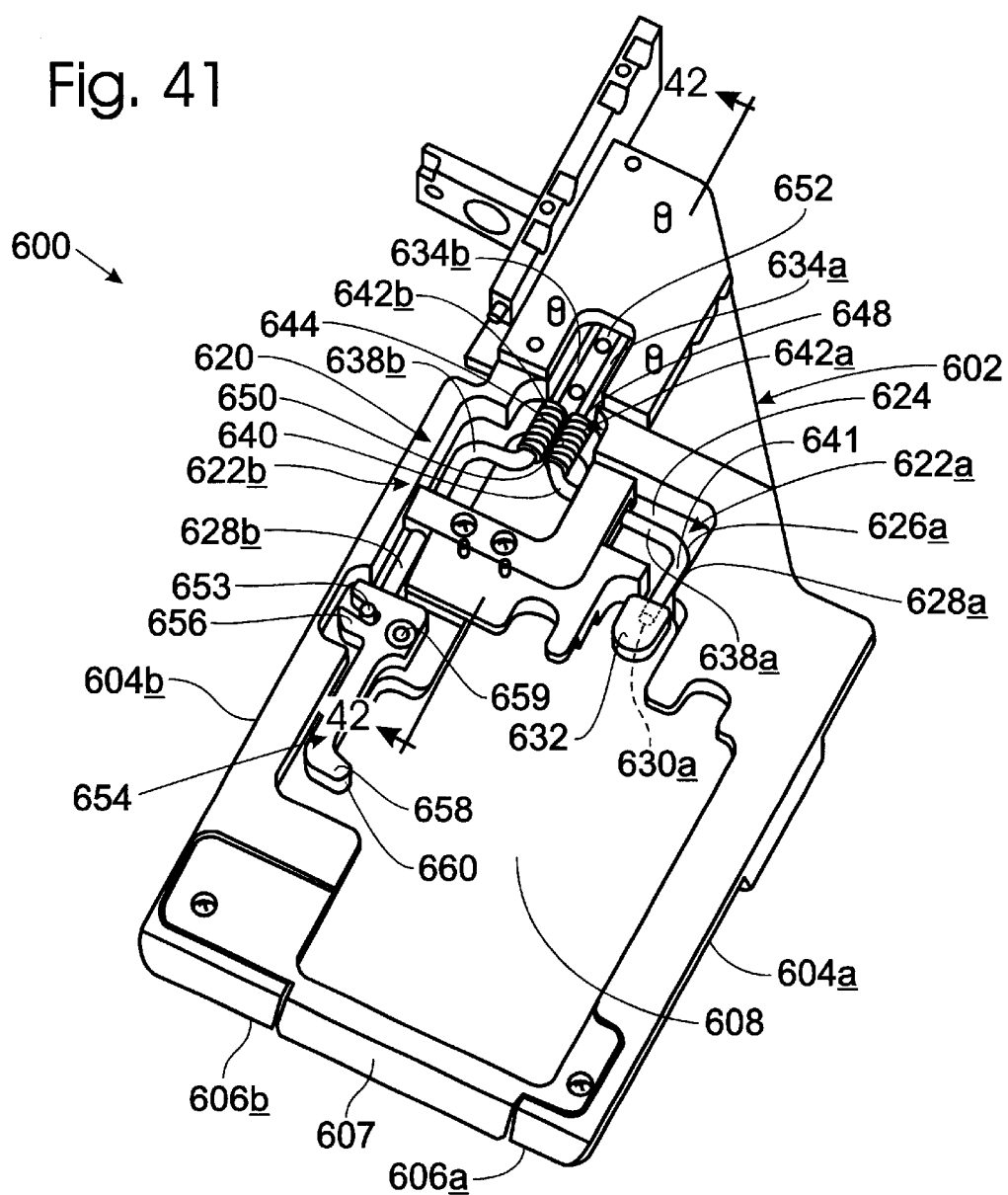
FIG. 41 is a perspective view of the bottom of the transporter assembly shown in FIG. 40.
Figure 42:
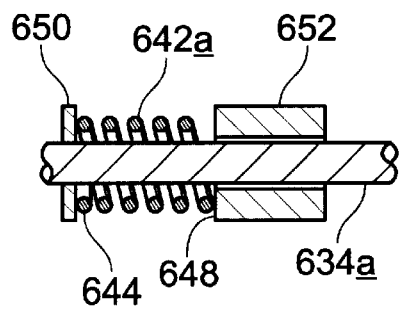
FIG. 42 is a partial cross-sectional view of the transporter assembly shown in FIGS. 40 and 41, taken generally along the line 42—42 in FIG. 41.

FIGS. 40–42 show transporter 600, which includes a transporter body 602 and substantially parallel first and second transporter flanges 604a,b that extend outward from transporter body 602. First and second transporter flanges 604a,b terminate in first and second transporter extensions 606a,b that turn in toward one another without contacting one another. Transporter extensions 606a,b may be joined by a connector portion 607. Transporter body 602, flanges 604a,b, and extensions 606a,b lie substantially in a plane and define a transporter cavity 608 that is larger than the expected peripheral dimension of any sample containers which the transporter is intended to support. The shape of this cavity is chosen to accommodate the shape of the preferred sample containers. In analyzer 50, cavity 608 is generally rectangular to accommodate generally rectangular sample containers, such as microplates. In analyzer 50, long sides of the rectangular sample container are positioned against flanges 604a,b.

Transporter 600 includes a shelf structure and associated frame structure for supporting a microplate or other sample container. For example, transporter shelves 610 along portions of body 602, flanges 604a,b, and extensions 606a,b form a shelf structure that supports the bottom of the sample container. The shelf structure also could include other support mechanisms, such as pins or pegs.

The transporter also includes an automatic sample container positioning mechanism 620 for positioning sample containers precisely and reproducibly within cavity 608. Mechanism 620 includes Y and X axis positioning arms 622a,b that contact the sample container to control its Y and X position, respectively. Here, a Y axis is defined as generally parallel to transporter flanges 604a,b, and an X axis is defined as perpendicular to the Y axis and generally parallel to transporter extensions 606a,b. Other coordinate systems also can be defined, so long as they include two noncolinear directions.

Y-axis positioning arm 622a lies substantially within a channel 624 in body 602. Y-axis positioning arm 622a includes a rod 626a, which is bent at substantially right angles to form three substantially coplanar and equal-lengthed segments. A first end segment 628a of rod 626a terminates near cavity 608 in a bumper 632 for engaging a sample container. A second end segment 634a of rod 626a terminates away from cavity 608 in an actuator tab 636a for controlling movement of arm 622a. Actuator tab 636a is bent away from body 602. First and second end segments 628a, 634a are substantially parallel. A middle segment 638a of rod 626a connects the two end segments at their nontabbed ends 640, 641. An X-axis biasing spring 642a having first and second spring ends 644, 648 is slipped over rod 626a. First spring end 644 is held to second end segment 634a of rod 626a by a clamping-type retaining ring 650. Second spring end 648 rests against a rod bearing 652. The Y-axis biasing spring extends substantially parallel to first and second end segments 628a, 634a. The force from spring 642a is transmitted to rod 626a by the clamping action of retaining ring 650.

X-axis positioning arm 622b also lies substantially within channel 624 in body 602 and is similar to Y-axis positioning arm, except that (1) first end segment 628b is longer and middle segment 638b is shorter in rod 626b of the X-axis positioning arm than in rod 626a of the Y-axis positioning arm, (2) first end segment 628a terminates in a lever tab 653 in the X-axis positioning arm rather than in bumper 632 in the Y-axis positioning arm, and (3) the two rods bend in opposite directions between first end segments 628a,b and second end segments 634a,b.

X-axis positioning arm 622b is connected via lever tab 653 to an X-axis positioning lever 654 that lies along transporter flange 604b. X-axis positioning lever 654 includes first and second lever projections 656, 658 and is pivotally mounted about a lever pivot axis 659 to transporter 600 near the intersection of body 602 and flange 604b. First lever projection 656 is substantially perpendicular to flange 604b and abuts lever tab 630b on X-axis positioning arm 622b for actuating the positioning lever. Second lever projection 658 also is substantially perpendicular to flange 604b and includes an edge 660 for contacting a sample container.

Transporter 600 functions as follows. For loading, the transporter occupies a loading position substantially outside a housing. In this position, actuator tabs 636a,b abut an actuator bar 670, shown in FIG. 43. In addition, biasing springs 642a,b are compressed, and bumper 632 and second projection 658 having edge 660 are pulled out of cavity 608.

A person, robot, or mechanical stacker then can place a sample container into cavity 608 so that the bottom of the sample container rests on shelves 610. Cavity 608 is larger than the sample container to facilitate this placement and to accommodate variations in sample container size.

In some configurations, connector portion 607 may be removed, such that transporter 600 has an open end. This open end permits a microplate transfer device to enter cavity 608 and the generally rectangular area of the holder. The microplate transfer device may, after moving into the generally rectangular area, move down relative to transporter 600, thereby gently placing the microplate into the generally rectangular area.

For reading, the transporter must deliver the sample container to an examination site inside the housing. In this process, the transporter moves parallel to second end segments 634a,b, and actuator tabs 636a,b disengage actuator bar 670. Biasing spring 642a pushes Y-axis positioning arm 622a toward cavity 608. Bumper 632 engages the sample container and pushes it away from body 602 until it abuts extensions 606a,b. Biasing spring 642b pushes X-axis positioning arm 622b toward cavity 608. Edge 660 of second projection 658 engages the sample container and pushes it away from flange 604b until it abuts flange 604a.

As long as the sample container is placed in any position on the lower guide shelves, it may be positioned (registered) precisely and reproducibly against a reference corner 672 within cavity 608 under the action of both positioning arms. Biasing springs 642a,b can be chosen to have different strengths, so that the X-Y positioning action is performed less or more forcefully. In analyzer 50, middle segment 638b and first lever projection 656 of positioning lever 654 can be varied in length to cause registration to occur in series, first along the X-axis or first along the Y-axis, and second along the Y-axis or second along the X-axis, respectively. For example, reducing the length of middle segment 638b and reducing the length of projection 656 will cause registration to occur first in the X-axis, and second in the Y-axis.

Positioning lever 654 and bumper 632 are retracted when body 602 of the automatic microplate positioning transporter is moved to the eject position by the X,Y stage. Thus, the microplate is placed on transporter shelf 610 only when the lever and bumper are retracted. Two springs 642a,b are attached to the rods, which run along the length of the transporter body and end perpendicular to the body. When the transporter is moved to the eject position, the two perpendicular ends of the rods encounter a stop 670, which consists of a rectangular structure located above and parallel to the body. The stop prevents the two perpendicular ends of the actuators, and thus the actuators, from moving with the transporter body. This causes the two springs to contract, changing the position of the transporter arms and increasing the amount of room for the microplate. The microplate then can be placed on the guide shelf of the body. When the body of the automatic microplate positioning transporter is moved back away from the stop, the two perpendicular ends of the actuators no longer are blocked, which allows the actuators, springs, and transporter arms to move into their original position. The expansion of the springs pushes the microplate exactly into position, as defined by the reference corner.

Thus, components of transporter 600 act as first and second releasable clamp mechanisms. The first releasable clamp mechanism applies a force against a first (e.g., Y or X) side of the microplate, thereby securing the microplate in the holder. The second releasable clamp mechanism applies a force against a second (e.g., X or Y) side of the microplate, thereby securing the microplate in the holder from two sides. These clamp mechanisms may sandwich a microplate between the positioning arms and opposing portions of the frame structure, such that the positioning arms function as pushers and the opposing portions of the frame structure function as bumpers for the clamp mechanisms.

The invention provides a method of automatically feeding microplates in and out of an analyzer. The method comprises (1) automatically delivering a microplate just outside an opening to the analyzer, (2) moving a gripping device from inside the analyzer, through the opening, to a location immediately below the microplate; and (3) gently placing the microplate onto the gripping device. The method further may comprise clamping the microplate in the holder by applying a first force against a first side of the microplate, applying a second force against a second side of the microplate, and/or serially performing the clamping steps.

Figure 43:
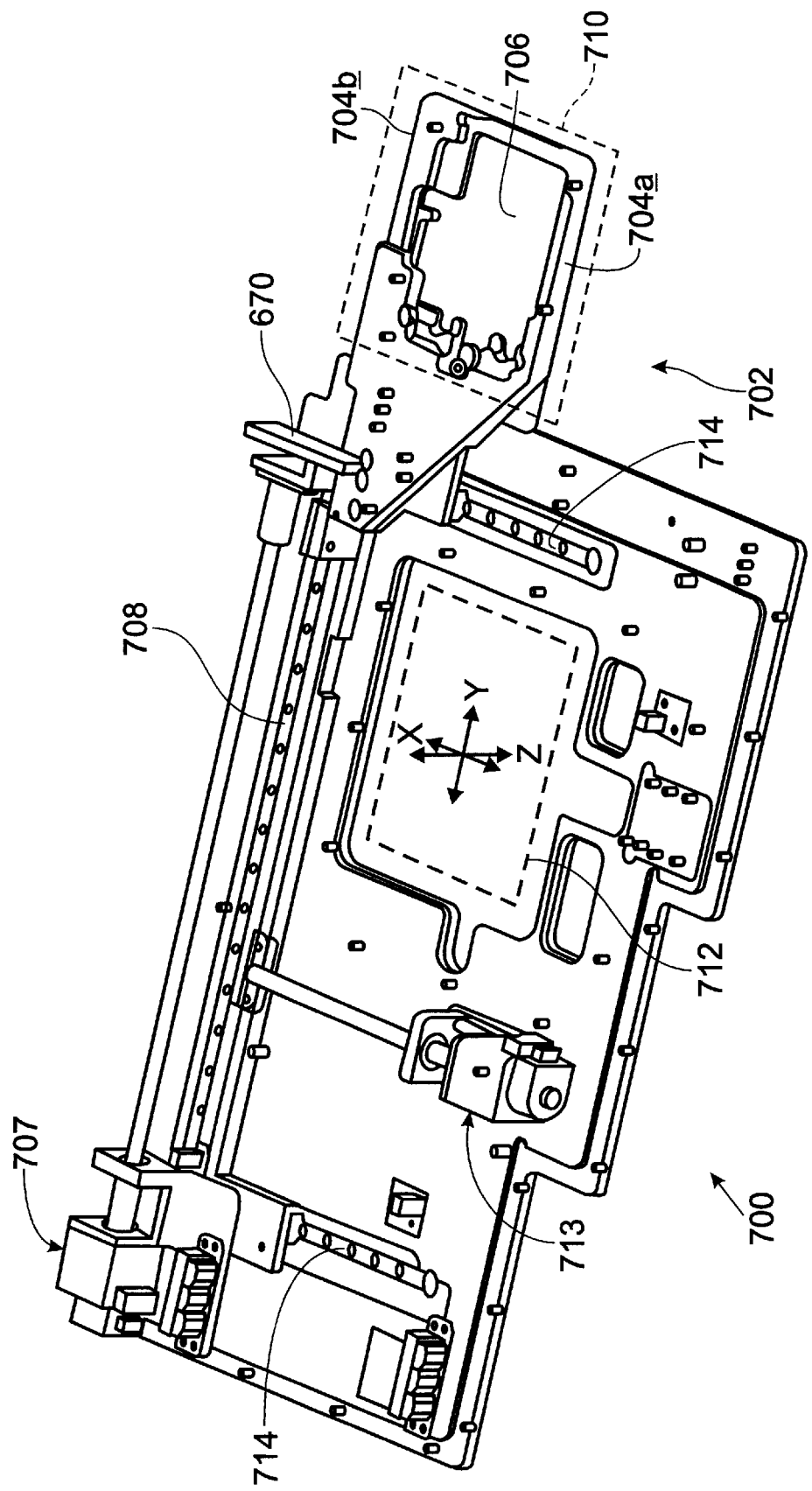
FIG. 43 is a perspective view of a base platform and associated drive mechanisms for moving a transporter along X and Y axes relative to the base platform.

FIG. 43 shows a base platform 700 with drive mechanisms for moving a transporter 702 between loading and examination positions or sites. As previously described, transporter 702 includes flanges 704a,b defining a cavity 706 for receiving and gripping a microplate (not shown). A Y-axis drive mechanism 707 is provided for moving transporter 702 along a first track 708 relative to the Y-axis, from a loading position 710 toward an examination position 712. An X-axis drive mechanism 713 is provided to move transporter 702 to examination position 712 along a second track 714 relative to the X-axis.

In operation, a microplate is loaded in transporter 702 at loading position 710. Transporter 702 is driven toward the examination position by Y-axis drive mechanism 707. A sensor (not shown) detects the presence of the sample container. The analyzer may be configured automatically to read the microplate once the sensor detects its presence, or the analyzer may be configured to signal the system controller through a data port that a microplate has been received and that the analyzer is ready to accept a command to begin reading. The X- and Y-axis drive mechanisms then operate together to align selected microplate wells with an optical axis, substantially parallel to a Z-axis, along which a sensed volume for luminescence detection may be defined by optical components contained in one or both of a top and bottom optics head positioned above and below base platform 700, respectively.

Transporter 700 thus may function both as a sample delivery device in and out of the analyzer, and as a moveable stage for supporting the sample container at the examination site. The cavity in the transporter permits analysis to be carried out from below the holder, when the transporter is functioning as a stage at the examination site.

X- and Y-axis drive mechanisms 707 and 713 may be controlled by a high-performance motion control system that maximizes throughput while minimizing detection errors. A preferred high-performance control system includes precision five-phase stepper motors that employ encoder feedback to move the microplate quickly and accurately to each read position. The control system may optimize the acceleration/deceleration profiles of the microplate to minimize shaking of fluid within the microplate, for example, by minimizing "jerk" (the time rate of change of the acceleration of the microplate). Alternatively, the control system may increase throughput by moving plates more quickly, if higher variation in results due to increased shaking and settling time may be tolerated.

Exterior Features

Figure 44:
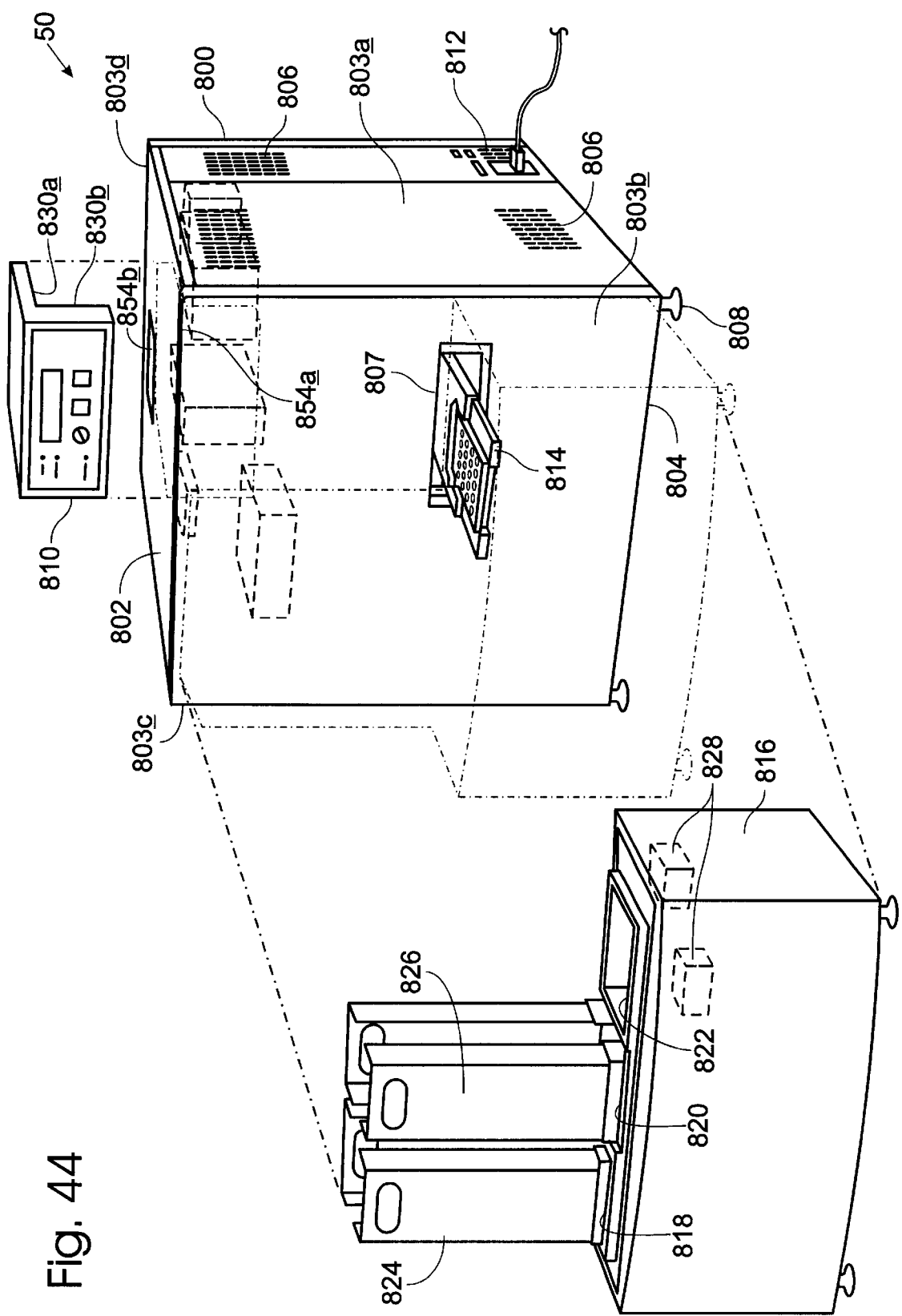
FIG. 44 is a partially exploded perspective view of a housing for an analyzer constructed in accordance with the invention.

FIG. 44 shows a high-throughput luminescence analyzer 50 constructed in accordance with the invention. Components of the analyzer are maintained in a housing 800, both for organization and for protection. Housing 800 is substantially rectangular and includes light-tight exterior top 802, side 803*a–d*, and bottom walls 804 that reduce background in luminescence measurements. The walls may include vents 806 to facilitate air flow through the analyzer and a transporter port 807 for sample input/output. Housing 800 also may include feet 808 to support the analyzer and to permit air flow between the analyzer and any support structure on which the analyzer is placed.

Analyzer 50 is substantially automated. The analyzer is designed so that user interactions occur primarily through a control unit 810, an electronic input/output panel 812, and a break-out box (not shown), each of which supports a variety of input/output functions. The analyzer also is designed so that sample input/output occurs primarily through a transporter/stage 814 and an optional sample feeder 816.

Transporter 814 generally comprises any device for supporting a sample container, as described above. In analyzer 50, transporter 814 moves between the interior and exterior of the analyzer, and may be used alone or together with sample feeder 816 for sample input/output.

Sample feeder 816 generally comprises any device for automatically processing multiple samples, as described below. In analyzer 50, sample feeder 816 includes a first (input) station 818 for holding sample containers to be read, a third (output) station 820 for holding sample containers that have been read, and a second (direct transporter access) station 822 for inputting or outputting sample containers that bypasses the input and output stations. Input and output stations 818, 820 accommodate preprocessing and postprocessing sample containers bins 824, 826 that hold and organize stacks of sample containers before and after reading, respectively. Sample feeder 816 also may include a barcode reader 828 for automatically identifying labeled sample containers.

The sample container generally comprises any container for holding at least one sample. Preferred sample containers include microplates. Other suitable sample containers include any sample containers having a shape and rigidity suitable for processing in an analyzer, such as slides or supported gels.

Control unit. Control unit 810 generally comprises any interface used for direct input/output functions. The control unit may be integrated into the analyzer, or it may be a separate unit that can be positioned away from the analyzer or affixed to the analyzer at one or more locations. The control unit also may include more than one unit, each dedicated to different input/output functions or to use at different locations.

The control unit 810 may be used in conjunction with a host computer for a variety of input/output functions. For example, the control unit may be used to input commands, such as signals to start and stop the instrument. Similarly, the control unit may be used to display output information, such as instrument status, instrument diagnostics, measurement results, and other information generated by the analyzer in different assay modes. The control unit is especially useful for automated operations that require manual user intervention.

Figure 45:
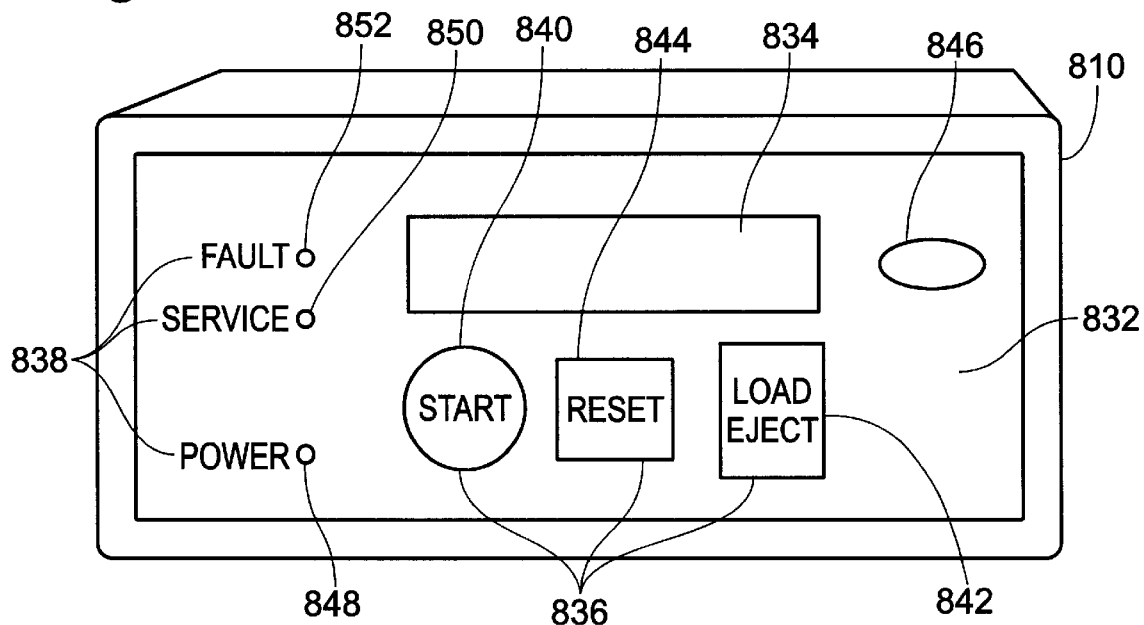
FIG. 45 is a front view of the control unit shown in FIG. 44.

FIG. 45 shows an enlarged isolated view of control unit 810 of analyzer 50. Control unit 810 is a separate unit that statically or swivelably affixes to the analyzer at any one of a plurality of docking locations. Control unit 810 is substantially L-shaped, with substantially perpendicular inner surfaces 830*a,b* that mate with adjacent substantially perpendicular walls of the analyzer including top wall 802 and one of side walls 803*a–d*, although other shapes are possible. In its preferred orientation, control unit 810 is mounted so that front face 832 is substantially parallel with one of side walls 803*a–d* of analyzer 50.

Control unit 810 includes various data input and output components. Front face 832 includes a gas-plasma display 834, keypad 836, and indicator lights 838. Control unit 810 also may include additional and/or alternative components, and their relative organization may deviate from that shown in the drawings and discussed below. Gas-plasma display 834 is located in the upper center of front face 832 and is used to provide messages regarding instrument status. Additional displays and/or alternative display formats, such as light-emitting diodes (LEDs) and liquid crystal displays (LCDs), also may be used.

Keypad 836 is located below and to the right of gas-plasma display 834 and includes four keys. A "start" key 840 initiates the sample-reading process. A "load/eject" key 842 loads or ejects a sample container, such as a microplate, depending upon the current status of the instrument. A "reset" key 844 reinitializes the instrument, sending motors to their home positions and turning off the audible alarm. A "status" key 846 alters the state of a continuous light source or activates reverse stack. Additional keypads and additional and/or alternative keys also may be employed. Alternative methods of data entry, such as a computer mouse or touch screen, also may be employed.

Indicator lights 838 are located to the left of the display and keypad. A "power" light 848 indicates that power is being supplied to the instrument. A "service" light 850 indicates that a service procedure is needed, such as changing a light source. A "fault" light 852 indicates that a critical fault has occurred, which is a fault that requires intervention by an operator. Additional and/or alternative indicator lights also may be provided.

Control unit 810 also may include audio signals. For example, an audible alarm within the interior of control unit 810 may sound in the event of a critical fault.

Alternative audio signals, such as prerecorded or synthesized voice messages, also may be used.

Control unit 810 may be moved between at least two control interface docking-panel mounting locations 854*a,b* on the instrument. A first docking location 854*a* is located near an upper edge of sample input side 803*b* of housing 800. This configuration is especially suitable for manual operation, because control unit 810 and transporter port 807 are positioned on the same side of analyzer 50. A second docking location 854*b* is located near an upper edge of back side 803*d* of housing 800. This configuration is especially suitable for robotic operation, because control unit 810 and transporter port 807 are positioned on opposite side of analyzer 50, facilitating robotic access to transporter port 807. Such flexible positioning permits commands to be entered and status information, diagnostic information, measurements, and other information to be read from multiple positions. Flexible positioning is especially convenient when one or more sides of the analyzer are blocked due to analyzer placement or nearby peripherals. Alternatively, it permits two or more control units to be connected at once, increasing convenience and flexibility.

Figure 46:
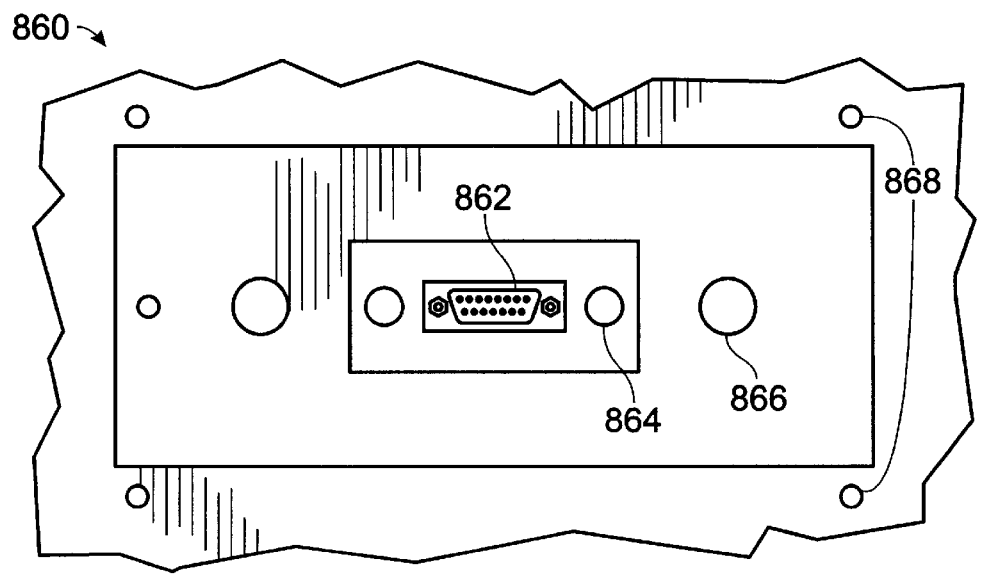
FIG. 46 is a top view of one of the control interface docking locations shown in FIG. 44.

FIG. 46 shows a control interface docking location 860. Control unit 810 includes an electronic connector prong, which can be mated with an electronic connector port 862 at docking location 860. Electronic connector port 862 is connected to a host computer, allowing the computer to communicate with the control unit, so that a user can control the analyzer by inputting information through the control unit. Electronic connector port 862 preferably includes an RS-232 serial port, and preferably is connected to the host computer through an RS-232 cable. Control unit 810 also includes other mating structure, including substantially cylindrical prongs that match with receptors 864 and latches 866, and indentations that match with dimples 868, at docking location 860. Positioning docking location 860 at sites 854a,b on top wall 802 of housing 800 reduces the stress on the mating structure when the control unit is mounted; however, docking location 860 also can be positioned at other sites on or off housing 800.

Input/output panel. The input/output panel generally comprises any ports used for basic input/output functions. These include ports for providing and controlling power input to the analyzer, and for inputting and outputting data and commands. Components of the input/output panel may be collected for convenience in one location or positioned at various locations on the analyzer.

Figure 47:
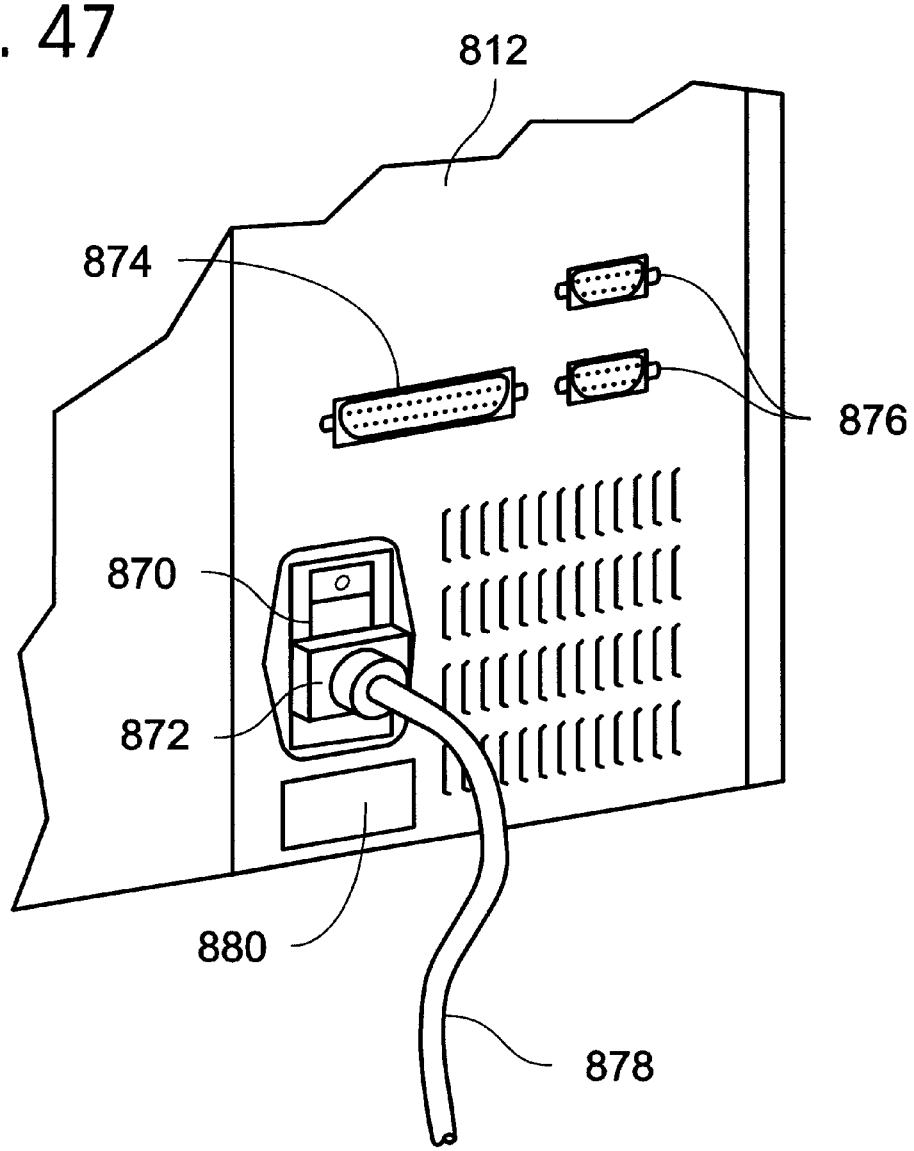
FIG. 47 is a front view of the input/output panel shown in FIG. 44.

FIG. 47 shows an enlarged isolated view of control input/output panel 812. In analyzer 50, input/output panel 812 includes a power switch 870, power entry module 872, auxiliary port 874, and two RS-232 serial ports 876. Power switch 870 is located in the left center of the panel and is used to actuate analyzer 50. Power entry module 872 is located below the power switch and is used to supply power to analyzer 50; power arrives via a standard electrical cord 878 that may be plugged into a wall socket. Auxiliary port 874 and serial ports 876 are located above and to the right of the power entry module and are used for input/output. These ports provide flexibility, because they permit the analyzer to communicate with several different peripherals. Additional power entry modules and additional and/or alternative communication ports for input/output in alternative formats and positions also may be used. A model/regulatory label 880 containing written information regarding the analyzer is provided below power entry module 872 on the input/output panel.

Break-Out Box. The analyzer also may include an external "break-out" accessory box connected to the instrument with a cable. The break-out box may include a connection block that allows the analyzer to provide a general purpose and hard-wired electrical interface to external devices, such as lamps, warning alarms, enunciators, associated instruments, and external system controllers. Through the break-out box, the instrument's software can be programmed to send or receive control signals from external systems or to control or provide signals to external devices. These control signals can be conditioned on the occurrence of predetermined internal events, such as when the analyzer finishes reading a plate or when a fault such as a mechanical jam occurs. Through the break-out box, the instrument also can accept signals from external devices or controllers to start reading a plate or perform other programmable functions.

Sample Feeder

Figure 48:
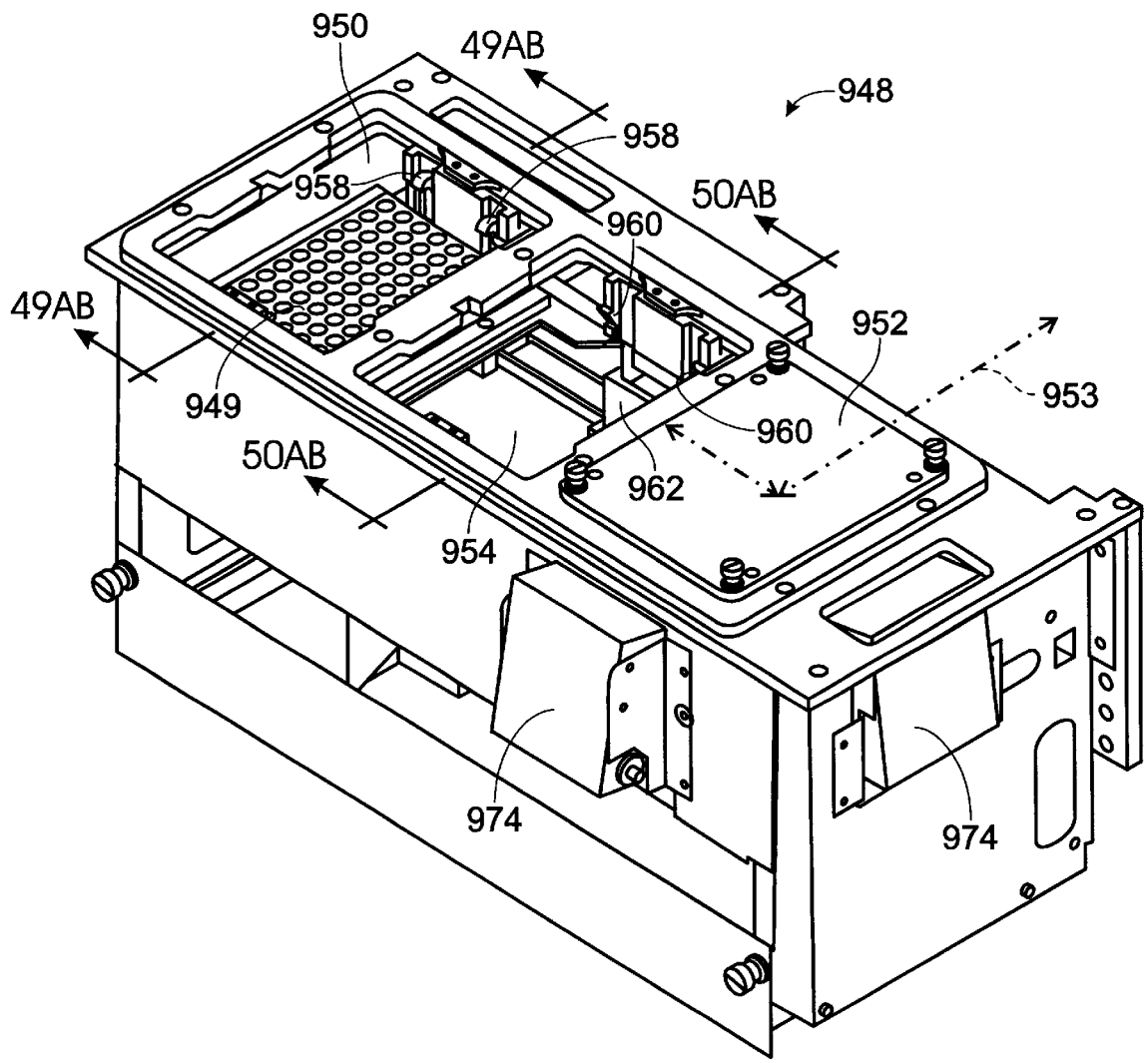
FIG. 48 is a perspective view of a sample feeder constructed in accordance with the invention, with bins removed so that internal mechanisms of the sample feeder can be viewed.

FIGS. 48–50 show a sample feeder 948, which generally comprises any mechanism for automatic processing of multiple sample containers. Sample feeder 948 enhances convenience by reducing the amount of human intervention required to run the analyzer. Sample feeder 948 also enhances throughput by reducing the amount of time required to process multiple sample containers.

Generally, sample feeder 948 operates as follows. Before reading, a robot (1) removes a sample container from the bottom of an input stack of sample containers at an input station, (2) transports the sample container to a direct transporter access station, and (3) transfers the sample container to a transporter. After reading, the robot (1) takes the sample container from the transporter, (2) transports the sample container to an output station, and (3) transfers the sample container to the bottom of an output stack of sample containers. Sample feeder 948 requires only two motors to provide these functions with high throughput (~5 seconds for load and unload time).

FIG. 48 shows sample feeder 948 with its preprocessing and postprocessing bins removed, so that internal mechanisms can be viewed. A microplate 949 is loaded from the bottom of a stack of microplates in the input bin into a first (input) station 950. Microplate 949 then is transported on a tray (not shown) to a second (direct transporter access) station 952, where the microplate is handed off to a transporter (not shown). The transporter transports microplate 949 generally along an axis 953 to an examination site inside the analyzer. After analysis, the transporter transports microplate 949 back along axis 953 generally in the opposite direction to second station 952. Microplate 949 then is handed back to the tray, and transported to a third (output) station 954, where the microplate is added to the bottom of a stack of microplates in an output bin.

In analyzer 50, a first linear path defined by axis 953 connects the examination site to the second station, and a second linear path connects the first second and third stations, wherein the first linear path is substantially perpendicular to the second linear path. However, analyzer 50 also may have other configurations. For example, the examination site and the first, second, and third stations may all be positioned along a single substantially linear path.

In input station 950, a combination of two lifters and four latches cooperate to singulate or pick a single microplate from the bottom of a stack. (These lifters are concealed by microplate 949 in FIG. 48.) Latches 958 have pick portions that extend into the cavity of first station 950 and support a stack of microplates. Latches 958 are disposed toward the microplates by configuring the latch to have a center of gravity above and inward relative to a pivot point. As the lifters are raised in the input station, the pick portions of the latches are pushed out of the way, so that the microplate can be supported and lowered by the lifters. After one microplate has passed below the latch, latches 958 move back into a supporting position relative to the remainder of the stack.

In output station 954, a different latch configuration is employed. Latches 960 are urged inward toward the microplates by a spring (not shown). When lifter 962 lifts a microplate against latches 960, the microplate pushes the latches out of the way. After one microplate has passed above the latch, latches 960 move back into a supporting position relative to the remainder of the stack.

Figure 49A:
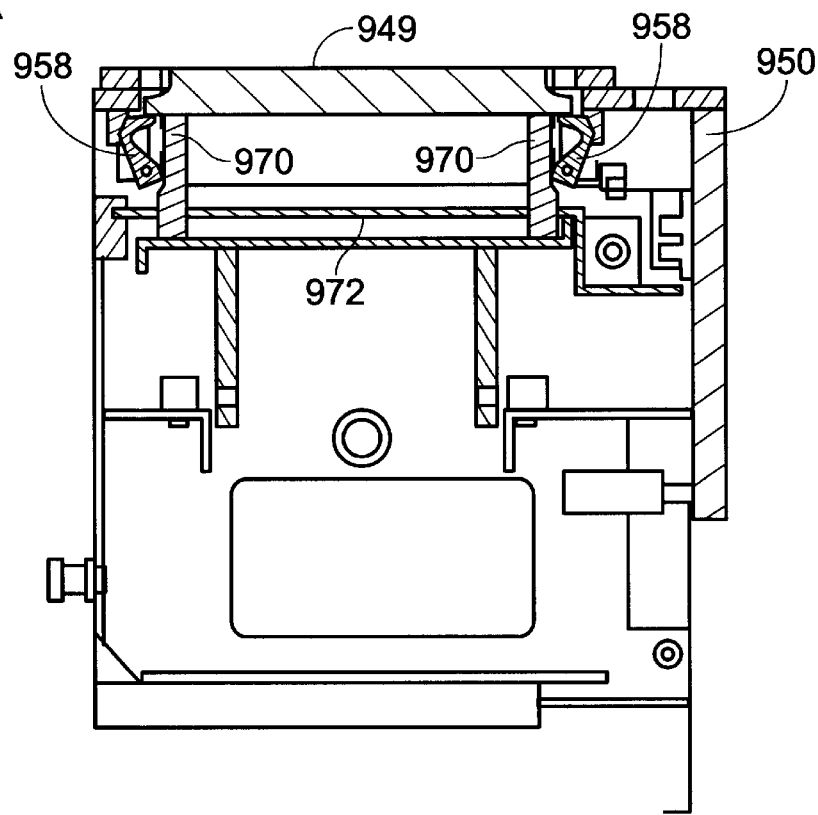
FIGS. 49A and 49B are cross-sectional views through a first (input) station of the sample feeder shown in FIG. 48, taken generally along the line 49AB—49AB in FIG. 48 and showing latch and lifter cooperation to remove a microplate from the bottom of a stack.
Figure 49B:
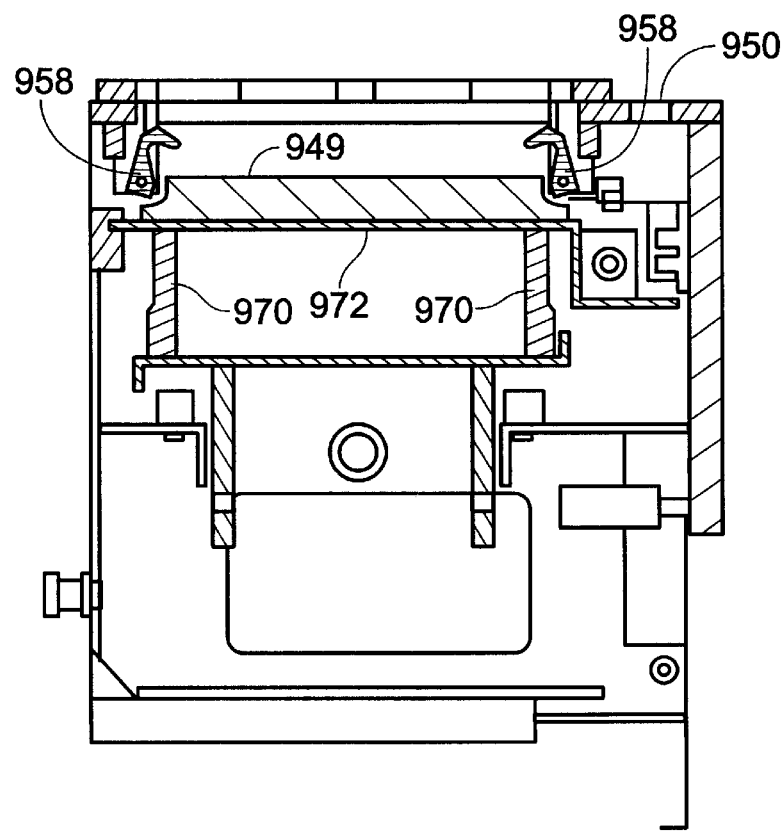

FIGS. 49A and 49B show how input station 950 operates. FIG. 49A shows microplate 949 as it is being picked up at input station 950 prior to analysis. Lifters 970 have moved up through holes in tray 972 to contact the bottom of microplate 949, and in the process have pushed latches 958 out of the way. FIG. 49B shows the same structures as FIG. 49A, except that lifters 970 have dropped, thereby lowering microplate 949 onto tray 972 for transport to the analyzer. Pick portions of latches 958 have moved back into the cavity to support the remainder of the stack.

Figure 50A:
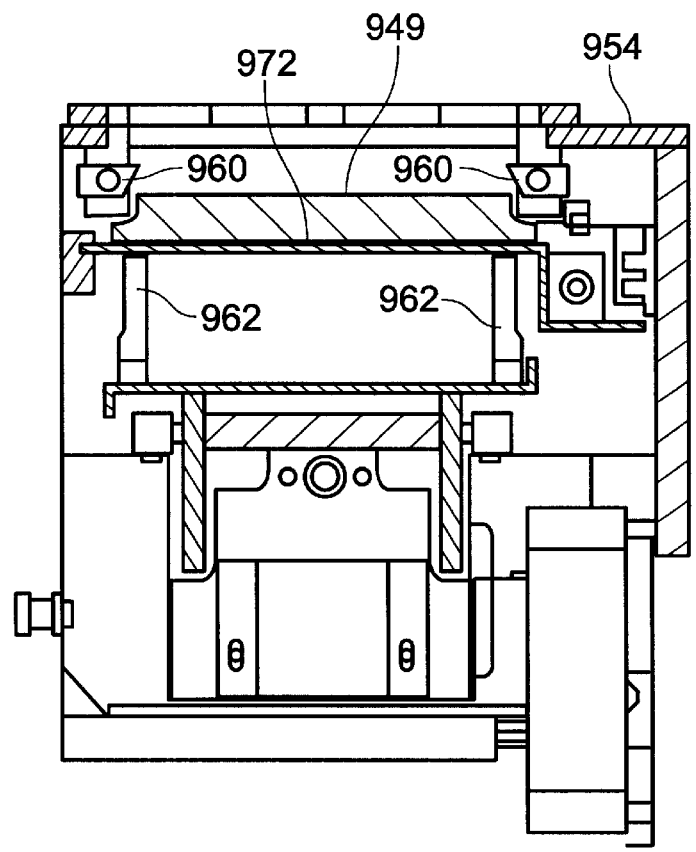
FIGS. 50A and 50B are cross-sectional views through a third (output) station of the sample feeder shown in FIG. 48, taken generally along the line 50AB—50AB in FIG. 48 and showing latch and lifter cooperation to add a microplate to the bottom of a stack.
Figure 50B:
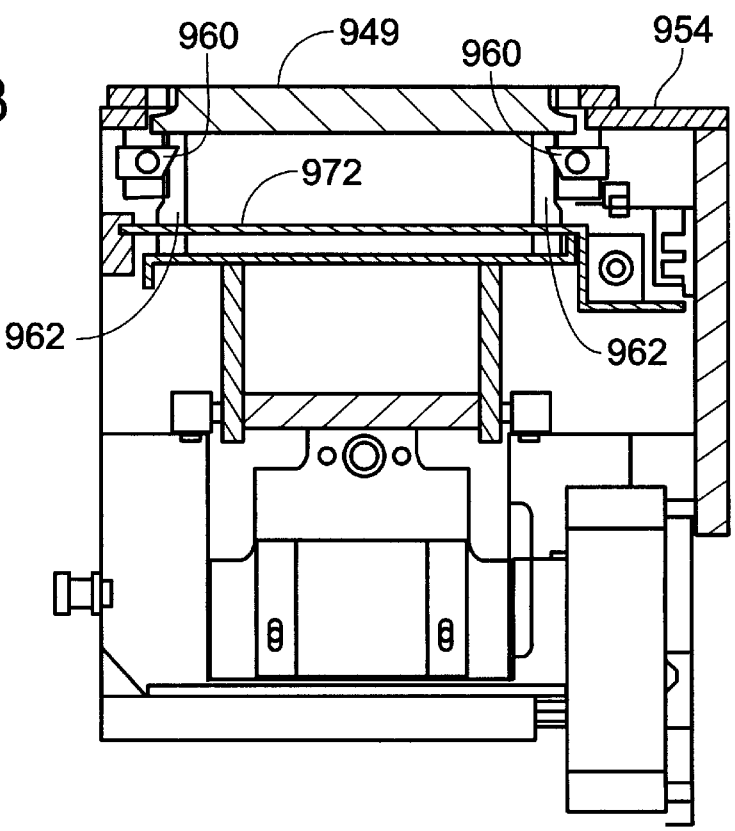

FIGS. 50A and 50B show how output station 954 operates. FIG. 50A shows microplate 949 after it has been delivered to output station 954 following analysis. Lifters 962 then move through holes in tray 972 to raise microplate 949 toward a stack of microplates in the output bin (not shown). FIG. 50B shows the same structures as FIG. 50A, except that lifters 962 have raised microplate 949 past latches 960. Latches 960 are spring biased toward the cavity of third station 954. As lifters 962 raise microplate 949, latches 960 are pushed out of the way by the outer contour of microplate 949. Once microplate 949 is above latches 960, the latches return to their inward position to support the stack of microplates in the output bin. Lifters 962 then retreat downward completely out of the holes in tray 972, so that the tray can translate back to input station 950 to collect another microplate for delivery to the analyzer.

Figure 51:
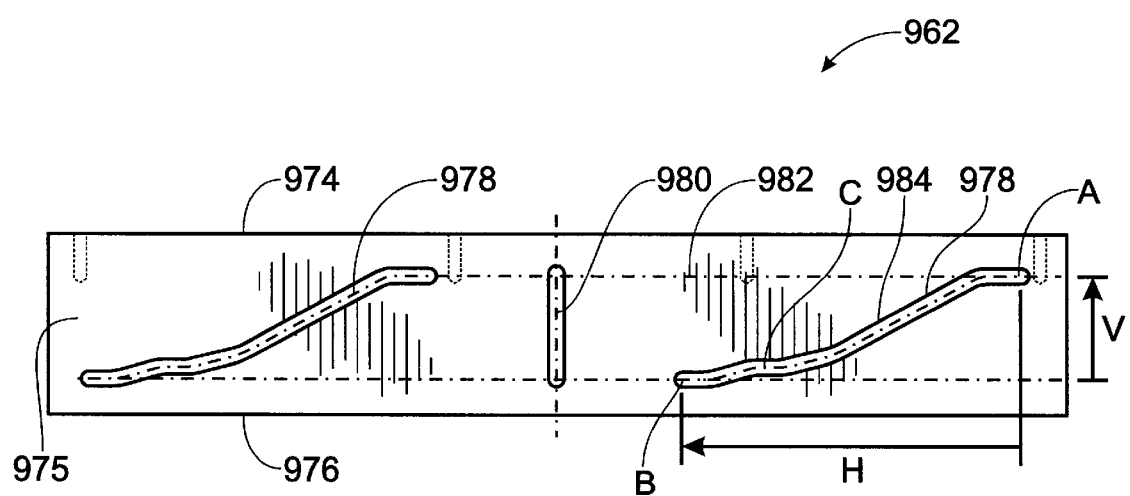
FIG. 51 is a side elevation view of a lifter from the sample feeder shown in FIG. 48.

FIG. 51 shows how lifter 962 operates. Generally, the lifter comprises any mechanism configured to raise or lower a sample container. Lifter 962 is substantially rectangular and includes top 974, side 975, and bottom 976 walls. Each of an opposed pair of side walls 975 includes two sloped drive channels 978, which function as cams, and a vertical guidance channel 980. In sample feeder 948, pins are inserted into drive channels 978 and guide channel 980. In alternative embodiments, pins and channels may be replaced with other components, including ridges, bearings, or rollers. Pins inserted into drive channels 978 are connected to a drive motor, which moves the pins through drive channels 978 between a top position A nearer top wall 974 and a bottom position B nearer bottom wall 976. The pins move horizontally along a line 982, so that the pins push against a side 984 of drive channels 978, urging lifter 962 to move both horizontally and vertically. Pins inserted into guidance channels 980 are connected to relatively fixed portions of sample feeder 948, preventing horizontal motion, but permitting vertical motion, so that lifter 962 only moves vertically. As the pin moves between positions A and B, the pin moves a horizontal distance H and a vertical distance V. It is the vertical displacement that creates the raising and lowering motions. H and V may be optimized for particular sample containers and travel distances; in sample feeder 948, H and V are optimized for microplates and are approximately 10 cm and 3.5 cm, respectively. Lifter 962 is raised when the pin is near position A, and lifter 962 is lowered when the pin is near position B.

In use, the drive motor moves the pins horizontally at a substantially uniform rate; consequently, the slope of drive channel 978 determines the mechanical advantage and the rate of vertical motion. Near positions A, B, and an intermediate position C, the slope of drive channel 978 is substantially zero, so that there is substantially no vertical motion. Stated differently, near positions A, B, and C, a preselected vertical position corresponds to a range of horizontal positions. This configuration makes the vertical position relatively insensitive to motor precision or manufacturing tolerance, because the lifter will be at the same vertical position whenever it simply is near positions A, B, or C. Between positions A and C, and between positions B and C, the slope of drive channel 978 is nonzero, so that there is vertical motion. The slope is largest (approximately 30°) between positions A and C, so that the lifter raises and lowers relatively rapidly when it is farthest from the bottom of the stack of sample containers. The slope is smallest (approximately 15°) between positions B and C, so that the lifter raises and lowers relatively slowly when it is nearest to the bottom of the stack of sample containers.

The drive motor generally comprises any mechanism configured to generate a driving motion. The drive motor used in sample feeder 948 is a stepper motor, which generates a constant torque. Generally, stepper motors and cams provide alternative mechanisms for performing the same function, in this case, generating a varying rate of motion. However, pairing a stepper motor and cam together in the invention provides several advantages. In particular, the cam provides mechanical advantage and positional insensitivity, and permits the stepper motor to be run at a constant, optimal speed. If the stepper motor were used alone, an electronic control system would be necessary to vary raising and lowering speed. Conversely, if the cam were used alone, with a nonstepper motor, an electronic control system with feedback control would be necessary to vary raising and lowering speed.

Together, the lifters and latches form a singulation mechanism configured to separate a microplate (or other sample container) from a stack of microplates in the down-stacking or input operation. This mechanism has inherently low sensitivity to the exact size, shape, construction material, and surface finish of the microplate. As described, the invention may include four inwardly sloping, tapered (or angled) latches that cause the stack of microplates to self-center within the microplates input area to accommodate both relatively small and large microplates sizes. Also as described, the invention may include a feature that causes the microplates to drop gently when the singulation mechanism disengages from the edges of the microplates, thus allowing the microplates to drop onto the lifter mechanism support structure, which lowers the microplates to the tray without spilling fluid from the wells.

The down-stacking latches pivot on pins and are actuated by the lifter mechanism so as to retract when the lifter mechanism rises, thereby releasing the bottom microplate from the stack and allowing it to drop softly onto the lifter. When the latches retract, they pivot on their support pins such that their centers of gravity are offset. Consequently, when the lifter mechanism is lowered, the latches will be activated by gravity to return to their nonretracted or extended state, thereby preventing the next microplates in the stack from dropping as the lifter mechanism is lowered. Because the offset in the center of gravity of the latches is only enough to cause them to return to their extended position, they press only very lightly on the edges of the microplate as it drops. Because the ends of the latches are polished smooth, they exert only a small frictional force on the edges of the microplates so as not to cause the microplate to tilt or otherwise hang up as the lifter mechanism is lowered and the microplate is placed on the tray.

Together, the lifters and latches also form a stacking mechanism configured to add a microplate to a stack of microplates. Generally, the up-stacking mechanism resembles the down-stacking mechanism. The lifter mechanism raises the microplate by a fixed amount, thereby causing it to pass by four spring-loaded latches, which retract as the microplate is raised by the lifter. Once the bottom of the microplate is above the top of the latch, the latches are released, and a spring on each latch causes the latch to extend under the microplate. The lifter mechanism then is lowered, causing the microplate to be captured by the now extended latches. The up-stacked microplate thus is added to the bottom of the output stack.

Sample feeder 948 also may employ alternative singulation mechanisms. For example, singulation mechanisms may (1) take microplates from the bottom of the stack in the input station and add microplates to the bottom of the stack in the output station, as above, (2) take microplates from the bottom of the stack in the input station and add microplates to the top of the stack in the output station, (3) take microplates from the top of the stack in the input station and add microplates to the bottom of the stack in the output station, or (4) take microplates from the top of the stack in the input station and add microplates to the top of the stack in the output station.

Sample feeder 948 permits a robot to deliver a sample container to the input station and to retrieve a different sample container from the output station, both in the same trip. This feature is known as "process compression" and reduces robot hand travel in servicing analyzer 50. For example, if there were only one loading station (e.g., the transporter), the robot would have to remove the analyzed microplate before delivering the unanalyzed microplate. Thus, process compression replaces two separate robot movements with one robot movement. Sample feeder 948 may be configured so that the input and output stations can hold a microplate to facilitate process compression.

Sample feeder 948 is designed to be flexible. The input and output stations can accommodate a variety of commercially available microplates and are large enough to allow microplates to be placed in them by a robot or a human hand. Suitable microplates typically have 96 or 384 wells, but other configurations also can be accommodated. The input and output stations also can accommodate a variety of commercially available preprocessing and postprocessing microplate bins for holding a stack of microplates before and after analysis, respectively. Preprocessing bins may be removed from the input station and replaced with another preprocessing bin containing a new stack of microplates with samples to be analyzed. Similarly, postprocessing bins positioned may be removed from the output station and replaced with another postprocessing bin to receive a new stack of microplates with samples that have been analyzed. Microplate bins may be used with other robotics to dispense, wash, and read without restacking microplates. Suitable microplate bins typically can accommodate 0–60 microplates.

Sample feeder 948 also may include a barcode reader, as shown in FIG. 48, which can be used automatically to identify labeled microplates. The barcode reader 986 preferably is positioned in either of two positions adjacent direct transporter access station 952; these positions permit barcode reader 986 to read barcodes mounted on the long edge or the short edge of microplates. Barcodes are read when sample feeder 948 moves the microplate from input station 950 to direct transporter access station 952. Barcodes cannot be read when microplates are delivered directly to the direct transporter access station 952. Barcode reader 986 can be programmed to decode a variety of symbologies, including SPC (EAN, JAN, UPC), Code 39 (3–43 digits), Codabar (3–43 digits), Standard 2 of 5 (3–43 digits), Interleaved 2 of 5 (4–43 digits), Code 93 (5–44 digits), and MSI-Plessey (4–22 digits), among others. Information obtained from the barcode can be used for various purposes. For example, the barcode can be used to name the report file. The barcode also can be used to convey instructions to the analyzer relating to required changes in assay mode or optics configuration.

Analyzer Set-Up, Calibration, and Reading

Operation of the analyzer includes set-up, calibration, and reading. Setup of the analyzer includes selection of an assay mode and selection of optical components and conditions to optimize performance in that assay mode. Selection of optical components and conditions requires knowledge of the assay mode, microplate, fluid level total fluid volume, and sensed volume, among other parameters. Optical components may be changeable manually or automatically, depending on the component. For example, the size of the sensed volume may be adjusted manually by replacing the fiber optic cables adjacent the examination area, and manually or automatically by changing the apertures in front of the fiber optic cables. Similarly, the position of the sensed volume may adjusted manually, or automatically by scanning a positive control well or wells to obtain the maximum signal given the average fluid level in the wells. Manually changeable components may include standard or "quick-change" components.

Calibration of the analyzer may include using a calibration plate. A calibration plate may be shaped like a microplate and include features that can be manually, optically, mechanically, and/or electronically recognized. For example, a calibration plate may include precisely located apertures, mirrors, light sources (such as light-emitting diodes (LEDs)), and/or fluorescent reference standards to verify that the optics, detection, and positioning systems are operating properly.

Reading by the analyzer may be performed in five phases. Phase 1 comprises loading a microplate in the transporter. During this phase, a person, robot, or microplate feeder mechanism places the microplate on the microplate transporter of the X,Y stage. A computer-controlled X-Y microplate registration mechanism ensures that microplates have the correct alignment relative to the optics beam.

Phase 2 comprises sensing the microplate in the transporter. During this phase, a sensor is activated that tells the local or system controller that the microplate has been delivered. The local controller can begin reading the microplate either after sensing the microplate or after receiving a command from the system controller to start reading.

Phase 3 comprises finding the top of the microplate. During this phase, the top of the microplate is found with the top-of-the-plate sensor located in the optics head, followed by computercontrolled adjustment of the Z-position of the optics head.

Phase 4 comprises reading the microplate. During this phase, the microplate is moved automatically from well to well to allow analysis of the contents of each well by use of a high performance motion control system with preselected acceleration/deceleration profiles and settling times to provide maximum possible throughput with minimum acceptable read error.

Phase 5 comprises unloading the microplate from the transporter.

Assay Modes

The analyzer may support a variety of assay modes, including (1) luminescence intensity, (2) luminescence polarization, (3) time-resolved luminescence, (4) chemiluminescence, and (5) absorbance. Aspect of these assay modes are described below to show the versatility and sensitivity of the analyzer. Additional assays and/or alternative methods for performing the described assays also may be employed in conjunction with the analyzer provided by the invention. Additional information regarding these assay modes may be found in U.S. Provisional Patent Application Serial No. 60/082,253, filed Apr. 17, 1998, and incorporated herein by reference.

Luminescence Intensity Mode. Luminescence intensity measurements use a continuous light source. Light produced by the light source is routed through a luminophore-specific excitation filter and a low-luminescence fiber optic cable to the optics head. A beamsplitter splits the light, reflecting light into the assay well and transmitting light into a light monitor. The light monitor checks the light source continuously and can be programmed to alert the user if the light source fails. Light emitted from the assay well may pass back through the beamsplitter and then is routed through a fiber optic cable to an emission filter that conditions the light before detection by a photomultiplier tube.

The analyzer may use confocal optics elements to direct excitation light into the assay well and to detect light emitted from the well, all from a sensed volume that may be small compared to the overall volume of the well. Because the sensed volume does not change with the volume of the assay well, performance in different microplates is virtually identical. Z-position within the well may be set manually or automatically. For homogeneous assays, the location with the highest signal-to-noise (S/N) ratio and highest signal-to-background (S/B) ratio typically is in the middle of the well. For cell-based assays, the location with the highest S/N and S/B ratio typically is at the bottom of the well, where luminescence from the cells is maximized and luminescence from the fluid is minimized. Conditions that optimize the S/N and S/B ratios may be determined empirically.

Luminescence intensity measurements may be made from either the top or bottom of the sample well. Bottom reading delivers a higher signal than top reading because the bottom focal area is larger, but bottom reading also delivers a lower S/N ratio because microplates or other sample containers typically autoluminesce.

The user has full control of analyzer settings through software. For luminescence measurements, the user selects the excitation and emission filters, top or bottom reading, and read time. Optional parameters include the magnitude and duration of plate shaking, well-to-well settle time, and Z-height adjustments.

Luminescence Polarization Mode. Luminescence polarization measurements use the same optical configuration as luminescence intensity measurements, except that polarization measurements always employ emission and excitation polarization filters and the top optics head. Light from a continuous light source, preferably a xenon-arc source, is routed through an excitation filter, low-luminescence fiber optic cable, and a polarization filter, which typically is in the S orientation. A beamsplitter then splits the light, reflecting polarized light into the assay well and transmitting light into the light monitor. Light emitted from the assay well may pass back through the beamsplitter and then is routed through a fiber optic cable to an emission and polarization filter (in either the S or P orientation) that conditions the light before detection by a photomultiplier tube.

The analyzer makes two measurements for each assay well, one with excitation and emission polarizers aligned and one with excitation and emission polarizers crossed (as described above). Either polarizer may be static or dynamic, and either polarizer may be set to be S or P.

The continuous light source preferably comprises a high-intensity, high-color temperature light source, such as a xenon arc lamp. Such a lamp minimizes photon noise and hence reduces reading time at a given noise level. When combined with the optimized chemiluminescence detection system, the continuous high-intensity light source increases light throughput and decreases background.

As in luminescence intensity mode, confocal optics elements may direct the excitation light into a small sensed volume in a selected region of the well. The best S/N ratio typically is obtained from the middle of each well, because spurious polarization signals from luminophores bound to the well surfaces is minimized. Conditions that optimize the S/N and S/B ratios may be determined empirically.

For luminescence polarization measurements, the user selects the excitation and emission filters, and read time. Optional parameters include the magnitude and duration of plate shaking, well-to-well move time, and Z-height adjustments.

Time-Resolved Luminescence Mode. Time-resolved luminescence measurements use substantially the same optical configuration as luminescence intensity and luminescence polarization measurements, except that time-resolved luminescence methods use the upper optics head and the substitution of a flash lamp, preferably a xenon flash lamp, for a continuous lamp as the light source. The flash lamp creates a brief flash of excitation light, which is followed by time-dependent luminescence. Time-dependent measurements may be delayed to avoid short-lifetime autoluminescence, and hastened to avoid long-lifetime autoluminescence, if desired.

As in luminescence intensity mode, confocal optics elements may direct the excitation light into a small sensed volume in a selected region of the well. The location of the sensed volume can be changed using the Z-height parameter. The optimal S/N and S/B can best be determined empirically.

For time-resolved luminescence, the user selects the excitation and emission filters, delay time, integration time, and cycle time. Optional parameters include the magnitude and duration of plate shaking, well-to-well settle time, and Z-height adjustments.

Chemiluminescence Mode. Chemiluminescence measurements use a dedicated read head and photomultiplier tube adjacent the top optics head and separate from those used in photoluminescence measurements. Light emitted from an assay well is collected through a specially-baffled read head and aperture that reduce well-to-well cross-talk. Collected light then is routed through a low-luminescence fiber optic cable to an optimized photomultiplier tube having relatively low dark counts and a blue-green shifted response.

Alternatively, chemiluminescence measurements may use the photoluminescence optical system, especially if it is desirable to sense chemiluminescence from a sensed volume within the sample container. To reduce background in this mode, the light source module in the photoluminescence system may be "parked" between detectors, so that the associated floating head assembly abuts only a solid surface.

For luminescence measurements, the user can select read time. Optional features include plate shaking, well-to-well settle time, and Z-height adjustments.

Absorbance Mode. Absorbance measurements require a combination of top illumination and bottom detection, or bottom illumination and top detection, and may use continuous or flash light sources.

Measurement Modes

The analyzer may support a variety of measurement modes for detecting luminescence, including (1) photon counting, (2) current integration, and (3) imaging modes. Aspect of these measurement modes are described below to show the versatility and sensitivity of the analyzer. Additional measurement modes and/or alternative methods for performing the described measurement modes also may be employed in conjunction with the analyzer provided by the invention.

Photon-Counting Mode. Transmitted light may be detected in photon-counting mode. In this approach, the photons comprising the detected light are counted, and intensity is reported as the number of counted photons per unit time. Photon counting is well-suited for assays with low light levels, because each photon is individually reported. Conversely, photon counting is ill-suited for assays with high light levels, because the detector may become saturated and unable to distinguish the arrival of one photon from the arrival of more than one photon. Suitable detectors for practicing this method include PMTs.

Current-Integration Mode. Transmitted light also may be detected in current-integration mode. To decrease the average read time per well, the electronics can be configured to integrate the detector current resulting from the luminescence signal until a preset threshold is achieved. This is equivalent to collecting light from the well until a predetermined number of photons are collected. The component of the signal-to-noise ratio due to the photon noise of the emission light then will be equal to the square root of the number of photons collected by the detector. This feature is implemented using an integrating current-to-voltage converter at the detector output coupled to an analog comparator in parallel with an analog-to-digital converter. At the beginning of each measurement cycle, the integrator is reset and the time required for the integrated detector current to trip the comparator is measured. The integration time is a representation of the number of photons collected and hence the signal level. If the signal is too small to cause the comparator to be tripped within the maximum time allowed for the integration, the analog-to-digital converter is used to digitize the voltage appearing at the output of the integrator. Because the value of the integration capacitor and the voltage across it both are known, the number of photons collected can be calculated by taking the product of the integration capacitance and the measured voltage and dividing it by the electronic charge ($1.602 \times 10^{-19}$ Coulombs per electron). Suitable detectors for practicing this method include PMTs.

Imaging Mode. In addition to analysis of single wells, this invention also supports simultaneous reading of many wells located in a fixed area of a microplate. Large-area fiber optic bundles and an imaging charged-coupled device (CCD) detector make it possible to excite and detect a fixed area of the microplate at once. Using this method, the detection limit and time to read a microplate is constant regardless of the number of wells on the microplate as long as the fiber size in the bundle is small compared to the smallest well to be measured (e.g., >4 fibers per well) and the CCD pixel size is small compared to the fiber size (e.g., >4 pixels per fiber). If the fiber optic bundle is randomly oriented, a calculation procedure can be used during setup to map each CCD pixel to a specific location on the microplate. For example, a single microplate well containing a fluorescent compound can be used to map the CCD pixels through the fiber bundle to the microplate surface by repositioning the well repeatedly to include all CCD pixels.

The above description elaborates on the general architecture of the invention, while also describing preferred embodiments. Other related embodiments are possible and may be desirable for specific applications. For example, it may be desirable to commercialize only a portion of the preferred embodiment to meet the needs of different customers or specific markets. Also, the preferred embodiments provide for an expandable architecture wherein the light sources and detectors can be added as required to provide new assay modalities, or to take advantage of new types of light source and detectors, as they become commercially available. For example, blue LEDs have become commercially available only in the last few years, and blue laser diodes are expected to become commercially available within the next few years. The architecture of the invention is designed to be flexible so as to allow incorporation of newly commercialized technology with the goal of making such technology available to high-throughput screening laboratories at the earliest possible date.

Another alternative embodiment may include a plurality of confocal detection systems mounted in a linear array or matrix. A linear array of 8 or 12 confocal detectors may be used with one or more light sources and 8 or 12 detectors to simultaneously detect an entire row or column of a 96 well microplate. The same detectors could also be used to read 384 or 1536 well plates with the proper aperture installed since the well-to-well pitch of the hedger density plates are evenly divisible into that of the 96 well plate. In another example, the confocal detection systems could be mounted in an n-by-m array and could also detect one or more plate formats.

Accordingly, while the invention has been disclosed in its preferred form, the specific embodiment thereof as disclosed and illustrated herein is not to be considered in a limiting sense, because numerous variations are possible and no single feature, function, or property of the preferred embodiment is essential. The invention is to be defined only by the scope of the issued claims.

We claim:

1. A device for detecting chemiluminescence from a sample, the device comprising:

a stage for supporting a sample in a well at an examination site;

an optical relay structure having an end directed toward the examination site for transmitting chemiluminescence from the sample to a detector; and a mask structure having plural apertures of different dimensions, moveably mounted relative to the end of the optical relay structure, so that an effective diameter for the optical relay structure can be selected to complement a particular dimension of the well.

2. The device of claim 1, wherein the well has a diameter, the mask structure having an aperture with a diameter approximately equal to the diameter of the well.

3. The device of claim 1, wherein at least some of the apertures are configured to correspond to wells in microplates having one or more of the following well formats: 96, 384, 1536, 3456, and 9600.

4. The device of claim 1, wherein the optical relay structure includes at least one fiber optic cable.

5. The device of claim 1, wherein the detector is a photomultiplier tube, a photodiode, or a charge-coupled device.

6. The device of claim 1, the stage being configured to support the sample at the examination site in one of a plurality of microplate wells, the wells having top edges defining an upper plane, wherein the end of the optical relay structure is spaced a distance G from the upper plane, G being just high enough so that another well can be moved smoothly into alignment with the end of the optical relay structure without altering G.

7. The device of claim 1 further comprising a drive mechanism that adjusts the distance between the end of the optical relay structure and the examination site.

8. The device of claim 1 further comprising a sensor that detects proximity of the end of the optical relay structure relative to the well.

9. The device of claim 1 further comprising a second optical relay structure having an end directed toward the examination site for transmitting luminescence from the examination site to a second detector.

10. The device of claim 1 further comprising a baffle surrounding the end of the optical relay structure that blocks extraneous light from outside the well from entering the optical relay structure.

11. A device for detecting chemiluminescence from a sample, the device comprising:
a stage for supporting a sample in a well at an examination site;
an optical relay structure having an end directed toward the examination site for transmitting chemiluminescence from the sample to a detector; and
a mask structure having an aperture operatively positioned between the examination site and the end of the optical relay structure, the mask structure being configured to permit selection of different aperture sizes, so that an effective diameter for the optical relay structure can be selected to complement a particular dimension of the well.

12. The device of claim 11, the mask structure having plural apertures of different dimensions, the mask structure being moveably mounted relative to the end of the optical relay structure, so that the effective diameter of the optical relay structure can be selected by moving the mask structure relative to the end of the optical relay structure.

13. The device of claim 11, the mask structure having a variable-dimension aperture, so that the effective diameter of the optical relay structure can be selected by varying the size of the variable-dimension aperture.

14. The device of claim 11 further comprising a baffle surrounding the end of the optical relay structure that blocks extraneous light from outside the well from entering the optical relay structure.

15. A device for detecting chemiluminescence from a sample, the device comprising:
a stage for supporting a sample in a well at an examination site;
an optical relay structure having an end directed toward the examination site for transmitting chemiluminescence from the sample to a detector; and
a baffle surrounding the end of the optical relay structure that blocks extraneous light from outside the well from entering the optical relay structure, wherein the baffle has a substantially black surface with rugosities, generally facing the stage, and configured to absorb light.

16. The device of claim 15, wherein the optical relay structure includes a fiber optic cable having a diameter, the baffle having a diameter at least about twice the diameter of the fiber optic cable.

17. The device of claim 15, wherein the baffle further functions as a mask structure having plural apertures of different dimensions, movably mounted relative to the end of the optical relay structure, so that an effective diameter for the optical relay structure can be selected to complement a particular dimension of the well.

18. The device of claim 15, wherein the optical relay structure includes at least one fiber optic cable.

19. The device of claim 15, wherein the detector is a photomultiplier tube, a photodiode, or a charge-coupled device.

20. The device of claim 15, wherein at least a portion of the substantially black surface is covered by an anti-reflective coating.

21. The device of claim 15, the stage being configured to support the sample at the examination site in one of a plurality of microplate wells, the wells having top edges defining an upper plane, wherein the end of the optical relay structure is spaced a distance G from the upper plane, G being just high enough so that another well can be moved smoothly into alignment with the end of the optical relay structure without altering G.

22. The device of claim 15 further comprising a drive mechanism that adjusts the distance between the end of the optical relay structure and the examination site.

23. The device of claim 15 further comprising a sensor that detects proximity of the end of the optical relay structure relative to the well.

24. The device of claim 15 further comprising a second optical relay structure having an end directed toward the examination site for transmitting luminescence from the examination site to a second detector.

25. The device of claim 15, wherein the baffle further functions as a mask structure having a variable-dimension aperture operatively positioned adjacent the end of the optical relay structure, so that an effective diameter for the optical relay structure can be selected to complement a particular dimension of the well.

26. A method for detecting chemiluminescence from a sample, the method comprising:
choosing a well for holding the sample;
directing an end of an optical relay structure toward the well for transmitting chemiluminescence from the sample to a detector;
positioning a mask structure having at least one aperture operatively between the well and the end of the optical relay structure, so that chemiluminescence from the sample may be transmitted through the aperture toward the end, the mask structure being configured to permit selection of different aperture sizes;
selecting an aperture size to create an effective diameter for the optical relay structure to complement a particular dimension of the well and detecting chemiluminescence emitted from the sample.

27. The method of claim 26, the mask structure having plural apertures of different dimensions, the mask structure being moveably mounted relative to the end of the optical relay structure, wherein the step of selecting an aperture size includes the step of moving the mask structure relative to the end of the optical relay structure.

28. The method of claim 26, the mask structure having a variable-dimension aperture, wherein the step of selecting an aperture size includes the step of varying the size of the aperture.

29. The method of claim 26 further comprising the step of positioning a baffle around the end of the optical relay structure to block extraneous light from outside the well from entering the optical relay structure.

* * * * *